US 6,316,005 B1
United States Patent
Korshus et al.

(10) Patent No.: US 6,316,005 B1
(45) Date of Patent: Nov. 13, 2001

(54) BORRELIA BURGDORFERI BACTERIN

(75) Inventors: Jon B. Korshus, Minneapolis, MN (US); Paul L. Runnels, Floyd, IA (US); Richard L. Sharpee, Green Oaks, IL (US); Ronald F. Schell, Madison; Steven M. Callister, Onalaska, both of WI (US)

(73) Assignee: Solvay Animal Health, Inc., Mendota Heights, MN (US)

( * ) Notice: Subject to any disclaimer, the term of this patent is extended or adjusted under 35 U.S.C. 154(b) by 0 days.

(21) Appl. No.: 08/722,013

(22) PCT Filed: Apr. 11, 1995

(86) PCT No.: PCT/US95/04455

§ 371 Date: Jan. 21, 1997

§ 102(e) Date: Jan. 21, 1997

(87) PCT Pub. No.: WO95/27504

PCT Pub. Date: Oct. 19, 1995

Related U.S. Application Data

(63) Continuation-in-part of application No. 08/226,297, filed on Apr. 11, 1994, now abandoned.

(51) Int. Cl.$^7$ ............... A61K 39/02; A61K 39/116; A61K 39/00; A01N 63/00
(52) U.S. Cl. .................. 424/234.1; 424/203.1; 424/282.1; 424/184.1; 424/93.4; 424/93.1; 424/9.2; 424/828; 514/825
(58) Field of Search ................ 426/203.1, 234.1, 426/828, 9.2, 282.1, 186.1, 93.4, 93.1; 530/806, 820, 825; 514/825

(56) References Cited

U.S. PATENT DOCUMENTS

| | | | |
|---|---|---|---|
| 4,721,617 | * 1/1988 | Johnson | 424/92 |
| 5,248,501 | * 9/1993 | Parnell | 424/195.1 |
| 5,385,826 | * 1/1995 | Schell et al. | 435/7.32 |
| 5,523,089 | 6/1996 | Bergstrom et al. | 424/262.1 |
| 5,530,103 | 6/1996 | Livey et al. | 530/416 |
| 5,582,829 | * 12/1996 | Alliger et al. | 424/234.1 |
| 5,688,512 | * 11/1997 | Bergstrom et al. | 424/234.1 |
| 5,747,294 | * 5/1998 | Flavell et al. | 435/70.21 |
| 5,747,309 | * 5/1998 | Allan et al. | 435/172.3 |

FOREIGN PATENT DOCUMENTS 465 204 A2 * 8/1982 (EP).

WO 93/04175 * 3/1993 (WO).

OTHER PUBLICATIONS

E Oden et al. Dev. Biol. Standard. 24: 181–187, 1973.*
T Masuzawa et al. Micribiol. Immunol. 37: 79–83, 1993.*
Johnson et al. Zbl. Bakt. Hyg. A 263: 45–48, 1986.*
Kazmierczak et al. J. Am. Vet. Assoc. 203: 1524–1528, 1986.*
Lovrich, S.D. et al., Infection and Immunity, 1995, p. 2113–2119.
Lovrich, S.D. et al., Infection and Immunity, 1993, p. 4367–4374.
Lovrich, S.D. et al., Journal of Infectious Diseases, 1994, 170:115–121.
Lim, Lony C.L. et al., Infection and Immunity, 1994, p. 2825–2833.
Craft, Joseph E. et al., J. Clin. Invest., 1986, 78:934–939.
Wilske, B, et al., Res. Microbiol. 1992, 143:583–596.
Jonsson, Maria et al., Infection and Immunity, 1992, p. 1845–1853.

* cited by examiner

Primary Examiner—S. Devi
(74) Attorney, Agent, or Firm—Darby & Darby

(57) ABSTRACT

A bacterin including effective immunizing amounts of two non-crossprotective isolates of inactivated *Borrelia burgdorferi*, an adjuvant in an amount effective to enhance the immunogenicity of the inactivated *Borrelia burgdorferi* isolates and a suitable carrier is provided herein. The bacterin may also contain a third non-crossprotective isolate. A bacterin including effective immunizing amounts of an antigenic subunit derived from a first *Borrelia burgdorferi* isolate and a second, non-crossprotective *Borrelia burgdorferi* isolate, an adjuvant in an amount effective to enhance the immunogenicity of the antigenic subunits and a suitable carrier is also provided. The bacterin may also contain an effective immunizing amount of an antigenic subunit of a third *Borrelia burgdorferi*. Further provided is a bacterin which includes effective immunizing amounts of two non-crossprotective isolates of inactivated *Borrelia burgdorferi* and one or more antigenic subunits from the non-crossprotective isolates, an adjuvant in an amount effective to enhance the immunogenicity of the inactivated *Borrelia burgdorferi* and antigenic subunits and a suitable carrier. Methods of immunizing an animal against *Borrelia burgdorferi* infection which comprise administering to the animal a dose of a bacterin provided herein are also provided.

38 Claims, 20 Drawing Sheets

Vaccinates
S-1-10 Immunoblot

Vaccinates
C-1-11 Immunoblot

Vaccinates
S-1-10 Immunoblot

Vaccinates
C-1-11 Immunoblot

Vaccinates
S-1-10 Immunoblot

Vaccinates
C-1-11 Immunoblot

Vaccinates
S-1-10 Immunoblot

Vaccinates
C-1-11 Immunoblot

—186KD
—88KD

—49.5KD

—32.5KD
—31KD OspA
—27.5KD 667 673 671 669 665 663 661 655 651 612 610 608 598 556 554 Mab

Nonvaccinates Prechallenge
S-1-10 Immunoblot

—32.5KD
—31KD OspA
—27.5KD 677 673 671 669 665 663 661 655 651 612 610 608 598 556 554 Mab

Nonvaccinates Prechallenge
C-1-11 Immunoblot

FIGURE 12B

Nonvaccinates Postchallenge
S-1-10 Immunoblot

Nonvaccinates Postchallenge
C-1-11 Immunoblot

KD 97.4—

66.2—

45.0—

31.0—

21.5—

746PU 746PC 746PsC 758PU 758PC 758PsC 768PU 768PC 768PsC 782PU 782PC 782PsC 847PU 847PC 847PsC OspA mAb

Vaccinates – 5X10⁸ Cells/Dose
C-1-11 Immunoblot

835PU 835PC 835PsC 851PU 851PC 851PsC 855PU 855PC 855PsC 863PU 863PC 863PsC 879PC 879PsC OspA mAb

Vaccinates – 5X10⁸ Cells/Dose
C-1-11 Immunoblot

FIGURE 15B

Vaccinates – 5X10⁸ Cells/Dose
S-1-10 Immunoblot

FIGURE 16A

Vaccinates – 5X10⁸ Cells/Dose
S-1-10 Immunoblot

760PV 760PC 760PsC 774PV 774PC 774PsC 786PV 786PC 786PsC 831PV 831PC 831PsC 843PV 843PC 843PsC OspA mAb

Vaccinates − 5X10⁷ Cells/Dose
C-1-11 Immunoblot

849PV 849PC 849PsC 853PV 853PC 853PsC 859PV 859PC 859PsC 871PV 871PC 871PsC 881PC 881PsC OspA mAb

Vaccinates − 5X10⁷ Cells/Dose
C-1-11 Immunoblot

FIGURE 17B

Nonvaccinates Prechallenge
C-1-11 Immunoblot

FIGURE 18A

Nonvaccinates Post Tick Challenge
C-1-11 Immunoblot

FIGURE 18B

Nonvaccinates Prechallenge
S-1-10 Immunoblot

Nonvaccinates Post Tick Challenge
S-1-10 Immunoblot

BORRELIA BURGDORFERI BACTERIN

RELATED APPLICATIONS

This application is a national stage application under section 371 of PCT application PCT/US95/04455, filed Apr. 11, 1995, which is a continuation-in-part of U.S. Ser. No. 08/226,297, filed Apr. 11, 1994, now abandoned.

BACKGROUND OF THE INVENTION

Lyme disease was first described by Steere et al. in 1977 who reported an epidemic of arthritis in Lyme, Old Lyme and East Haddam, Connecticut. In 1982, Dr. Willy Burgdorfer discovered a new spirochete in the midgut of *Ixodes dammini* ticks (see Burgdorfer, W. A. et al., (1982) Science 216: 1317–1319). This spirochete was subsequently shown to elicit an immune response in infected rabbits which paralleled that in humans with Lyme disease, and is now known to be the etiological agent of the disease. The spirochete was subsequently named *Borrelia burgdorferi*.

While Ixodes ticks are the most commonly encountered vectors of *Borrelia burgdorferi*, the spirochetes have also been found in deerflies, horseflies and mosquitoes. Spirochetes enter an animal host when the animal is bitten by the vector. The *B. burgdorferi* spirochetes reside in various tissues of the host animal, where they may lead to long term infection.

*Borrelia burgdorferi* have recently been shown to possess a unique type of extra chromosomal DNA, linear plasmids, which range in length from 0.5 to 50 kb (Bergstrom, S. et al., (1991) Scand. J. Infect. Dis.—Suppl. 77: 102–107). These plasmids contain the genes encoding the two major outer surface proteins (Osp) expressed by *B. burgdorferi*, OspA and Osp B (Bergstrom et al., 1991). These proteins are believed to be major antigens involved in the immunity to *B. burgdorferi* infection. Schwan and Simpson (Schwan, T. G. and Simpson, W. J., (1991) Scand. J. Infect. Dis.—Suppl. 77: 94–101) report heterogeneity of the Osp A and B proteins amongst different *B. burgdorferi* isolates, as well as on the same isolate grown at different temperatures in vivo and studies at different stages during the infection of mice.

The initial stage of Lyme disease is characterized by an expanding skin lesion, erythema chronicum migrans (Asbrink, E. and Hovmark, A.,(1988) Ann. N.Y. Acad. Sci. 539: 4–15; Halperin, J. J., (1991) Scand. J. Infect. Dis.— Suppl. 77: 74–80). Subjects also frequently develop arthritis. However, in only a small percentage of these subjects is the arthritis chronic (Steere, A. C., (1991) Scand. J. Infect. Dis.—Suppl. 77: 51–54). *Borrelia burgdorferi* may also infect the heart muscle. Cardiac involvement in Lyme disease has mainly been reported as transitory. However, animal studies revealed that skeletal and heart muscles are regularly affected and that the spirochetes appeared to be located within the muscle fibers. This observation suggests that the spirochetes are able to maintain long-term survival in hosts and may thus be able to cause chronic heart complications (Stanek, G. et al. (1991) Scand J. Infect. Dis.—Suppl. 77: 85–87).

*B. burgdorferi* also infects the nervous system in a high percentage of cases, leading to a wide range of acute, chronic and progressive central and peripheral nervous system disorders (Reik, L. et al. (1991) Ann. N.Y. Acad. Sci. 539: 1–3). Published reports have indicated that European populations afflicted with the disease experience dramatic clinical phenomena of neurological disorder, while North American patients develop milder forms of nervous system involvement. (Halperin, 1991; Halperin, J. J. et al., (1988) Ann. N.Y. Acad. Sci. 539: 24–34). However, Halperin (1991) report that it is becoming increasingly clear that at least as far as nervous system involvement is concerned, the same range of neurological phenomena occur in both populations. Diagnosis of Lyme disease depends upon a combination of the recognition of the clinical characteristics presented and also of the probability of exposure in endemically infected areas. However, the development of arthritis is often attributed to other causes and not correlated with a spirochete infection. The neurological symptoms which may be the result of *B. burgdorferi* infection can mimic a variety of other neurological conditions (Reik et al., 1988). Adding to these diagnostic complications is the difficulty of detecting the spirochetes in affected tissues.

Borrelia infection has been combatted with antibiotics, e.g., tetracycline, penicillin, amoxycilin, doxycilin, erythromycin and phenoxymethylpenicillin (Neu, H., (1988) Ann. N.Y. Acad. Sci., 539: 314–316; Skoldenberg, B. et al. (1988) Ann. N.Y. Acad. Sci. 539: 317–323; Weber, K. et al. (1988) Ann. N.Y. Acad. Sci. 539: 325–345; Luft., B. J. et al. (1988) Ann. N.Y. Acad. Sci, 539: 352–361). Ceftriaxone, and chemically similar compounds, have also been useful as chemotherapeutic agents (Neu, 1988). However, the establishment of protocols for effective chemical treatment of Lyme disease has been hampered by the lack of data with which an appropriate time period for treatment could be established. Additionally, there has been a lack of studies of the effectiveness of drugs in human patients. Further complicating the therapeutic picture is the need to establish and maintain sufficiently high tissue concentrations of antibiotics to combat chronic Borrelia infection (Neu, 1988; Skoldenberg et al., 1988).

Given this difficulty in the detection and treatment of Lyme disease, as well as the impracticability of managing the spread of spirochete vectors, there has been a recognized need for a vaccine capable of immunizing susceptible animals and humans against *Borrelia burgdorferi* infection. Vaccines have been studied in hamster (Johnson, R. C. et al. (1988) Ann. N.Y. Acad. Sci, 539: 258–263) and rat (Barthold, S. W. et al. (1988) Ann. N.Y. Acad. Sci. 539: 264–273) models. A whole cell *Borrelia burgdorferi* bacterin for use in domestic animals has been developed (U.S. Pat. No. 4,721,617). Vaccines based upon the *B. burgdorferi* Osp A and/or B proteins have also been developed. However, these whole cell and subunit vaccines contain, or are derived from, only one *B. burgdorferi* isolate. By contrast, the bacterin of this invention contains, or is derived from, at least two non-crossprotective *B. burgdorferi* isolates. The bacterin of this invention therefore will provide immune protection against two different types of *B. burgdorferi* isolate, while previously described bacterins provide protection against only one type of isolate. Accordingly, the bacterin provided by this invention will be more useful to vaccinate animals against Lyme disease.

SUMMARY OF THE INVENTION

This invention provides a bacterin which comprises per dose an effective immunizing amount of two non-crossprotective isolates of inactivated *Borrelia burgdorferi*, an adjuvant in an amount effective to enhance the immunogenicity of the inactivated *Borrelia burgdorferi* and a suitable carrier. The non-crossprotective isolates of *Borrelia burgdorferi* may be selected from the Wisconsin, Chicago and European seroprotective groups of *Borrelia burgdorferi* isolates. Presently preferred are isolates from the Wisconsin and Chicago groups. However, isolates belonging to other seroprotective groups may also be used. The bacterin may further comprise a third non-crossprotective inactivated *Borrelia burgdorferi* isolate.

This invention also provides a method of immunizing an animal against infection by *Borrelia burgdorferi* which comprises administering to the animal a dose of the bacterin provided. The animal may be a mammal including, but not limited to, humans and dogs. This invention contemplates administering an additional dose of vaccine to the animal at a suitable interval of time after administration of the preceding dose.

This invention further provides a bacterin which comprises per dose an effective immunizing amount of an antigenic subunit derived from a first *Borrelia burgdorferi* isolate, an effective immunizing amount of an antigenic subunit derived from a second, non-crossprotective *Borrelia burgdorferi* isolate, an adjuvant in an amount effective to enhance the immunogenicity of the antigenic subunits and a suitable carrier. The bacterin may further comprise an effective immunizing amount of an antigenic subunit of a third, non-crossprotective *Borrelia burgdorferi* isolate. This invention provides a method of immunizing an animal against disease caused by *Borrelia burgdorferi* which comprises administering to the animal a dose of the bacterin.

This invention also provides a bacterin which comprises per dose an effective immunizing amount of two non-crossprotective isolates of inactivated *Borrelia burgdorferi* and one or more antigenic subunits from the non-crossprotective isolates, an adjuvant in an amount effective to enhance the immunogenicity of the inactivated *Borrelia burgdorferi* and antigenic subunits and a suitable carrier.

This invention further provides for the use of a bacterin which comprises an effective immunizing amount of at least two non-crossprotective isolates of inactivated *Borrelia burgdorferi*, an adjuvant in an amount effective to enhance the immunogenicity of the inactivated *Borrelia burgdorferi* and a suitable carrier for the immunization of animals against infection by *Borrelia burgdorferi*.

The invention also provides for the use of a bacterin which comprises an effective immunizing amount of at least two non-crossprotective isolates of inactivated *Borrelia burgdorferi* and one or more antigenic subunits from the non-crossprotective isolates, an adjuvant in an amount effective to enhance the immunogenicity of the inactivated *Borrelia burgdorferi* and antigenic subunits and a suitable carrier for the immunization of animals against infection by *Borrelia burgdorferi*.

BRIEF DESCRIPTION OF THE FIGURES

FIGS. 12A and 12B. Western Immunoblots of nonvaccinate serum collected seven months post second vaccination pre-tick challenge (PC) against isolates S-1-10 (FIG. 12A) and C-1-11 (FIG. 12B).

FIGS. 15A and 15B. Western immunoblots (isolate C-1-11) of serum from dogs vaccinated with bacterin formulated at full dose ($5 \times 10^8$ cells of each isolate per dose). Serum was collected at prevaccination (PV), pre-tick challenge (PC), and twelve weeks post challenge.

FIGS. 16A and 16B. Western immunoblots (isolate S-1-10) of serum from dogs vaccinated with bacterin formulated at full dose ($5 \times 10^8$ cells of each isolate per dose). Serum was collected at prevaccination (PV), pre-tick challenge (PC), and twelve weeks post challenge.

FIGS. 17A and 17B. Western immunoblots (isolate C-1-11) of serum from dogs vaccinated with bacterin formulated at full dose ($5\times10^7$ cells of each isolate per dose). Serum was collected at prevaccination (PV), pre-tick challenge (PC) and twelve weeks post challenge.

FIGS. 18A and 18B. Western immunoblots (isolate C-1-11) of serum collected from nonvaccinated controls at the time of tick challenge (FIG. 18A) and twelve weeks post tick challenge (FIG. 18B).

DETAILED DESCRIPTION OF THE INVENTION

Figure 1:
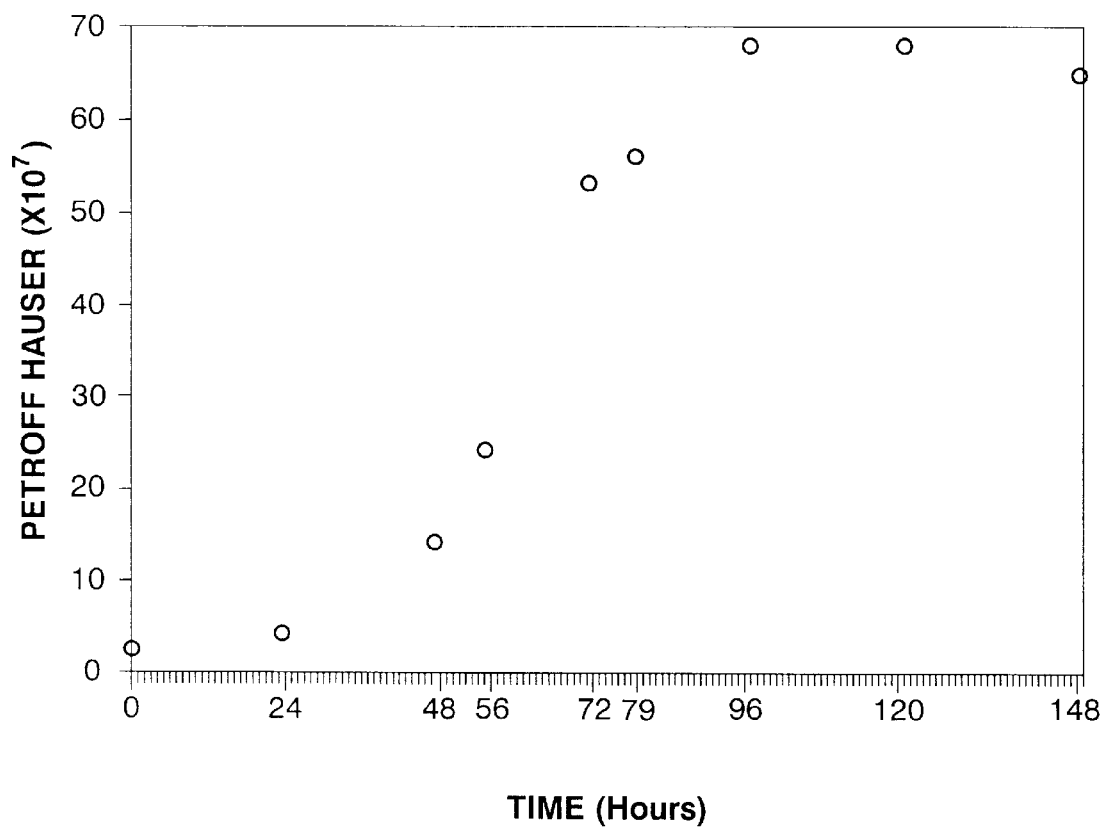
FIG. 1. Growth curve of a viable *B. burgdorferi* culture. The vertical axis indicates the number of cells ($\times 10^7$) as determined on a Petroff-Hauser counter.

This invention provides a bacterin which comprises per dose an effective immunizing amount of two noncrossprotective isolates of inactivated *Borrelia burgdorferi*, an adjuvant in an amount effective to enhance the immunogenicity of the inactivated *Borrelia burgdorferi* and a suitable carrier.

Typically, the effective immunizing amount of the non-crossprotective isolates of inactivated *Borrelia burgdorferi* is an amount from about $1\times10^4$ organisms to about $1\times10^{10}$ organisms of each isolate. Desirably, the effective immunizing amount of the isolates of inactivated *Borrelia burgdorferi* is an amount from about $1\times10^4$ organisms to about $1'10^9$ organisms of each isolate. More desirably, the effective immunizing amount of the isolates of inactivated *Borrelia burgdorferi* is an amount about $1\times10^4$ organisms to about $1\times10^8$ organisms of each isolate. In a preferred embodiment the effective immunizing amount of the isolates of inactivated *Borrelia burgdorferi* is an amount of about $10^7$ organisms of each isolate. In a particularly preferred embodiment the effective immunizing amount of the isolates of inactivated *Borrelia burgdorferi* is about $5\times10^7$ organisms of each isolate. In another particularly preferred embodiment the effective immunizing amount of the isolates of inactivated *Borrelia burgdorferi* is about $5\times10^8$ organisms of each isolate.

For the purposes of this invention, an "inactivated" *Borrelia burgdorferi* isolate is an isolate which is capable of eliciting an immune response in an animal but which is incapable of infecting the animal. The *Borrelia burgdorferi* isolates may be inactivated by an agent selected from the group consisting of binary ethyleneimine, formalin, β-propriolactone or heat. In the presently preferred embodiment of this invention, the *Borrelia burgdorferi* isolates are inactivated by binary ethyleneimine.

The two non-crossprotective isolates of inactivated *Borrelia burgdorferi* may be selected from seroprotective groups A, B or C of *Borrelia burgdorferi* isolates. As used in this invention, the terms "seroprotective group A of *B. burgdorferi* isolates" defines a seroprotective group of *B. burgdorferi* isolates which includes Wisconsin isolate S-1-10, and isolates 297 and B31; "seroprotective group B of *B. burgdorferi* isolates" defines a seroprotective group of *B. burgdorferi* isolates which includes the Chicago isolate C-1-11; and "seroprotective group C of *B. burgdorferi* isolates" defines a seroprotective group of *B. burgdorferi* isolates which includes the European isolates. Example 10 describes in vitro crossprotection studies of nine *B. burgdorferi* isolates which indicate that six belong to seroprotective group A, one belongs to seroprotective group B and two belong to seroprotective group C. However, use of non-crossprotective isolates from other seroprotective groups in the bacterin of this invention is contemplated. The results set forth in Example 12 (see below) demonstrate that there are at least two seroprotective groups of *Borrelia burgdorferi* in addition to seroprotective groups A, B and C.

Crossprotectivity may be determined by inoculating an animal, e.g., a hamster, with a live *B. burgdorferi* isolate. Antiserum from such an animal is then administered to cultures of *B. burgdorferi* isolates. The antibodies, in conjunction with complement, should cause cell death in cultures of the same isolate which was used to inoculate the animal. If the antibodies recognize an antigenic determinant on a second isolate, they will induce cell death in a culture of that isolate. The first and second *B. burgdorferi* isolates are therefore said to be crossprotective. Crossprotectivity can also be assessed by inoculating an animal with a *B. burgdorferi* isolate, isolating antiserum from the animal and inoculating another animal of the same species with this antiserum. This animal is subsequently challenged with either the same or a second *B. burgdorferi* isolate. The antibodies should offer passive immunity to the recipient animal against challenge by the same isolate. If the antibodies also transfer passive immunity against a second isolate, the isolates are crossprotective.

Crossprotective isolates express outer surface proteins (Osp) which share antigenic determinants recognized by the same antibodies. Crossprotective isolates are said to belong to the same seroprotective group. Accordingly, a "seroprotective group" is a group of *B. burgdorferi* isolates which share common protective outer surface proteins. Antibodies which recognize these proteins transfer passive immunity against challenge by any isolate which is a, member of the same seroprotective group.

Antibodies directed to one member of a pair of non-crossprotective isolates will not confer passive immunity against the other member of the pair. Non-crossprotective isolates therefore belong to different seroprotective groups. Vaccination with an inactivated *B. burgdorferi* isolate will not confer passive immunity to an animal against challenge by non-crossprotective isolates. The bacterin of this invention, which comprises at least two non-crossprotective isolates, will be effective in producing borreliacidal antibodies against the members of two seroprotective groups. The bacterin therefore provides a broader spectrum of immune protection than can be obtained with presently available vaccines, which do not make use of multiple, non-crossprotective *B. burgdorferi* isolates.

In one embodiment of this invention, the non-crossprotective isolates of *Borrelia burgdorferi* are selected from seroprotective groups A and B of *Borrelia burgdorferi* isolates. The seroprotective group A *Borrelia burgdorferi* isolate may be the Wisconsin isolate S-1-10, or the 297 or B31 isolate. In the presently preferred embodiment of this invention, the seroprotective group A *Borrelia burgdorferi* isolate is the Wisconsin S-1-10 isolate. Preferably, the Seroprotective group B *Borrelia burgdorferi* isolate is the Chicago C-1-11 isolate. However, this invention can also be practiced with other inactivated *B. burgdorferi* isolates which will be classified in seroprotective group B. *Borrelia burgdorferi* strain S-1-10 and *Borrelia burgdorferi* strain C-1-11 were deposited on Apr. 11, 2000 at the American Type Culture Collection (ATCC) located at 10801 University Blvd., Manassas, Va. 20110-2209, USA and have ATCC deposit designations PTA-1679 and PTA-1680, respectively.

For the purposes of this invention, an adjuvant is a composition of matter capable of enhancing the immunogenicity of antigens when the adjuvant is administered as part of a bacterin. Adjuvants useful in the bacterin of this invention may be selected from the group consisting of aluminum hydroxide, carbopol, lipopolysaccharide (LPS) and derivatives thereof. The term "lipopolysaccharide" as used herein refers to a group of polysaccharides known to those of skill in the art by their presence in the cell wall of bacteria and useful as adjuvants. Certain examples of lipopolysaccharides and derivatives thereof, which demonstrate an adjuvant effect, have been used in vaccines. The use of lipopolysaccharides or derivatives thereof in connection with the bacterin of this invention is contemplated. In the presently preferred embodiment of this invention, the adjuvant is aluminum hydroxide. However, any other adjuvant capable of enhancing the immunogenicity of inactivated *Borrelia burgdorferi* may be used in the bacterin of this invention.

As used herein, an "effective amount" of an adjuvant is any amount of the adjuvant effective to enhance the immunogenicity of antigens in the bacterin. Typically, the effective amount of the adjuvant is an amount from about 1.0% by volume of a dose of the bacterin to about 15% by volume. Desirably, the effective amount of the aluminum hydroxide adjuvant is an amount from about 5% by volume to about 10% by volume. Most pereferably the effective amount of aluminum hydroxide adjuvant is 7.5% by volume.

"Carriers" as used herein means any of the standard diluents for a bacterin which are well known to those skilled in the art. In the presently preferred embodiment of this invention, the carrier comprises an aqueous buffer, e.g., physiological saline, and preservatives, e.g., nystatin and gentamicin.

The bacterin of this invention may further comprise an effective immunizing amount of a third, non-crossprotective isolate of inactivated *Borrelia burgdorferi*.

This invention provides a method of immunizing an animal against infection by *Borrelia burgdorferi* which comprises administering to the animal a dose of the bacterin of this invention. It is well known to those with skill in the art that *Borrelia burgdorferi* is the causative agent of Lyme disease and that infection occurs as the result of bacteria-bearing ticks biting warm blooded host animals. It has been established that animals will synthesize antibodies, in response to inoculation with *Borrelia burgdorferi* and therefore, that vaccination with either inactivated *Borrelia burgdorferi*, or a subunit thereof, is a feasible approach to the prevention of Lyme disease. Given the difficulty of correctly diagnosing Lyme disease, the uncertainty of treatment protocols and the impracticability of controlling the vectors of the disease, a preventative approach to controlling the disease is necessary. Previous *B. burgdorferi* vaccines used contain only one isolate of the bacteria. Accordingly, such vaccines are at best capable of immunizing only against challenge by isolates belonging to the same seroprotective group as the vaccinate isolate. The bacterin provided by this invention can provide immunity against isolates belonging to at least two seroprotective groups, and therefore, offer broader protection than presently available vaccines.

Typically, the animal to which the vaccine of this invention is administered is a mammal. In one preferred embodiment the mammal is a human. In another preferred embodiment of this invention, the mammal is a dog. In the practice of this invention one skilled in the art will be able to determine for each animal to be innoculated, the appropriate age at which the animal is immunocompetent, i.e., having a properly functioning immune system. Immunization would, therefore, be appropriate at the time the animal is immuno- competent and, preferably, prior to exposure to *Borrelia burgdorferi*. For example when the animal to be innoculated is a dog, the dog is at least about twelve weeks old, desirably from about six weeks to about sixteen weeks old, at the time when the bacterin is first administered.

This invention also contemplates administering to the animal an additional dose of vaccine at a suitable interval of time after administration of the preceding dose. The method provided by this invention thus contemplates administering multiple doses of the inactivated *Borrelia burgdorferi* bacterin to an animal. Administration of more than one dose of a bacterin is intended to enhance the immune response of the vaccinated animal to bacterial antigens in comparison to that which may be achieved by the administration of a single dose. Administration of each dose should be separated by an interval of time suitable to allow the animal's immune system to respond more effectively to multiple doses of the bacterin than it does to a single dose. A "suitable" interval of time between administration of multiple doses of a bacterin to an animal is therefore any interval of time between administration of doses of a vaccine sufficient to cause the animal to generate a greater immune response than when a single dose is administered. Typically, the suitable interval of time between administration of doses of the bacterin of this invention is from about two weeks to about five weeks, desirably, about three weeks. This invention further contemplates administering an additional dose of the bacterin to the animal approximately one year after the first administration, and at about annual intervals thereafter. Such administration, known as a "booster" dose, is standard practice in the art of vaccination. The inactivated *Borrelia burgdorferi* bacterin may be administered by any of the routes accepted by the art for administering vaccines. The presently preferred route of administration for the bacterin is by intramuscular injection.

This invention also provides a bacterin which comprises per dose an effective immunizing amount of one or more antigenic subunits derived from a first *Borrelia burgdorferi* isolate, an effective immunizing amount of one or more antigenic subunits derived from a second, non-crossprotective *Borrelia burgdorferi* isolate, an adjuvant in an amount effective to enhance the immunogenicity of the antigenic subunits and a suitable carrier. It is well known in the art that *Borrelia burgdorferi* antigenic determinants are known as "outer surface proteins" (Osp) and are encoded by plasmids contained in the bacteria. Presently known *B. burgdorferi* Osp proteins are the Osp A, Osp B, Osp C, Osp D, and Osp E proteins. Of these proteins, the Osp A and Osp B proteins are the most studied and characterized. The bacterin of this invention contemplates use of an Osp A protein or a combination of Osp A protein and Osp B protein of at least two non-crossprotective *B. burgdorferi* isolates. The bacterin further contemplates the use of other Osp proteins, either alone or in combination with the Osp A and Osp B proteins, which are shown to elicit a borreliacidal antibody response similar to that known for the Osp A protein and Osp A/Osp B protein combination. For a discussion of the preparation of vaccines for lyme disease using antigenic subunits and polypeptides derived from outersurface proteins of *B. burgdorferi* see PCT International Application PCT/US94/08529, published Feb. 9, 1995 as International Publication No. WO 95/04145, the content of which is hereby incorporated by reference.

As discussed hereinabove, cross-protective isolates share antigenic determinants which are capable of being recognized and bound to by antibodies. Thus, the Osp proteins from cross-protective isolates share antigenic determinants in common and are subject to recognition by the same antibodies. Cross-protective isolates are said to belong to the same seroprotective group. Vaccination with one member of a seroprotective group will establish immunity against challenge by other isolates classified in the same seroprotective group. Antibodies directed to one member of a pair of non-crossprotective isolates will not confer passive immunity against the other member of the pair. Non-crossprotective isolates belong to different seroprotective groups. Vaccination with one member of a pair of non-crossprotective isolates will not confer immunity against challenge by the other member of the pair. Thus vaccination with an effective amount of an Osp A protein or a combination of Osp A protein and Osp B protein from one isolate will confer passive immunity against challenge by the same isolate, as well as other, crossprotective, isolates.

Typically, the effective immunizing amount of each of the antigenic subunits derived from the non-crossprotective *Borrelia burgdorferi* isolates is an amount from about one microgram to about 1,000 micrograms.

This invention provides a method of immunizing an animal against *B. burgdorferi* infection which comprises a dose of the bacterin provided herein to the animal.

The bacterin of this invention may further comprise an effective immunizing amount of one or more antigenic subunits derived from a third non-crossprotective *Borrelia burgdorferi* isolate. However, the bacterin is not limited to containing one, two or three non-crossprotective isolates, but may further contain four or more such isolates.

This invention provides a method of immunizing an animal against disease caused by *B. burgdorferi* which comprises administering to the animal a dose of a bacterin comprising three or more non-crossprotective *B. burgdorferi* isolates.

This invention provides a bacterin which comprises per dose an effective immunizing amount of two non-crossprotective isolates of inactivated *Borrelia burgdorferi* and one or more antigenic subunits from the non-crossprotective isolates, an adjuvant in an amount effective to enhance the immunogenicity of the inactivated *Borrelia burgdorferi* and antigenic subunits and a suitable carrier. Also provided is a method of immunizing an animal against disease caused by *B. burgdorferi* which comprises administering to the animal a dose of such a bacterin.

This invention further provides for the use of a bacterin which comprises an effective immunizing amount of at least two non-crossprotective isolates of inactivated *Borrelia burgdorferi*, an adjuvant in an amount effective to enhance the immunogenicity of the inactivated *Borrelia burgdorferi* and a suitable carrier for the immunization of animals against infection by *Borrelia burgdorferi*.

In one embodiment of the use described above, the effective immunizing amount of the non-crossprotective isolates of inactivated *Borrelia burgdorferi* is an amount from about $10^4$ organisms to about $10^{10}$ organisms of each isolate. In a preferred embodiment the effective immunizing amount of the non-crossprotective isolates of inactivated *Borrelia burgdorferi* is an amount from about $10^4$ organisms to about $10^9$ organisms of each isolate. In another preferred embodiment the effective immunizing amount of the non-crossprotective isolates of inactivated *Borrelia burgdorferi* is an amount from about $10^4$ organisms to about $10^8$ organisms of each isolate. In a preferred embodiment the effective immunizing amount of the non-crossprotective isolates of inactivated *Borrelia burgdorferi* is about $10^7$ organisms of each isolate. In a particularly preferred embodiment the effective immunizing amount of the non-crossprotective isolates of inactivated *Borrelia burgdorferi* is about $5 \times 10^7$ organisms of each isolate. In another particularly preferred embodiment the effective immunizing amount of the non-crossprotective isolates of inactivated *Borrelia burgdorferi* is about $5 \times 10^8$ organisms of each isolate.

The invention also provides for the use of a bacterin which comprises an effective immunizing amount of at least two non-crossprotective isolates of inactivated *Borrelia burgdorferi* and one or more antigenic subunits from the non-crossprotective isolates, an adjuvant in an amount effective to enhance the immunogenicity of the inactivated *Borrelia burgdorferi* and antigenic subunits and a suitable carrier for the immunization of animals against infection by *Borrelia burgdorferi*.

In a preferred embodiment of the above described use the effective immunizing amount of the antigenic subunits derived from each of the non-crossprotective *Borrelia burgdorferi* isolates is an amount from about ten micrograms to about 10,000 micrograms.

The invention is further illustrated in the Experimental Details section which follow. The Experimental Details section and Examples contained therein are set forth to aid in an understanding of the invention. This section is not intended to, and should not be interpreted to, limit in any way the invention set forth in the claims which follow thereafter.

EXPERIMENTAL DETAILS

Example 1

Preparation of *Borrelia burgdorferi* Bacterin

Equipment Needed:

Sterile: 20 ml tubes, 250 ml bottles and 10 liter jugs; 200, 500 or 3,000 liter fermenter; serological pipets; magnets; mixing and storage tanks; and centrifuge.

Nonsterile: magnetic stirring motors; pipet aids; peristaltic pumps; tubing and tubing clamps; Petroff/Hauser counting chamber; darkfield microscope; coveralls, gloves, hats, masks, shoe covers and face shields; micropipet and micropipet tips; saline solution blanks.

Microorganisms used: Two isolates of *Borrelia burgdorferi* are used in the preparation of the product, *B. burgdorferi* isolates C-1-11 and S-1-10 obtained from Dr. Steven M. Callister, Gundersen Medical Foundation, La Crosse, Wis. The bacterin will contain adjusted counts of each Borrelia isolate culture to satisfy potency standard requirements.

Identity of each microorganism and frequency of methods of identification: Identification is made on the basis of morphological and serological characteristics. Serological identification of master seed stocks will be with specific antisera, using an indirect fluorescent antibody test.

Virulence, purity, maintenance, and range of cultures: Virulence of the cultures is not an essential criteria for anstigenicity. Purity of the strain is determined by careful examination of the cultural growth using darkfield microscopy, gram stain, serological identification with specific antisera, and testing in accordance with 9 C.F.R. §113.27 using 0.5- to 1.0-ml samples.

Cultures are maintained in Barbour Stoenner Kelly (BSK) medium, which is prepared as described below (see Example 5). Subcultures will be made in BSK medium, the number of subcultures being limited to 10.

Composition of seed and production cultures: Seed and production cultures are grown in BSK medium. Seed stock cultures are grown in BSK medium and frozen after addition of glycerol (10–14% final concentration). Frozen stock cultures are maintained at −70° C. or colder.

Character, size and shape of containers used for growing cultures: Frozen stock cultures are grown in 20-ml screw-cap tubes containing ten ml of medium. The 20-ml culture tubes will be used to inoculate 250-ml bottles or flasks containing 200 ml of medium. The 250-ml bottles or flasks will be used to inoculate 10-liter jugs containing six to eight liters of medium. The 10-liter jugs may be used to inoculate 40-liter jugs containing 25 to 35 liters of medium, a 200-liter fermenter containing 90 to 175 liters of medium, a 500-liter fermenter containing 175 to 375 liters of medium, or a 3000-liter fermenter containing 800 to 2500 liters of medium. The 200-liter fermenter may be used to inoculate a 3,000-liter fermenter containing 300 to 2300 liters of medium.

Storage conditions of seed cultures: Stock cultures are maintained in BSK Medium as frozen cultures at −70° C. or colder.

Methods of preparing suspensions for seeding or inoculation: Four one ml vials of the desired strain of *B. burgdorferi* are thawed, each then being added to 9.0 ml of Barbour Stoner Kelly (BSK) medium (see below). Seed and stock cultures are propagated 10 to 96 hours, as judged by rate of growth, at 32° C.±20° C. prior to transfer to BSK medium. Seed cultures are routinely checked microscopically for purity prior to transfer to production medium. Cell growth of sample tubes was measured by Petroff/Hauser counting at 12 hours and every hour thereafter until passage. *B. burgdorferi* cultures are passaged at a concentration greater than or equal to $1 \times 10^8$ cells per ml. When the concentration of cells becomes greater than $1 \times 10^8$ cells/ml gram staining of each tube culture is carried out and two acceptable culture tubes are pooled for inoculating a 250-ml inoculum. Four 250 ml flasks containing 196.0 ml of BSK medium are inoculated with four ml of the above-described inoculum and are then incubated at 32° C., stationary for 48 to 60 hours. Cell growth is determined by Petroff/Hauser counting at 24 hours and every six hours thereafter. until passage. Passage is at concentrations greater than or equal to $1 \times 10^8$ cells per ml. When the concentration of cells reaches this level, gram staining is conducted of each flask culture and two acceptable flasks are pooled for a ten liter jug inoculation. Each of three ten liter jugs, containing 5880 ml of BSK medium, is inoculated with 120 ml of the above-described culture. The flasks are then incubated at 32° C. for 36 to 48 hours, with slow agitation by magnetic stir bar. Cell growth of one jug is determined by Petroff/Hauser counting at 10 hours, and every six hours thereafter, until passage, which is at a concentration of greater than or equal to $1 \times 10^8$ cells per ml. When the concentration of cells in the cultures reaches this level, gram staining of each jug culture is done, and one jug containing six liters is used to inoculate a 200 liter fermenter containing 144 liters of BSK medium. The fermenters are incubated at 32° C. for approximately 96 hours, with slow agitation (55 rpm), the pH being controlled at 7.2+/−0.2. At 12, 24, 48 and 72 hours, and then every four hours thereafter, cell growth is determined by Petroff/Hauser counting and is checked by gram staining. The culture is inactivated when it reaches the late log phase of growth (approximately $5-7 \times 10^8$ cells per ml).

FIG. 1 shows a growth curve for a *Borrelia burgdorferi* culture. As can be seen from the figure, exponential culture growth began between about 24 and about 48 hours, and continued until about 96 hours, when growth leveled off.

Figure 2:
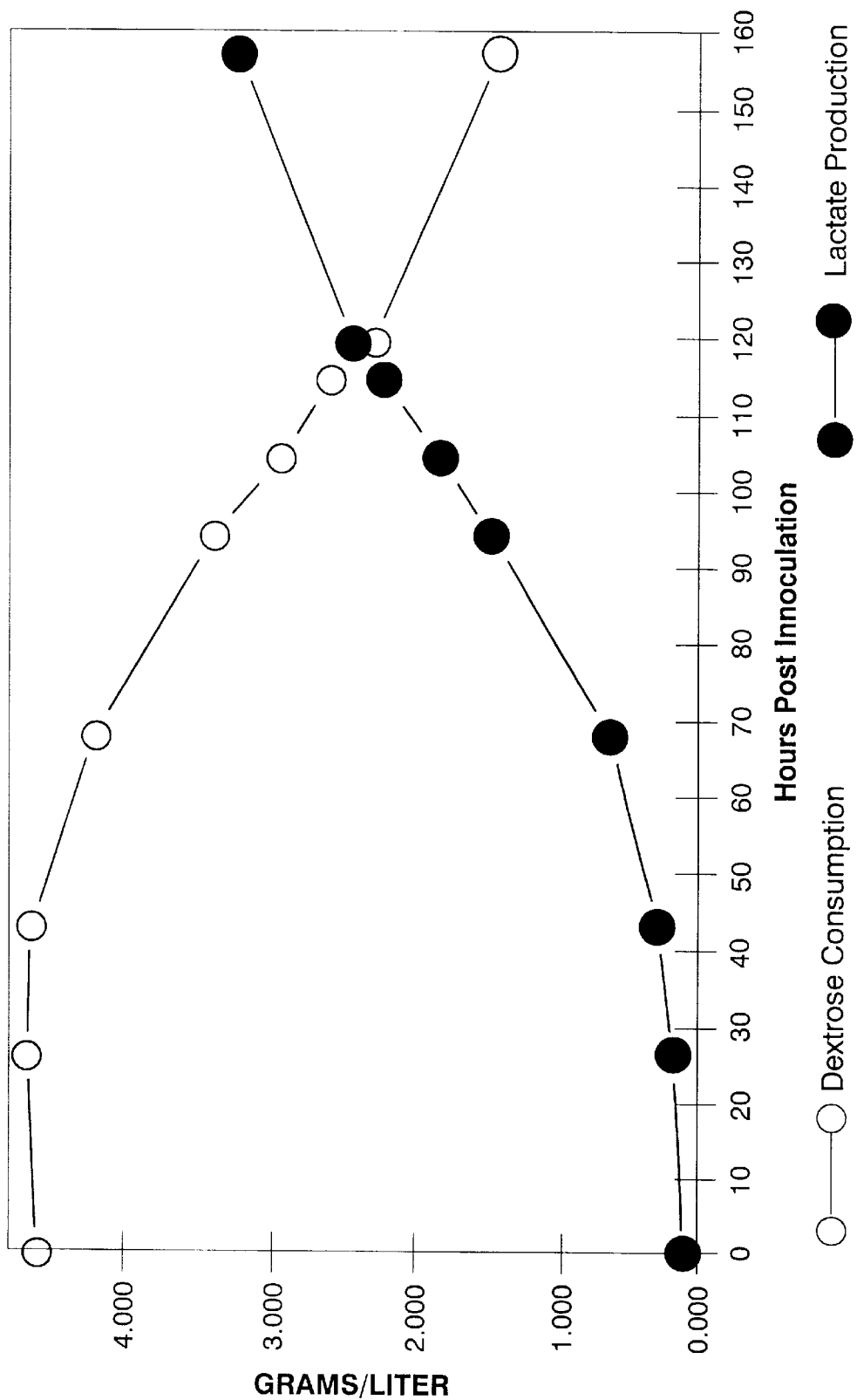
FIG. 2. Dextrose consumption and lactate production in a *B. burgdorferi* culture. Closed circles denote lactate production, and open circles dextrose consumption, in the culture. Values are given in grams per liter of culture medium.

FIG. 2 shows dextrose consumption and lactate production of a *Borrelia burgdorferi* culture. As can be seen from the figure, lactate production increases steadily in the culture. This indicates the importance of controlling pH in the culture. Additionally, it can be seen from the figure that dextrose consumption increases with time, indicating that the bacteria are using this as an energy source, which must therefore be replaced to maintain culture viability or growth.

Technique of inoculating seed and production media: Seed medium is inoculated by direct transfer from the frozen stock culture. Production medium is inoculated by direct transfer of the seed culture. Culture inoculation will use no less than 2% inoculum.

Period of time, conditions, and degree of temperature for incubation: Following inoculation, the vessels shall be incubated at 32° C.±1° C. for 10 to 96 hours and the production fermenters shall be incubated at 32° C.±1° C. for 24 to 120 hours. Sterile NaOH solution is added as needed to adjust the pH to 7.2±0.2.

Character and amount of growth: Daily, throughout incubation, the inoculated production cultures are examined microscopically by Petroff/Hauser quantitation. At the end of the incubation period, the cultures are checked microscopically for contamination using gram strain and/or dark-field examination.

Minimum and maximum times for harvest: The minimum incubation period until harvest will be 24 hours. The maximum incubation period until harvest will be 120 hours.

Technique of harvesting: At the end of the incubation period, each production culture is checked for microscopic purity by gram-stain and/or dark-field examination, and samples are taken for total cell count. The culture containers may be stored at 2° C. to 7° C.

Specifications for acceptable harvest material: Acceptable production growth will contain pure cultures of *Borrelia burgdorferi* demonstrated by gram-stain and/or dark-field microscopy, and will have a Borrelia count of no less than $1 \times 10^8$ organisms per ml. Concentration is determined using a Petroff/Hauser (or equivalent) counting chamber.

Disposition of discarded materials: All materials not used in the preparation of the bacterin shall be disposed of in accordance with Veterinary Services Memorandum No. 800.56.

Example 2

Preparation of the Product

Method of inactivation: The production growth is inactivated with binary ethyleneimine (BEI). Inactivation is conducted at 32° C.±2° C. The appropriate amount of BEI is prepared as a 0.344 M (7.05%) solution. A 7.05% BEI solution is prepared by dissolving 70.48 grams of 2-bromoethylamine hydrobromide (molecular weight 204.89) and 8.00 grams NaOH (MW 40.00) in one liter of deionized water. The dissolved solution is incubated at 37° C. for two hours and then added to the culture at 30 ml per liter under constant agitation (slow stirring). The inactivation is conducted for no less than 24 hours at a pH of 7.3±0.2 with agitation (slow stirring). Upon completion of inactivation, the BEI is neutralized by the addition of sterile sodium thiosulfate. The appropriate amount of sterile sodium thiosulfate solution is prepared as a 3.015 M (47.7%) solution by dissolving 477.0 grams sodium thiosulfate in one liter of deionized water. This solution is filtered through a 0.2 micron filter prior to use and is added to the inactivated culture at 10.6 ml per liter under constant agitation (slow stirring). The neutralization reaction is allowed to proceed for no less than 6 hours at 32° C. under constant agitation (slow stirring at a pH of 7.3±0.2. Gentamicin sulfate and nystatin are added to the culture to final concentrations of 30.0 micrograms per ml, and 30.0 units per ml, respectively. The production organisms are then pooled into sterile holding tanks for further processing.

Inactivation testing: An inactivation test of the bulk is conducted in accordance with 9 C.F.R. §113.100. A sample is taken from the inactivated culture and a tube containing 29 ml of BSK medium is inoculated with 1.0 ml of the sample. At the same time, a sample of the same organism at a concentration of 10 cells per ml known to be viable to serve as a positive growth control is diluted 1:30 in fresh BSK medium using a 29.0 ml BSK bland and diluted in BSK medium from $10^{-1}$ to $10^{-4}$ using 9.0 ml BSK blanks. The tubes are incubated for 14 days at 32° C.±2° C. and are then examined for growth. A satisfactory test is indicated by no evidence of Borrelia growth in the tube containing the inactivated sample. The tubes inoculated with the live organism must have an $ID_{50}$ of $\leq 100$ and $\geq 1$ as calculated by the Reed-Muench method.

Composition, Proportions, Preservatives, and Adjuvants

1. Aluminum hydroxide adjuvant: Aluminum Hydroxide [Al(OH)$_3$] Rehydragel® HPA obtained from Reheis Chemical company (Berkley Heights, N.J.) is added to the bacterial suspension to a final concentration of no less than 1.5 mg (0.15%) Aluminum Oxide (Al$_2$O$_3$) per dose.

2. Saline: Sterile physiological saline (0.85% NaCl—pH 7.2±0.2) may be added as a diluent.

3. Preservatives: Gentamicin sulfate and nystatin are added to the product to a final concentration of no more than 30.0 micrograms per ml, and 30.0 units per ml, respectively.

4. pH: The pH of the completed product will be adjusted to 7.3±0.1 with sterile NaOH or HCl.

Method and degree of concentration: Borrelia harvest material is concentrated by centrifugation and resuspension in sterile saline containing gentamicin sulfate and nystatin to final concentrations of 30.0 micrograms/ml and 30.0 units/ml, respectively. Borrelia harvest material may be concentrated down to ¹⁄₂₀th of the original volume.

Procedures for standardization of the antigen: The bacterin is assembled using the Petroff/Hauser cell count determined after concentration and resuspension of the pellet material. Concentration of Borrelia in each culture is determined as described above. A blending of cultures with high and low concentrations may be used in adjusting the overall concentrations.

Assembly of a Serial

1. Assembly of units to make a serial: Sufficient bulk storage containers of individual pools of each Borrelia isolate are removed from the 4° C. to 7° C. cooler. If required, sterile physiological saline (0.85% NaCl) is used as a diluent. The diluent is autoclaved at 121° C.±2° C. for 30 minutes, or when a probe in the liquid reaches $\geq 119$° C. for not less than 20 minutes.

2. Example of serial assembly:

| Ingredients | Organisms per ml in Concentration | Finished Product Liters | Final Counts per 1.0 ml Dose No Less than |
|---|---|---|---|
| B. burgdorferi Strain C-1-11 | $8.0 \times 10^9$ | 18.750 | $5.0 \times 10^8$ |
| B. burgdorferi Strain S-1-10 | $8.0 \times 10^9$ | 18.750 | $5.0 \times 10^8$ |
| Aluminum Oxide (2% Al$_2$O$_3$) | — | 22.500 | — |
| Gentamicin sulfate (20.0 mg per ml) | — | 0.394 | — |
| Nystatin (25,000 units per ml) | — | 0.315 | — |
| Physiological Saline | — | 239.291 | — |
| TOTAL VOLUME | | 300.000 liters | |

The pH is adjusted to 7.3+/−0.1 with sterile NaOH or HCl. The average serial size will be 300 liters. The maximum serial size will be 900 liters. Inactivated Borrelia suspensions are pooled into a sterile stainless steel tank for assembly. After mixing, the entire serial may be stored in a sterile stainless steel assembly tank or divided into smaller containers and stored at 2° C. to 7° C. until filling, or the product may be immediately vialed and stored at 2° C. to 7° C.

3. Volume of fill and type of vial used: The bacterin is vialed at 1.20 ml±0.05 ml per 1 dose vial. The vials to be used are two ml glass vials.

Method and technique of filling and sealing final container: Sterile vials are filled by mechanical or manual sterile filling of the batch under constant agitation. The filled vials are covered with sterile stoppers, mechanically or manually, and are sealed with aluminum closures.

Amount of antigenic material per dose in final container: Each dose will contain no less than the following organisms:

B. burgdorferi isolate C-1-11—5×10$^8$ organisms/ml.
B. burgdorferi isolate S-1-10—5×10$^8$ organisms/ml.

Example 3

Testing of the Bacterin

Purity: Each serial or subserial is tested for bacteria and fungi in accordance with 9 C.F.R. §113.26.

Safety: Safety testing is conducted on bulk or final containers in accordance with 9 C.F.R. §§113.38 and 113.40 wherein a dog saftey test is conducted using a 2×(2 cc) dose given by IM injection.

Potency: Potency testing is conducted on assembled bulk or final containers. Potency testing is conducted using an antigen capture ELISA. Satisfactory serials must have a relative potency of $\geq 1.0$ as determine by the U.S. Department of Agriculture, Veterinary Biologics Program's Relative Potency Calculations Software, Version 3.0.

Example 4

Post-preparatory Steps

Form and size of final containers in which the product is to be distributed: The bacterin is marketed in a 2.0 ml, one dose (one dose—1.0 ml) vial. Final container labeling shall be complete.

Collection, storage, and submission of representative samples: Representative samples of each serial or subserial shall be collected for APHIS-USDA in accordance with 9 C.F.R. §113.3 by an authorized firm sampler.

Expiration date of the product: The expiration date assigned to the product shall be 24 months from the initiation of satisfactory potency testing in accordance with 9 C.F.R. §114.13. Dating will be confirmed in accordance with 9 C.F.R. §114.13.

Use, dosage, and route of administration for each animal species: The bacterin is recommended for the vaccination of healthy dogs against disease caused by *B. burgdorferi*. Each dose is 1.0 ml (1.0 cc). Vaccinate healthy dogs at 12 weeks of age or older with two doses, two to three weeks apart. Puppies under 6 weeks of age should be revaccinated every 2 to 3 weeks until they are at least 12 weeks of age. Annual revaccination with one dose is recommended. The route of administration is via intramuscular injection.

Example 5

Preparation of Barbour Stoenner Kelly (BSK) Medium

Composition: The medium is used for the growth of Borrelia cultures for use in bacterins. After detergent cleaning, all glassware is rinsed thoroughly with deionized water and then autoclaved. All ingredients are added slowly in the order listed with constant slow agitation. The base medium is prepared as follows:

| Ingredients: | Amount |
| --- | --- |
| 1) Deionized water | 500.00 ml |
| 2) HEPES | 4.60 gm |
| 3) Neopeptone | 3.83 gm |
| 4) Sodium citrate | 0.54 gm |
| 5) Glucose | 3.83 gm |
| 6) Sodium bicarbonate | 1.69 gm |
| 7) TC Yeastolate | 1.92 gm |
| 8) Pyruvic acid, sodium salt | 0.61 gm |
| 9) N-acetyl qlucosamine | 0.31 gm |

The solution is stirred slowly to dissolve all components. Add 76.70 ml of 10×CMRL 1066 without glutamine to the mixture with constant, slow agitation.

Complete medium assembly: For 10.0 ml tube or 200.0 ml bottle cultures the following ingredients are added slowly with constant agitation to the base medium:

| Ingredients: | Amount/Liter |
| --- | --- |
| 1) Sterile, heat inactivated, Rabbit Serum (The sterile rabbit serum is heated for 30 minutes at 58.5° C. +/− 0.5° C.) | 49.00 ml |
| 2) Bovine Serum Albumin | 38.34 gm |
| 3) Adjust pH to 7.3 ± 0.1 with 2N NaOH. Quantity sufficient (QS) to 800 ml with room temperature deionized water. Sterilize the mixture using a low protein binding 0.2 micron filter. | |
| 4) Sterile gelatin | 200.00 ml |

The sterile gelatin is prepared by adding 10.74 μm of gelatin to 200.0 ml deionized water. The suspension is autoclaved for 30 minutes at 121±2° C. or when a probe in the liquid reaches >119° C. for not less than 20 minutes. The solution is cooled to at least 450° C.±2° C. prior to addition to the base medium.

For 10 liter jug cultures, 100 liter fermentations or more, the following ingredients are added slowly with constant agitation to the base medium:

| Ingredients: | Amount/Liter |
| --- | --- |
| 1) Sterile, heat inactivated, rabbit serum (The sterile rabbit serum is heated for 30 minutes at 58.5° C. +/− 0.5° C.) | 49.00 ml |
| 2) Bovine Serum Albumin | 38.34 gm |

Adjust pH to 7.3+0.1 with 2N NaOH. QS to one liter with deionized water. Sterilize the mixture using a low protein binding 0.2 micron filter.

Ingredient Information:

1. Bovine Serum Albumin (BSA): The BSA powder is purchased from a commercial supplier. The BSA powder used in production may be tested in accordance with 9 C.F.R. §§ 113.50 and 113.53 and approved for use. The BSA powder may be gamma-irradiated at no less than 2.7 megarads in lieu of such testing.

2. Rabbit serum: The rabbit serum is purchased from a commercial supplier. The rabbit serum used in production may be tested in accordance with 9 C.F.R. §§113.50 and 113.53 and approved for use. The rabbit serum may be gamma-irradiated at no less than 2.7 megarads in lieu of 9 C.F.R. §§113.50 and 113.53 testing.

All chemical components will be U.S.P., or equivalent.

Testing: The medium is considered sterile, and is not tested.

Storage and use: The sterile medium is stored at 4° C. to 30° C. until used. The medium may be used immediately after preparation or for a period of no more than six months. The medium is used in the growth of Borrelia cultures for use in bacterin production.

Example 6

Hamster Vaccination—Serological and Challenge Study

Hamsters vaccinated with the *Borrelia burgdorferi* bacterin, inactivated by binary ethyleneimine (BEI), heat or formalin (FORM.), were bled and challenged two or three weeks, as indicated, after the one vaccination. Vaccinates were challenged with a three isolate mixture of *Borrelia burgdorferi*. Nonvaccinates were used as controls which were not innoculated with the *Borrelia burgdorferi* bacterin, but were challenged with the individual isolate, as indicated by isolate name, or with a three isolate mixture, indicated as Tri.

TABLE 1

| | Challenge two weeks after vaccination | | |
| --- | --- | --- | --- |
| Vaccinates | | | |
| Bacterin | ELISA | BA | Percent infection |
| BEI | 0.258 ± 0.070 | 56 ± 23 | 0(0/3) |
| HEAT | 0.157 ± 0.068 | 43 ± 30 | 0(0/5) |
| FORM. | 0.139 ± 0.132 | 35 ± 32 | 25(1/4) |

TABLE 1-continued

Nonvaccinates

| Challenge isolate | ELISA | BA | Percent infection |
|---|---|---|---|
| P/Bi | 0.003 ± 0.008 | 0 ± 0 | 0(0/3) |
| Wis. | 0.000 ± 0.000 | NT | 100(4/4) |
| Chi. | 0.000 ± 0.000 | NT | 100(3/3) |
| Tri. | NT | NT | 80(4/5) |

Challenge three weeks after vaccination

Vaccinates

| Bacterin | ELISA | BA | Percent infection |
|---|---|---|---|
| BEI | 0.218 ± 0.018 | 34 ± 25 | 50(2/4) |
| HEAT | 0.259 ± 0.059 | 29 ± 19 | 75(3/4) |
| FORM. | 0.384 ± 0.202 | 40 ± 18 | 100(4/4) |

Nonvaccinates

| Challenge isolate | ELISA | BA | Percent infection |
|---|---|---|---|
| P/Bi | 0.000 ± 0.000 | 4 ± 2 | 0(0/4) |
| Wis. | 0.000 ± 0.000 | NT | 50(2/4) |
| Chi. | 0.000 ± 0.000 | NT | 50(2/4) |
| Tri. | NT | NT | 67(2/3) |

BA = Borreliacidal Assay

These results presented in Table 1 show that there is not a significant (P=0.05) difference in serological response with respect to method of inactivation of *B. burgdorferi* cells at either 2 or 3 weeks post vaccination. Serological responses either decreased or increased slightly from 2 to 3 weeks post vaccination, however, protection (with respect to the C-1-11 and S-1-10 isolates) decreased for each vaccinate group at 3 weeks post vaccination. The P/Bi isolate is nonvirulent and was not found to infect tissues of vaccinates or controls.

Example 7

ELISA Studies for Nonvaccinated and Intramusculary Vaccinated Dogs

The bacterin was tested for its ability to stimulate an immune response in dogs. Dogs were either vaccinated with the bacterin provided herein (V), or were not vaccinated (NV), and their levels of antibody to the S-1-10 and C-1-11 coating antigens was determined by ELISA at three weeks after the first vaccination and two weeks after a second, subsequent vaccination, as indicated.

TABLE 2

| Group | Prevac. | Three weeks Post 1st Vac. | Two weeks Post 2nd Vac. |
|---|---|---|---|
| Coating antigen = S-1-10 | | | |
| V | 0.013 ± 0.020 | 0.672 ± 0.128 | 1.369 ± 0.167 |
| NV | 0.012 ± 0.016 | 0.027 ± 0.011 | 0.014 ± 0.015 |
| Coating antigen = C-1-11 | | | |
| V | 0.033 ± 0.015 | 0.511 ± 0.122 | 1.550 ± 0.148 |
| NV | 0.023 ± 0.019 | 0.017 ± 0.013 | 0.037 ± 0.016 |

The data show that inoculation with the bacterin of this invention results in production of antibodies against both the Wisconsin S-1-10 and the Chicago C-1-11 *B. burgdorferi* isolates. Vaccinated dogs had a higher serum level of antibodies to the S-1-10 and C-1-11 coating antigens than the nonvaccinates. These levels of antibody production were increased after an administration of a second dose of the bacterin to dogs. These results therefore show that the bacterin of this invention can stimulate animals to make anti-Borrelia antibodies which will be useful against subsequent challenge by the bacteria.

Example 8

Borreliacidal Assay Using Dog Serum

Dogs were vaccinated with the *Borrelia burgdorferi* bacterin. Serum from these dogs was isolated and mixed with a culture of growing isolate S-1-10 of *B. burgdorferi*. The percent of Borrelia killing in cultures grown in the presence, and absence, of this immune dog serum is indicated in Table 4 (see below).

TABLE 3

Borreliacidal Assay -- Dog Serum

Percent Borrelia Killing

| | Prevac. | 3 Weeks Post 1st Vac. | 2 Weeks Post 2nd Vac. |
|---|---|---|---|
| Nonvac. | 0 ± 0 | 0.5 ± 1.7 | 1.5 ± 2.7 |
| I. M. vac. | 0 ± 0 | 59.5 ± 6.3 | 87.9 ± 10.3 |
| SubQ. vac. | 0 ± 0 | 63.7 ± 20.6 | 86.1 ± 12.0 |

Nonvac.: serum from nonvaccinated dogs;
I. M. vac.: intramuscularly vaccinated dogs;
SubQ. vac.: subcutaneously vaccinated dogs;
Prevac.: serum from dogs prior to vaccination.

As can be seen from Table 3, serum isolated from, dogs prior to their vaccination with the bacterin (prevac.) and from animals not vaccinated (Nonvac.) was unable to initiate cell death in a growing Borrelia culture. By contrast, the immune dog serum was able to initiate cell death. Serum isolated from dogs vaccinated intramuscularly (I.M. vac.) with the bacterin was able to cause a similar percentage of cell death as serum isolated from subcutaneously vaccinated (SubQ. vac.) dogs. Serum isolated from dogs given a second dose of the bacterin caused a higher rate of cell death than serum from dogs vaccinated only once.

Example 9

*Borrelia burgdorferi* Isolate 297

Serum from canines prior to and following inoculation with *Borrelia burgdorferi* N-40 isolate was tested for borreliacidal antibody against cells of the 297 isolate by the Borreliacidal Assay.

TABLE 4

| | Serum Dilution | | | | | |
|---|---|---|---|---|---|---|
| Serum | 1:20 | 1:40 | 1:80 | 1:160 | 1:320 | 1:640 |
| Preinoc. Live | 140 | 158 | 173 | 133 | NC | NC |
| Preinoc. Dead | 6 | 7 | 13 | 7 | NC | NC |
| 5 Weeks Post Infection Live | 1 | 0 | 2 | 15 | 100 | 102 |
| 5 Weeks Post Infection Dead | 51 | 39 | 57 | 33 | 23 | 7 |

NC: Not Counted.

The data presented in Table 4 show that canines inoculated with *B. burgdorferi* isolate N-40 produce borreliacidal antibody against a different isolate (i.e. 297) but of the same seroprotective group as N-40, which is absent in noninoculated, *B. burgdorferi* free canines.

*Borrelia burgdorferi* Isolate N-40

Serum from canines prior to and following inoculation with *Borrelia burgdorferi* N-40 isolate was tested for borreliacidal antibody against cells of the N-40 isolate by the Borreliacidal Assay.

TABLE 5

| Serum | Serum Dilution | | | | | |
|---|---|---|---|---|---|---|
| | 1:20 | 1:40 | 1:80 | 1:160 | 1:320 | 1:640 |
| Preinoc. Live | 154 | 226 | 204 | 219 | 280 | 135 |
| Preinoc. Dead | 0 | 9 | 6 | 5 | 5 | 3 |
| 5 Weeks Post Infection Live | 0 | 0 | 3 | 1 | 138 | 99 |
| 5 Weeks Post Infection Dead | 54 | 65 | 72 | 48 | 3 | 5 |

The data presented in Table 5 show that canines, inoculated with *B. burgdorferi* N-40 isolate, produce borreliacidal antibody to the inoculated isolate which is absent in noninoculated, *B. burgdorferi* free dogs.

Example 10

In Vitro Cross-protection Studies

Table 6 (see below) indicates the natural hosts of the various isolates of *Borrelia burgdorferi* used in the in vitro crossprotection studies, the source of the isolates in the host animals and the geographic locations in which the strains were isolated.

TABLE 6

*Borrelia burgdorferi* Isolates

| Name | Host | Source | Location |
|---|---|---|---|
| 297 | Human | CSF | Eastern US |
| B31 | *I. dammini* | — | Eastern US |
| S-1-10 | *P. leucopus* | kidney | Wisconsin |
| IPT | *I. pacificus* | — | W. Coast US |
| MMTI | *I. dammini* | — | Minnesota |
| 35211 | *I. ricinus* | — | Switzerland |
| Chicago (C-1-11) | *M. pennsylvanicus* | kidney | Illinois |
| PBi | Human | CSF | Germany |
| G25 | *I. ricinus* | — | Sweden |

CSF: cerebrospinal fluid.

Hamsters were inoculated with a live form of one of the isolates indicated in the first vertical column of Table 7. Antiserum was isolated from these hamsters and added to cultures of the *B. burgdorferi* isolates indicated in the horizontal row of Table 7. The degree to which the antibody recognized the bacteria in the culture and hence, the degree to which cell death was caused, was measured as follows. Serum from hamsters infected with individual isolates of live *Borrelia burgdorferi* was isolated, diluted in BSK medium, heat inactivated and 100 µl was added to each reaction tube. Ten µl of complement was also added. Culture density was then adjusted to a concentration of $10^5$ cells per ml, and 100 µl of the culture was then added to each reaction tube. The resultant antibody/*B. burgdorferi* reaction tubes were incubated at 32° C. for two hours, and 800 µl of fresh BSK medium was then added. The reaction tubes were then incubated at 32° C. for four days, after which viability was assessed as the percent of intact cells, determined by Coulter counter. Results of the in vitro crossprotection studies are shown in Table 7, below.

TABLE 7

IN VITRO CROSS-PROTECTION STUDIES

| Antisera | 297 | B31 | S-1-10 |
|---|---|---|---|
| BSK | 100.0 ± 3.0 | 100.0 ± 5.8 | 100.0 ± 3.5 |
| NHS | 100.0 ± 3.8 | 107.9 ± 7.9 | 99.5 ± 3.5 |
| 297 | 0.6 ± 0.2 | 0.9 ± 0.0 | 1.0 ± 0.2 |
| B31 | 0.5 ± 0.1 | 0.9 ± 0.2 | 0.9 ± 0.1 |
| S-1-10 | 0.3 ± 0.1 | 0.7 ± 0.1 | 0.8 ± 0.1 |
| 35211 | 0.3 ± 0.1 | 0.7 ± 0.1 | 1.0 ± 0.1 |
| MMTI | 2.4 ± 1.6 | 0.5 ± 0.0 | 1.0 ± 0.0 |
| IPT | 0.4 ± 0.1 | 3.3 ± 0.1 | 0.9 ± 0.0 |
| Chicago | 32.6 ± 1.7 | 55.7 ± 3.8 | 91.2 ± 7.3 |
| PBi | 93.5 ± 2.8 | 97.5 ± 10.9 | 103.5 ± 5.2 |
| G25 | 103.5 ± 5.3 | 113.5 ± 8.0 | 97.1 ± 8.9 |

| Antisera | 35211 | MMTI | IPT |
|---|---|---|---|
| BSK | 100.0 ± 7.7 | 100.0 ± 12.4 | 100.0 ± 9.0 |
| NHS | 99.5 ± 3.5 | 103.9 ± 4.1 | 108.9 ± 1.4 |
| 297 | 1.0 ± 0.2 | 2.5 ± 0.4 | 0.3 ± 0.0 |
| B31 | 0.9 ± 0.1 | 11.0 ± 1.0 | 0.4 ± 0.0 |
| S-1-10 | 0.8 ± 0.1 | 0.7 ± 0.3 | 0.3 ± 0.1 |
| 35211 | 1.0 ± 0.1 | 1.7 ± 0.3 | 0.3 ± 0.0 |
| MMTI | 1.0 ± 0.0 | 0.9 ± 0.2 | 0.2 ± 0.0 |
| IPT | 0.9 ± 0.0 | 1.9 ± 0.2 | 0.2 ± 0.0 |
| Chicago | 91.2 ± 7.3 | 84.7 ± 5.4 | 100.5 ± 2.8 |
| PBi | 103.5 ± 5.2 | 104.2 ± 13.4 | 96.2 ± 3.6 |
| G25 | 97.1 ± 8.9 | 106.4 ± 13.2 | 106.3 ± 9.6 |

| Antisera | Chicago | PBi | G25 |
|---|---|---|---|
| BSK | 100.0 ± 3.5 | 100.0 ± 8.0 | 100.0 ± 7.2 |
| NHS | 111.2 ± 14.5 | 105.7 ± 7.8 | 104.4 ± 5.8 |
| 297 | 99.2 ± 3.6 | 113.4 ± 3.0 | 91.5 ± 2.9 |
| B31 | 114.2 ± 6.7 | 108.9 ± 8.9 | 96.4 ± 8.9 |
| S-1-10 | 99.5 ± 7.3 | 85.1 ± 6.6 | 90.7 ± 6.4 |
| 35211 | 107.3 ± 11.4 | 102.1 ± 3.8 | 92.2 ± 3.8 |
| MMTI | 102.5 ± 8.5 | 108.7 ± 9.1 | 96.5 ± 6.0 |
| IPT | 109.5 ± 8.5 | 119.5 ± 8.0 | 97.1 ± 6.8 |
| Chicago | 0.8 ± 0.1 | 93.6 ± 3.6 | 105.2 ± 8.2 |
| PBi | 114.8 ± 11.4 | 0.2 ± 0.0 | 0.3 ± 0.0 |
| G25 | 115.7 ± 0.4 | 0.2 ± 0.0 | 0.3 ± 0.0 |

BSK: Barbour Stoenner Kelly medium;
NHS: normal hamster serium, i.e., serum which does not contain anti-Borrella antibodies.

Viability values in Table 7 are expressed as the percentage of cell viability in a culture compared to 100% viability of "BSK" controls. BSK control cultures are those cultures which are contacted with Barbour Stoenner Kelly medium instead of antiserum from hamsters inoculated with a *B. burgdorferi* isolate. Hence, these cultures should not experience cell death due to antibody reactions. Accordingly, viability of these cultures is set at 100% compared to cultures to which antiserum has been added. Low viability of a culture compared with the control values indicates that death has occurred in the culture, resulting from antibody reactions with cell surface determinants.

The data in Table 7 show that cultures of an isolate contacted with antiserum from a hamster inoculated with the same isolate exhibit low viability; that is, antibodies synthesized against the inoculated isolate recognize the isolate in culture and, together with complement, cause cell death. For example, a *B. burgdorferi* 297 culture contacted with BSK medium or NHS, i.e., serum which doesn't contain anti-Borrelia antibodies, exhibited 100% viability. However, a 297 culture contacted with antiserum from a 297-inoculated hamster exhibited 0.6% viability. Furthermore, a *B. burgdorferi* Chicago culture contacted with NHS had 111% viability while a Chicago culture contacted with anti-Chicago antiserum exhibited 0.8% viability.

The data in Table 7, also show that antiserum from hamsters inoculated with one isolate induced cell death in cultures of some of other isolates. As discussed above, viability of cultures contacted with BSK medium is set at 100%. The data show that the viability of cultures contacted with normal hamster serum (NHS) is also about 100%, as expected. However, cultures of the first six *B. burgdorferi* isolates listed, i.e., 297, B31, S-1-10, 35211, MMTI and IPT, when contacted with antiserum obtained from hamsters inoculated with any one of the same six isolates all exhibited viability values significantly lower than the controls. The data shows that culture viability was low when antiserum against an isolate was added to cultures of the same isolate. Culture viability was low when the cultures were contacted with antisera directed against other isolates. For example, anti-297 antisera was added to 297, B31, S-1-10, 35211, MMTI and IPT cultures. Culture viability was 0.6%, 0.9%, 1.0%, 1.0%, 2.5% and 0.3%, respectively, indicating that the antibodies had recognized and reacted with determinants on these isolates.

The data in Table 7 therefore shows that 297, B31, S-1-10, 35211, MMTI and IPT isolates are crossprotective. That is, as discussed above, antibodies against one isolate recognize and react with surface determinants on other isolates. These isolates therefore are members of the same seroprotective group. This group is known as the seroprotective group A of *Borrelia burgdorferi* isolates.

Antisera from Chicago, PBi and G25-inoculated hamsters did not induce cell death in cultures of these isolates and therefore, belong to one or more different seroprotective groups. Anti-Chicago antisera did not induce a significant degree of cell death in cultures of any of the other isolates tested. Accordingly, the Chicago strain (also designated C-1-11) is the only strain tested belonging to seroprotective group B.

Anti-PBi antiserum induced cell death in cultures of both PBi and G25, as did anti-G25 -antiserum. Therefore, PBi and G25 are crossprotective isolates classified in the same seroprotective group, the "European group of *Borrelia burgdorferi* isolates.

Thus, the results of crossprotection studies shown in Table 7 indicate that *Borrelia burgdorferi* isolates can be classified into at least three distinct seroprotective groups.

Example 11

Hamster vaccination—serological and challenge study

Figure 3:
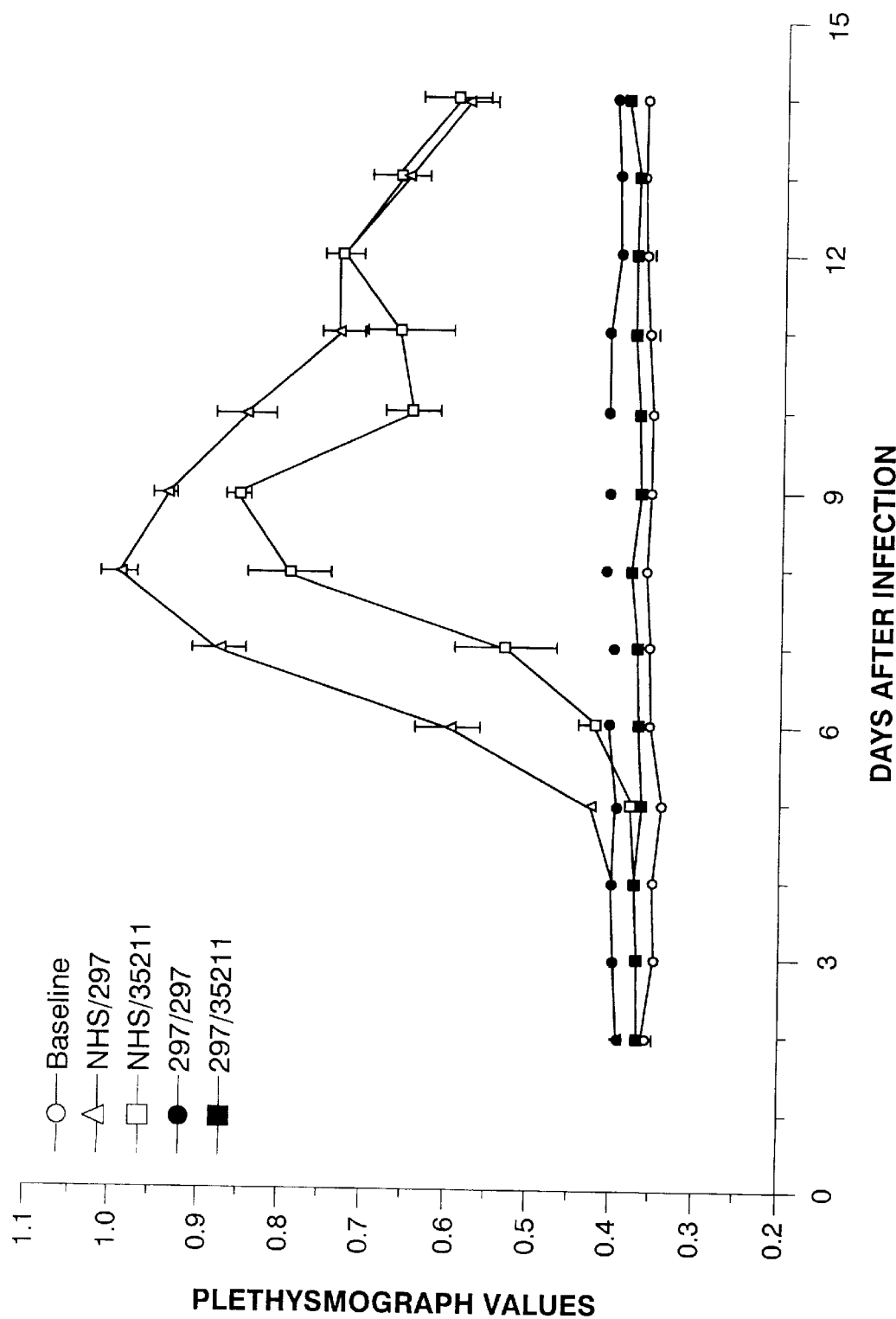
FIG. 3. Plethysmograph values showing mercury displacement by the paws of control and vaccinated hamsters. Hamsters were inoculated with either normal hamster serum (NHS) or serum from hamsters which had themselves been inoculated with the indicated *B. burgdorferi* (297 or 35211) isolate. The vertical axis shows mercury displacement in mm of Hg. The horizontal axis indicates the number of days post infection at which mercury displacement was measured. Open circles=baseline values corresponding to non-inoculated and unchallenged hamsters; closed circles= hamsters inoculated with antisera from hamsters inoculated with a live *B. burgdorferi* 297 isolate and then challenged with the 297 isolate; closed squares=hamsters inoculated with anti-297 antisera and challenged with the 35211 isolate; open squares=hamsters inoculated with normal hamster serum and challenged with the 35211 isolate; and closed triangles=hamsters inoculated with normal hamster serum and challenged with the 297 isolate.

Hamsters were inoculated with live *Borrelia burgdorferi* of the 297 isolate. Serum from these hamsters, or from normal, i.e. noninoculated hamsters or normal hamster serum (NHS), was then administered to other hamsters. These hamsters were then challenged with either the 297 or 35211 (Swiss) strains as indicated in FIG. 3. The antisera was evaluated for its ability to transfer passive immunity in recipient hamsters against *B. burgdorferi* infection, at successive days post-infection, as indicated.

FIG. 3 shows the results of the serological and challenge study. Protection against *B. burgdorferi* infection was assessed as plethysmograph values of challenged animals in comparison to baseline values for control, i.e., noninoculated, animals. The plethysmograph measures the amount of mercury displaced by the paws of a hamster. As discussed above, one of the symptoms resulting from *B. burgdorferi* infection is arthritis and swelling. Accordingly, hamsters infected with Borrelia should have swollen paws displacing larger amounts of mercury than the paws of normal hamsters. Hamsters-protected from *B. burgdorferi* infection should not exhibit swollen paws. Therefore, an increase in the size of an infected hamster's paw, i.e., an increase in the amount of mercury displaced, indicates that the hamster was not protected by the administered antisera from *B. burgdorferi* challenge.

The results shown in FIG. 3 indicate that normal hamster serum (NHS), as expected, did not protect hamsters against infection by *B. burgdorferi* isolate 297 (the plethysmograph value of the NHS-inoculated/297-challenged hamster increased to a peak of approximately 1.0 mm Hg eight days post challenge in comparison to the baseline value of approximately 0.35). Normal hamster serum also did not protect hamsters against infection by *B. burgdorferi* isolate 35211 (the plethysmograph value of the NHS-inoculated/ 35211 challenged hamster increased to a peak of approximately 0.85 mm Hg nine days post infection, in comparison to the baseline value).

By contrast, FIG. 3 indicates that anti-297 antiserum protected hamsters against subsequent challenge with the 35211 isolate. The plethysmograph values of the 297-inoculated/35211-challenged hamster were approximately the same as the baseline value from two to fourteen days post challenge. These results confirm the in vitro studies which demonstrated that *Borrelia burgdorferi* isolates can be crossprotective, i.e., that antibodies against one isolate can confer passive immunity against another isolate. The results indicate that the 297 and 35211 isolates are crossprotective and therefore belong to the same seroprotective group.

Example 12

Summary of *Borrelia burgdorferi* Isolates

Forty three individual isolates of *B. burgdorferi* from the United States and Europe were examined. Exponentially growing cultures of the individual isolates were incubated with antisera to the *Borrelia burgdorferi* isolate 297 from seroprotective group A, isolate PBi from seroprotective group C and an isolate C-1-11 from seroprotective group B.

TABLE 8

| Antisera | | | Isolates | | |
|---|---|---|---|---|---|
| "A" | "C" | "B" | | | |
| anti-297 | anti-PBi | anti-Chicago | US | European | Total |
| S | R | P | 15 | 1 | 16 |
| R | S | R | 0 | 13 | 13 |
| R | R | S | 1 | 0 | 1 |
| S | R | S | 3 | 3 | 6 |
| S | S | S | 1 | 0 | 1 |
| R | R | R | 0 | 6 | 6 |
| | | | | | 43 |

S: Sensitive to killing;
R: Resistant to killing;
P: Partial killing.

Sensitivity (S) to killing induced by anti-297 antisera, but not by anti-PBi or anti-Chicago antisera, indicates that a *Borrelia burgdorferi* isolate is classified in the same seroprotective group, i.e., the seroprotective group A, as the 297 isolate. Resistance (R) to killing induced by anti-297 antiserum indicates that an isolate should be classified in a distinct seroprotective group. Table 8 indicates that 15 of the 16 isolates classified in seroprotective group A were isolated in the U.S. Table 8 also indicates that 13 of the 13 isolates sensitive to killing only by anti-PBi antisera, and therefore classified in seroprotective group C, were isolated in Europe. Table 8 further shows that 6 of the 43 isolates were resistant to killing by anti-297, anti-PBi and anti-Chicago antisera, i.e., that the antibodies did not recognize the cell surface determinants expressed by these strains. Accordingly, these six isolates were not crossprotective with any of the other isolates tested. The data therefore demonstrate that there is at least one more seroprotective group of B. burgdorferi isolates in addition to seroprotective groups A, B or C.

Example 13

Natural Tick Challenge Using Bivalent Vaccine Composition

Introduction

Lyme disease, caused by the spirochete Borrelia burgdorferi (Bb) and transmitted by Ixodes ticks, is a multisystemic disease that can affect the skin, nervous system, heart, and joints of unprotected humans and canines. (Anderson, J. F., et al. (1988) J. Clin. Microbiol. 26: 2209–2212; Appel, et al. (1993) J. Inf. Dis. 167: 651–664; Lane, R. S. et al. (1989) J. Clin. Microbiol. 27: 2344–2349; LeFebvre, R. B. et al. (1990) J. Clin. Microbiol. 28: 700–707; Levy, S. A. et al. (1992) Canine Practice 17: 5–14; Nelson, J. A., et al. (1991) J. Clin. Microbiol. 29: 1732–1734; Piesman, J. et al. (1990) Am. J. Trop. Med. Hyg. 42: 352–357; Steere, A. C., et al. (1983) N. Engl. J. Med. 308: 733–740; Steere, A. C., et al. (1977) Ann. Intern Med. 86: 685–698). Although antibiotic therapy can be effective, it must be administered early in the disease. Antibiotics administered during later stages of the disease may not be effective in complete elimination of the organism from the host. Hamsters or mice vaccinated with experimental bacterins containing inactivated whole cells or subunit antigens, develop an immune response that will protect against either artificial or natural routes of infection. (Fikrig, E., et al. (1990) Science 250: 553–556; Fikrig, E., et al. (1992) Proc. Natl. Acad. Sci. 89: 5418–5421; Johnson, R. C. et al. (1986) Immun. 54: 89.7–898; Johnson, R. C. et al. (1986) Zbl. Bakt. Hyg. A. 263: 45–48; Kochi, S. K. et al. (1988) Infect. and Immun. 56: 314–321; Schmitz, J. L. et al. (1991) Infect. and Immun. 59: 3815–3818). More recently a commercially available vaccine has been shown to be efficacious against laboratory and field challenge. (Hsien-Jue, C., L. G. Chavez, Jr., B. M. Blumer, R. W. Sebring, T. L. Wasmoen, and W. M. Acree. (1992) JAVMA 201: 403–411) Although vaccines provide protection, it is important that immunity (borreliacidal antibody) be present prior to infection since infected animals can remain infected despite the presence of circulating borreliacidal antibody (Callister, S. M. et al. (1991) J. Clin. Microbiol. 29: 1773–1776; Johnson, R. C. et al. (1986) Immun. 54: 897–898; Johnson, R. C. et al.(1986) Zbl. Bakt. Hyg. A. 263: 45–48; Kochi, S. K. et al. (1988) Infect. and Immun. 56: 314–321; Schmitz, J. L. et al. (1991) Infect. and Immun. 59: 3815–3818).

Different seroprotective groups of Bb have been characterized by passive protection studies in hamsters and an in vitro test (Borreliacidal Assay) that can differentiate between seroprotective groups based on antibody response following infection (Lovrich S. D. et al. (1993) Infect. and Immun. 61:4367–4374). Antibody produced against an isolate of one seroprotective group may not provide protection in the canine, or other species, against exposure to an isolate of a different seropositive group. Therefore, it is necessary to incorporate isolates representing different seroprotective groups to assure a broadly efficacious vaccine.

Ixodes scapularis ticks infected with Bb can infect mice or dogs when placed on the animals and allowed to feed. (Appel, Max J. G. et al. (1993) J. Inf. Dis. 167: 651–664; Fikrig, E. et al. (1992) Proc. Natl. Acad. Sci. 89: 5418–5421; Rowhrig, J. T. et al. (1992) Journ. Immunol. 149: 3648–3653) The immune response of dogs to Bb by needle inoculation is different than by tick transmission (Rowhrig, J. T. et al. (1992) Journ. Immunol. 149: 3648–3653). For this reason we have evaluated the immunogenicity of a bivalent vaccine against a natural tick challenge.

I. Materials and Methods

A. Animals

Four (4) B. burgdorferi (Bb)-free beagles, greater than 21 weeks of age, from Solvay Animal Health, Inc., Charles City, Iowa., were used in a tick challenge model test. Thirty (30) 5 to 16-week-of-age, Bb-free beagles, from Harlan Sprague Dawley, Indianapolis, Ind., were used in the immunogenicity test (19 vaccinates and 9 nonvaccinates). Dogs were determined to be Bb-free by serological tests and culture of blood in Barbour Stoenner Kelly (BSK) medium.

B. Bacterin Preparation

The bacterin was prepared as described above. The bacterin was prepared with two isolates, C-1-11 and S-1-10, passed 8 times (X+8 passage level) from the master used.

C. Vaccination

Nineteen dogs were vaccinated per label instructions:
1. The vaccine was allowed to warm to room temperature.
2. The vial was gently shaken prior to aseptically withdrawing contents.
3. One dose (1.0 ml) was given intramuscularly in the caudal thigh. The initial dose was given at 5 to 16 weeks of age. The second dose was given three weeks following the initial vaccination.

Dogs were visually observed for abnormal reactions to vaccination.

D. Challenge

Ixodes scapularis male and female ticks were collected from two Lyme disease endemic areas of Wisconsin (rural areas near Hixton and Ettrick, Wis.). The midguts of 50 and 48 male I. scapularis ticks from Hixton and Ettrick, Wis. respectively were examined by fluorescent antibody assay (FA) specific for Bb. Ticks from these collections were pooled and used for both the challenge model and immunogenicity tests.

1. B. burgdorferi Detection by Immunofluorescence Using Monoclonal Antibody.
   a) Specimen Preparation:
      i. Tick—The head was removed using a scalpel. The midgut was expressed from the tick and smeared on a microscope slide using an applicator stick and the smear was thoroughly dried.
      ii. Culture—The cultured spirochetes were concentrated by centrifugation (13,000×g, room temperature) and washed in 0.01M PBS pH 7.2. Fifteen microliters of the washed suspension was placed on a microscope slide and thoroughly dried.
   b) Dried slides were fixed in acetone for 10 minutes and allowed to dry.
   c) Mouse monoclonal antibody, H5332 (initially obtained from Alan Barbour, University of Texas, San Antonio), was diluted 1:40 using PBS and applied to the slide. Slides were incubated 30 minutes at 37° C. in a moist chamber.
   d) After incubation slides were rinsed with a stream of PBS and soaked for 5 to 10 minutes in a coplan jar containing PBS.

e) Slides were then reacted with an anti-mouse IgG-FITC labeled conjugate diluted 1:400 with PBS. Slides were incubated 30 minutes at 37° C. in a moist chamber.

f) After incubation slides were rinsed with a stream of PBS and soaked for 5 to 10 minutes in a coplan jar containing PBS and slides were blotted dry with bibulous paper.

g) Buffered glycerol and a cover slip were placed on the slides and viewed by fluorescent microscopy.

E. Challenge Methods

1. Challenge Model Test. To establish method of attachment and infection, 4 female and 1 or 2 male ticks were placed on a shaved area on each side of the thorax of each of 4 dogs. Females were placed on the dogs to feed, males were present to promote complete feeding by the females (Appel, Max J. G. et al. (1993) J. Inf. Dis. 167: 651–664). Ticks were allowed to feed for 1 week, collected if possible, and examined for the presence of Bb. Skin biopsies were collected from the left side attachment site one week following attachment and from the right side two weeks following attachment.

2. Immunogenicty Test. Four female ticks and one male tick were placed on a shaved area located on the right side of each vaccinate and nonvaccinate one week post second vaccination. The ticks were allowed to feed for 9 days, collected if possible, and examined for the presence of Bb. Fourteen to 15 days following tick attachment, skin biopsies were collected from the tick attachment site and from a site approximately 15 cm from the attachment site.

F. Skin Biopsies

Skin biopsy sites were shaved, washed with Solvahex™ Surgical Scrub, and rinsed thoroughly with sterile water to remove residual disinfectant. Skin biopsies were taken by making elliptical incisions through the dermal and subcutaneous skin layers. A skin biopsy was subdivided into sections which were each placed in 9.0 ml of fresh BSK medium. The samples were homogenized and 1.0 ml was placed in fresh BSK medium containing agarose without or with rifampin (40 micrograms per ml). Cultures were incubated at 32° C. for 6 weeks and were examined periodically for the presence of spirochetes. Spirochete positive cultures were confirmed as Bb by FA. After 6 weeks of incubation, negative cultures were passed to fresh BSK medium by inoculating 1.0 ml of negative culture into 9.0 ml of fresh BSK medium containing agarose and rifampin (40 micrograms per ml). These cultures were incubated at 32° C. for 6 weeks and examined as described above.

G. Blood (Challenge Model and Immunogenicity Tests)

Blood was collected in sodium citrate tubes at the time of tick attachment and weekly following tick attachment. For each sample 3.0 mls of blood from each dog was placed in 27.0 mls of fresh BSK medium. Blood cultures were further diluted 1:100 and 1:1000 using 9.0 ml BSK blanks. The cultures were incubated at 32° C. for at least 3 weeks and examined as described above. Spirochete positive cultures were confirmed as Bb by FA.

H. Serology

1. Challenge Model Test

Blood was collected at time of tick attachment and weekly following tick attachment. Borreliacidal assays and ELISA tests were run on serum from blood samples collected.

2. Immunogenicity Test

Blood was collected at time of first and second vaccinations, at tick attachment, and weekly following tick attachment. Serum was separated and BA tests were run on samples collected at week 0, 4, 9, and 10. ELISA tests were run on samples collected at week 0, 3, 4, 5, 6, 8, 9, and 10.

I. Borreliacidal Assay Procedure a) A 72 hour culture of either *B. burgdorferi* (Bb) isolate C-1-11 or S-1-10 was quantitated by Petrof f/Hauser chamber and diluted to $1 \times 10^5$ cells per ml with fresh BSK medium.

b) Serum to be tested was diluted 1:20 in fresh BSK medium, filtered through a 0.2 micron filter, and heat inactivated at 56° C. for 45 minutes.

c) To conduct the test, 100 $\mu$l, of the diluted culture and 100 $\mu$l of the diluted, filtered, and heat inactivated serum was added to a 1.5 ml screw cap tube. Fifteen (15) $\mu$l of guinea. pig complement was added to the same tube. The contents were mixed and incubated at 32° C. for 2 hours.

d) Following the 2 hour incubation period, 800 $\mu$l of fresh BSK medium was added to the tube. The tube was further incubated at 32° C. for 5 to 7 days.

e) After 5 to 7 days incubation, growth of Bb was determined by removing a 300 to 600 $\mu$l sample from the reaction tube and placing the sample in a vial containing 10.0 ml of 2.0% saline. Bb in the diluted sample was counted using a Coulter Counter (Model ZBi). The percent kill was determined by the following equation:

$$\text{Pct. Kill} = 100 - \left[ \frac{\text{Mean Test Serum Cell Count}}{\text{Mean Neg Serum Cell Count}} \times 100 \right]$$

J. ELISA Procedure

1. Preparation of whole cell antigen:

a) *Borrelia burgdorferi* isolates C-1-11 or S-1-10 were grown in Barbour Stoenner Kelly (BSK) medium to late log phase (approximately $2 \times 10^8$ cells per ml) and inactivated with binary ethyleneimine.

b) The cells were washed in sterile saline (0.85% NaCl, ph 7.1±0.2) three times.

c) Total protein was determined by a commercially available kit.

2. Test Protocol:

a) IMMULON 3 plates were coated with either C-1-11 or S-1-10 whole cell antigen (0.3 micrograms whole cell antigen in 100 microliters of carbonate coating buffer per well). Plates were incubated at 4° C. for 15 to 17 hours in a humid chamber.

b) Contents of each plate (whole cell antigen solution) were removed and 5% (W/V) powdered milk solution was added to each well (400 microliters per well). Plates were incubated at 37° C. for 60 minutes in a humid chamber.

c) Contents of each plate (5% powdered milk solution) were removed and plates were allowed to dry for 30 minutes. (At this point plates were stored at 4° C. or used immediately.)

(d) Serum samples were diluted 1:200 in 0.1M PBS pH 7.2, 0.05% TWEEN-20 and tested in duplicate by adding 50 microliters of the diluted serum to each of two wells. Positive and negative control serum samples were also tested in duplicate on each plate. Plates were incubated at 37° C. for 60 minutes.

(e) Contents of each plate (serum sample dilutions) were removed and plates were washed three times with a 0.9% NaCl, 0.05% TWEEN-20 solution.

(f) Peroxidase labeled goat anti dog IgG (heavy and light chains) conjugate diluted 1:1500 in 0.01M PBS pH 7.2, 0.05% TWEEN-20 was added to each well (50 microliters per well). Plates were incubated at 37° C. for 60 minutes in humid chamber.

g) Contents of each plate (conjugate solution) were removed and plates were washed as in step 6 above.

h) The substrate O-Phenylenediamine (30.0 mg) was dissolved in a 0.051M dibasic sodium phosphate, 0.0224M citric acid, 0.012% hydrogen peroxide solution (74.83 ml) and added to each well (100 microliters per well). The substrate was allowed to react for 8 to 10 minutes.

i) The substrate reaction was stopped with 50 microliters per well of 2N sulfuric acid. The optical density of each well was read at 490 nm. Mean optical density values of test wells were normalized against the mean optical density values of the positive control (i.e. mean optical density value of test wells of a serum sample tested were divided by the mean optical density value of test wells of a serum sample tested were divided by the mean optical density values of the positive control).

K. Clinical Signs

Following challenge all dogs were observed for clinical signs such as fever, lethargy, lameness, and inappetence.

L. Statistical Analysis

Skin biopsy culture results were compared by the Fisher's Exact test.

II. RESULTS

A. Vaccination

There were no abnormal reactions to vaccination.

B. Ticks

The FA tested sample of male ticks collected from Hixton and Ettrick were found to be 52% and 54% infected respectively.

C. Challenge Model Test

Ticks attached in 1 to 2 hours. After 2 days ticks were engorged. Three days later most dogs had dislodged the attached ticks, however, three engorged ticks were collected from one of the four dogs (#450). Bb were cultured from the blood removed from the hemocoele from 1 of the 3 ticks and the midgut of the same tick was Bb positive by FA. Skin biopsies taken from the attachment site of this dog 1 week after attachment were not positive for Bb. In fact one week after tick attachment spirochetes were recovered from skin biopsies of only one dog (Table 9). In contrast, two weeks after tick attachment spirochetes were recovered from skin biopsies collected from the opposite side of all 4 dogs (Table 9). Dogs were spirochetemic 2 and 9 weeks after tick attachment (Table 10). Borreliacidal antibody was detectable and increased tat 10 and 11 weeks following tick attachment (Table 11. Antibodies were detected to both C-1-11 and S-1-10 antigens as measured by ELISA after tick attachment (Table 12).

TABLE 9

Challenge Model Test: *B. burgdoferi* cultured from skin biopsy samples taken from the tick attachment site one and two weeks after tick attachment.

| | Skin Biopsy Cultures | |
|---|---|---|
| Dog No. | One Wk. Post Attachment | Two Wks. Post Attachment |
| 450 | 0/5[a] | 3/3 |
| 400 | 4/5 | 2/4 |

TABLE 9-continued

Challenge Model Test: *B. burgdoferi* cultured from skin biopsy samples taken from the tick attachment site one and two weeks after tick attachment.

| | Skin Biopsy Cultures | |
|---|---|---|
| Dog No. | One Wk. Post Attachment | Two Wks. Post Attachment |
| 402 | 0/5 | 4/4 |
| R | C[b] | 2/2 |

[a]Samples positive per number tested.
[b]Contaminated.

TABLE 10

Challenge Model Test: *B. burgdorferi* cultured from blood collected from dogs after tick attachment.

| | Blood Cultures Weeks Post Attachment | | | | | | | |
|---|---|---|---|---|---|---|---|---|
| Dog No. | 1 | 2 | 9 | 10 | 11 | 12 | 13 | 14 |
| 450 | − | + | − | − | − | − | − | − |
| 400 | − | + | + | − | − | − | − | − |
| 402 | − | + | − | − | − | − | − | − |
| R | − | + | − | − | − | − | − | − |

+ (Growth)
− (No Growth)

TABLE 11

Challenge Model Test: Borreliacidal Assay values (means ± s.d. percent kill of four dogs) against C-1-11 and S-1-10 following tick attachment.

| | Borreliacidal Assay Mean Percent Kill Weeks Post Attachment[a] | | | | | |
|---|---|---|---|---|---|---|
| Isolate | 0 | 1 | 2 | 9 | 10 | 11 |
| C-1-11 | 6 ± 4 | 6 ± 4 | 6 ± 6 | 2 ± 3 | 14 ± 10[b] | 21 ± 9[b] |
| S-1-10 | 2 ± 2 | 5 ± 5 | 1 ± 1 | 7 ± 13[b] | 13 ± 17[b] | 20 ± 18[b] |

[a]BA testing for weeks 12 to 16 is in progress.
[b]Standard deviations were high due to negative BA responses in some dogs.

TABLE 12

Challenge Model Test: Antibody detected against S-1-10 and C-1-11 antigens as measured by ELISA following tick attachment.
ELISA Mean Optical Density Values Weeks Post Attachment

| | 9 | 10 | 11 | 12 | 13 | 14 | 15 | 16 |
|---|---|---|---|---|---|---|---|---|
| Isolate: C-1-11 | | | | | | | | |
| Mean ± | 0.408 | 0.392 | 0.446 | 0.429 | 0.464 | 0.447 | 0.490 | 0.455 |
| S.D.[a] | 0.233 | 0.251 | 0.261 | 0.262 | 0.258 | 0.262 | 0.306 | 0.266 |
| Isolate: S-1-10 | | | | | | | | |
| Mean ± | 0.499 | 0.374 | 0.385 | 0.406 | 0.414 | 0.601 | 0.559 | 0.573 |
| S.D.[a] | 0.251 | 0.256 | 0.226 | 0.259 | 0.263 | 0.365 | 0.373 | 0.326 |

[a]Standard deviations were high due to one dog that consistently had low ELISA responses to both C-1-11 and S-1-10 antigen.

D. Immunogenicity Test.

One to four ticks were collected from all dogs except 6 vaccinates (bandages were dislodged or removed by the dogs in the later stages of feeding and ticks that had attached and fed were lost). Some recovered ticks were damaged or dead. Bb positive ticks were recovered from 3 of 19 vaccinates and 3 of 9 controls (Table 13). The occurrence of Bb positive ticks did not necessarily correlate with the infection observed.

Four of 9 (44%) nonvaccinate dogs had positive skin biopsies (Table 4). All skin biopsies collected from vaccinated dogs were negative for Bb. This is a significant ($P=0.0016$, Fisher's Exact Test) reduction of infection in the vaccinate group. All cultures with spirochetal growth were identified as Bb by FA. All of the blind-passage cultures remained negative. None of the skin biopsies collected approximately 15 cm from the tick attachment area in either the control or vaccinate groups were positive for Bb (Table 13).

TABLE 13

Immunogenicity Test: *B. burgdorferi* identified by FA in ticks recovered from dogs and cultured from skin biopsies collected from the tick attachment site and a separate distant site approximately two weeks after tick attachment.

|  | No. Ticks FA Pos. Per No. Tested | Attachment Site No. Biop. Pos. Per No. Tested | Distant Site No. Biop. Pos. Per No. Tested |
|---|---|---|---|
| Vaccinates |  |  |  |
| KCP | NT[a] | 0/4 | 0/2 |
| PIP | 1/2 | 0/4 | 0/2 |
| KHP | 0/1 | 0/4 | 0/2 |
| PGP | 0/3 | 0/4 | 0/2 |
| OGO | NT | 0/4 | 0/2 |
| JAO | 0/1 | 0/4 | 0/2 |
| HXO | 0/4 | 0/4 | 0/2 |
| KIP | 0/1 | 0/4 | 0/2 |
| PDP | NT | 0/4 | 0/2 |
| PBP | 0/2 | 0/4 | 0/2 |
| JIO | NT | 0/4 | 0/2 |
| LUP | 0/3 | 0/4 | 0/2 |
| PZP | NT | 0/4 | 0/2 |
| PQP | 0/3 | 0/4 | 0/2 |
| HZO | 1/3 | 0/4 | 0/2 |
| OEP | 0/1 | 0/4 | 0/2 |
| IXP | 0/1 | 0/4 | 0/2 |
| OWO | NT | 0/4 | 0/2 |
| RJP | 1/3 | 0/4 | 0/2 |
| Dogs Pos./No. Challenged |  | 0/19 | 0/19 |
| Nonvaccinates |  |  |  |
| OIP | 2/4 | 3/3 | 0/2 |
| LLO | 1/4 | 0/4 | 0/2 |
| QDP | 0/2 | 0/4 | 0/2 |
| JXP | 0/2 | 3/4 | 0/2 |
| OPP | 0/2 | 0/4 | 0/2 |
| JBO | 0/1 | 1/4 | 0/2 |
| JCO | 0/1 | 0/4 | 0/2 |
| IOP | 2/2 | 0/4 | 0/2 |
| KYO | 0/2 | 2/4 | 0/2 |
| Dogs Pos./No. Challenged |  | 4/9 | 0/9 |

[a]NT (Not tested. Ticks damaged or no viable ticks recovered.)

Table 14 lists the results of blood cultures. One of 9 nonvaccinates had positive blood cultures at dilutions 1:10 and 1:100 approximately one week after attachment of ticks (i.e. during feeding). Blood cultures were otherwise negative except for week 6 after tick attachment. At this time 9 of 19 vaccinates and 6 of 9 controls had positive blood cultures at 1:100 and 1:1000 dilutions (as determined by growth and FA), but not at the initial 1:10 dilution. Since this was a questionable result, the blood samples were recultured, and the blood and the 1:10 dilution were tested by FA. There was no spirochetal growth in the recultured blood and no spirochetes were detected in the blood or the 1:10 dilution by FA.

TABLE 14

Immunogenicity Test: *B. burgdorferi* cultured from blood collected from dogs prior to and following tick attachment.

| | Blood Cultures Weeks Post Attachment | | | | | | | | | |
|---|---|---|---|---|---|---|---|---|---|---|
|  | 0 | 1 | 2 | 4 | 5 | 6 | 7 | 8 | 9 | 10 |
| Vaccinates |  |  |  |  |  |  |  |  |  |  |
| KCP | − | − | − | − | − | − | − | − | − | − |
| PIP | − | − | − | − | − | − | − | − | − | − |
| KHP | − | − | − | − | − | − | − | − | − | − |
| PGP | − | − | − | − | − | − | − | − | − | − |
| OGO | − | − | − | − | − | − | − | − | − | − |
| JAO | − | − | − | − | − | + | − | − | − | − |
| HXO | − | − | − | − | − | + | − | − | − | − |
| KIP | − | − | − | − | − | − | − | − | − | − |
| PDP | − | − | − | − | − | − | − | − | − | − |
| PBP | − | − | − | − | − | + | − | − | − | − |
| JIO | − | − | − | − | − | + | − | − | − | − |
| LUP | − | − | − | − | − | + | − | − | − | − |
| PZP | − | − | − | − | − | + | − | − | − | − |
| PQP | − | − | − | − | − | − | − | − | − | − |
| HZO | − | − | − | − | − | + | − | − | − | − |
| OEP | − | − | − | − | − | + | − | − | − | − |
| IXP | − | − | − | − | − | + | − | − | − | − |
| OWO | − | − | − | − | − | − | − | − | − | − |
| RJP | − | − | − | − | − | − | − | − | − | − |
| Dogs Pos. Per No. Tested |  |  |  |  |  | 9/19 |  |  |  |  |
| Nonvaccinates |  |  |  |  |  |  |  |  |  |  |
| OIP | − | + | − | − | − | + | − | − | − | − |
| LLO | − | − | − | − | − | + | − | − | − | − |
| QDP | − | − | − | − | − | + | − | − | − | − |
| JXP | − | − | − | − | − | + | − | − | − | − |
| OPP | − | − | − | − | − | + | − | − | − | − |
| JBO | − | − | − | − | − | − | − | − | − | − |
| JCO | − | − | − | − | − | + | − | − | − | − |
| IOP | − | − | − | − | − | − | − | − | − | − |
| KYO | − | − | − | − | − | − | − | − | − | − |
| Dogs Pos. Per No. Tested |  | 1/9 |  |  |  | 6/9 |  |  |  |  |

[a]Blood collected at time of tick placement on dogs.
+ (Growth)
− (No Growth)

Figure 4:
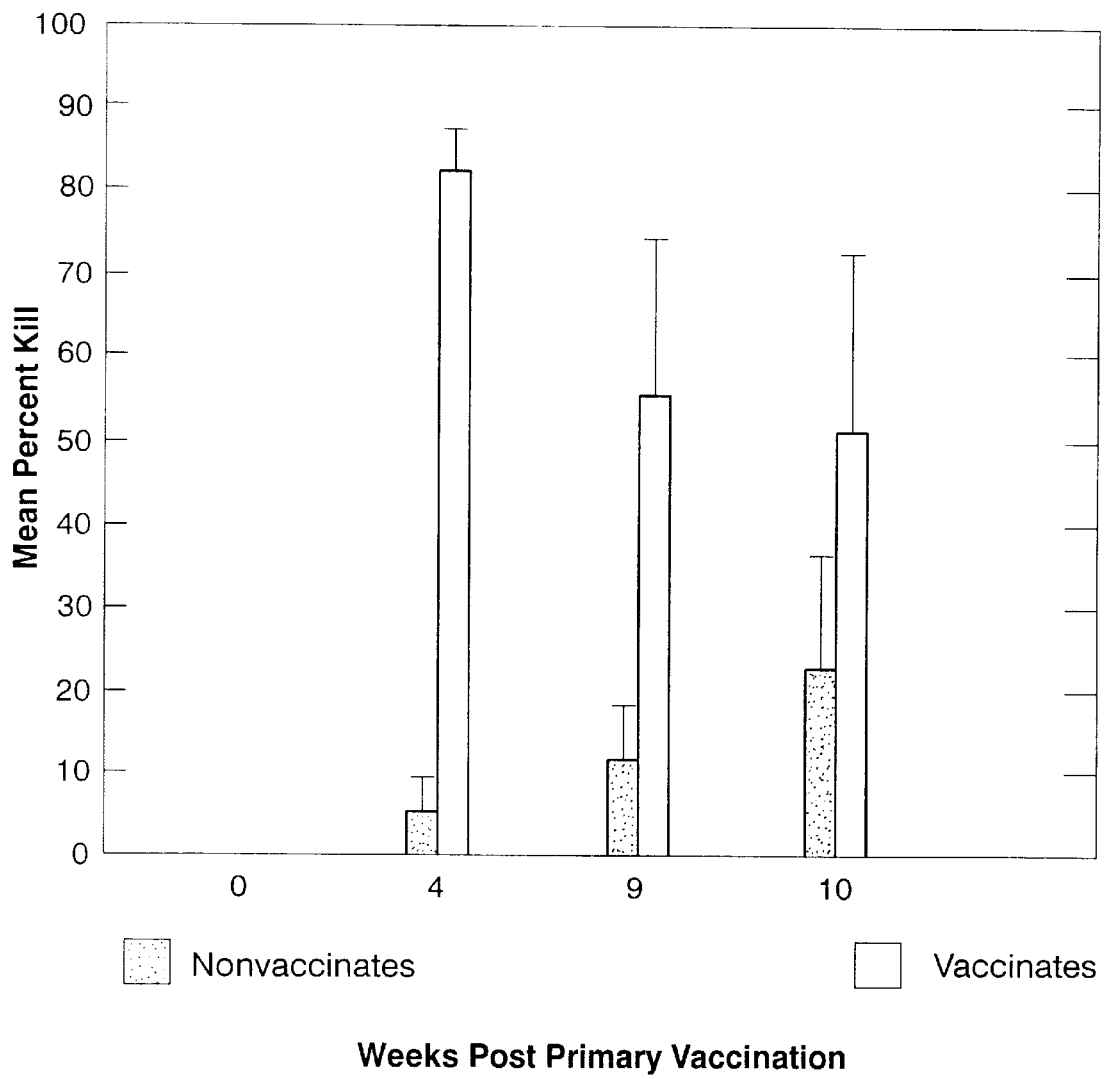
FIG. 4. Immunogenicity Test: Borreliacidal antibodies to isolate S-1-10 as measured by Borreliacidal Assay after vaccination with a bivalent *B. burgdorferi* bacterin and following challenge with *B. burgdorferi* infected ticks.
Figure 5:
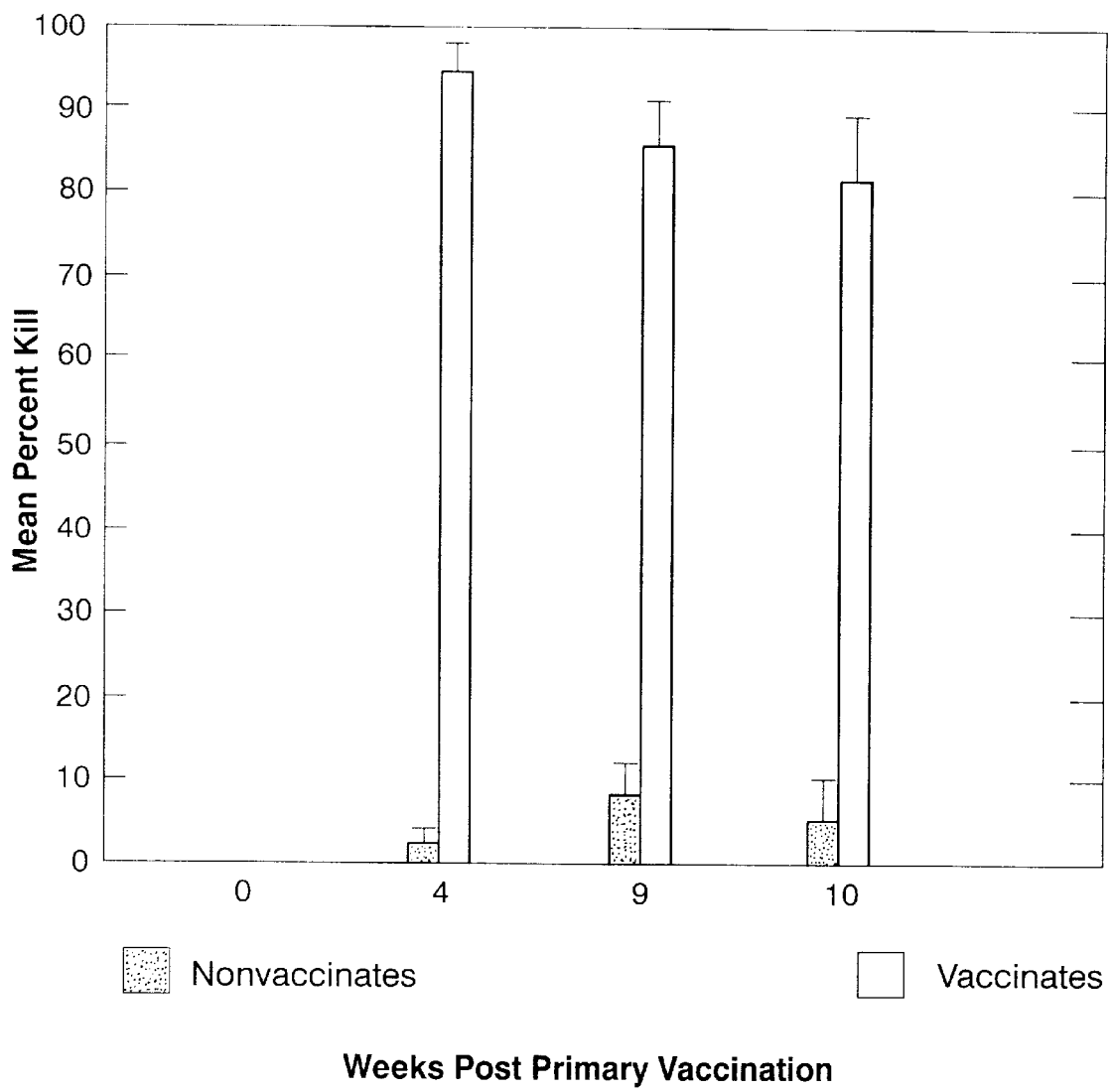
FIG. 5. Immunogenicity Test: Borreliacidal antibodies to isolate C-1-11 as measured by Borreliacidal Assay after vaccination with a bivalent *B. burgdorferi* bacterin and following challenge with *B. burgdorferi* infected ticks.

FIGS. 4 and 5 illustrate borreliacidal antibody responses against isolates S-1-10 and C-1-11 following vaccination and tick attachment. Serum samples from vaccinates showed a strong antibody response to both S-1-10 and C-1-11 one week after second vaccination. Five weeks after tick attachment borreliacidal antibody responses against both S-1-10 and C-1-11 increased slightly in the nonvaccinate group. However, 6 weeks after tick attachment a stronger borreliacidal antibody response against only the S-1-10 was observed in the nonvaccinate group.

Serum samples tested by ELISA also showed a strong antibody response to both S-1-10 and C-1-11 antigens one week after second vaccination (FIGS. 3 and 4). Subsequently, the antibody response slowly decreased. Nonvaccinates had increased antibody responses observed at week 8, 9 and 10 (4, 5, and 6 weeks after tick attachment-FIGS. 6 and 7).

No dogs had adverse reactions to vaccination either immediately or during the observations periods following vaccinations and tick attachment.

To date, none of the dogs have exhibited clinical signs associated with Lyme disease.

III. DISCUSSION

All dogs of the challenge model study were infected as determined by skin biopsy cultures (4 of 4 dogs positive), blood cultures (4 of 4 dogs positive, and serology (all dogs, except dog No. 450, seroconverted as determined by either BA or ELISA). Dogs are currently being observed for clinical signs. Ticks used to infect these dogs were also used to infect immunogenicity test dogs.

Ticks infected 4 of 9 nonvaccinates and none of the 19 vaccinates. This is a significant (P=0.0016, Fisher's Exact Test) reduction of infection and correlated with the presence of borreliacidal antibody. There was a significant (P=0.0422, Fisher's Exact Test) reduction of infection in the vaccinate group when skin biopsy infection and spirochetemia were evaluated collectively.

Vaccinates of the immunogenicity test had strong borreliacidal antibody responses to both vaccine isolates at the time of tick attachment. Following tick attachment, antibody responses as measured by BA declined in the vaccinate group for both isolates. In contrast, borreliacidal antibody against S-1-10 increased in the nonvaccinated group. This increase reflected the infections observed in this group. An increase in the nonvaccinate group to both C-1-11 and S-1-10 antigens was measured by ELISA. These observations support those cited previously (Lovrich, S. D. et al. (1993) Infect. and Immun. 61:4367–4374) that the borreliacidal assay distinguishes between isolates of different seroprotective groups whereas ELISA assay fail to make that distinction. The data indicate that the Borrelia carried by the ticks are likely to be classified in the same seroprotective group as S-1-10. However, the mean BA responses increased against both isolates in the challenge model test following tick attachment. It is possible that the pool of ticks were infected with either isolates of either seropositive group, both groups or possibly other seroprotective group.

Bacteria cultivated in protein-rich media and incorporated into multicomponent bacterins have the potential for producing adverse reactions (edema, swelling, soreness, lethargy, hypersensitivity) resulting from interaction between animal, vaccine, and environment. In this study no abnormal reactions were observed in any of the vaccinates after either vaccination with a bacterin containing 2 isolates of Bb.

IV. CONCLUSION

The ticks used in these studies were capable of infecting dogs with *B. burgdorferi*.

The vaccine induced high levels of borrelicidal antibody, was efficacious against a natural tick challenge, and was safe.

Example 14

Immunogenicity Test and Duration of Immunity Study

I. Materials and Methods

A. Animals

Beagles from the colony located at Solvay Animal Health, Inc., Charles City, Iowa were used in the study. Dogs were 12 to 24 weeks of age at the time of vaccination (Table 15) and were seronegative (<1:20) to *B. burgdorferi* as tested by a whole cell ELISA.

TABLE 15

Dogs used in the study

| Dog No. | Sex | Date of Birth | Age (weeks) at first vac |
|---|---|---|---|
| Vaccinates | | | |
| 558 | F | 5-10-92 | 18 |
| 560 | F | 5-06-92 | 20 |
| 562 | F | 5-11-92 | 20 |
| 564 | F | 5-11-92 | 20 |
| 566 | F | 5-11-92 | 20 |
| 568 | F | 5-11-92 | 20 |
| 570 | F | 5-25-92 | 18 |
| 574 | F | 5-25-92 | 18 |
| 580 | F | 5-26-92 | 16 |
| 582 | F | 5-26-92 | 16 |
| 584 | F | 6-19-92 | 12 |
| 586 | F | 6-19-92 | 12 |
| 609 | M | 4-14-92 | 24 |
| 615 | M | 4-14-92 | 24 |
| 617 | M | 4-22-92 | 20 |
| 627 | M | 4-22-92 | 22 |
| 639 | M | 5-06-92 | 18 |
| 641 | M | 5-06-92 | 18 |
| 643 | M | 5-06-92 | 18 |
| 647 | M | 5-11-92 | 18 |
| Nonvaccinates | | | |
| 554 | F | 4-22-92 | 22 |
| 556 | F | 5-10-92 | 20 |
| 598 | F | 8-12-92 | 4 |
| 608 | F | 8-12-92 | 4 |
| 610 | F | 8-17-92 | 4 |
| 612 | F | 8-17-92 | 4 |
| 651 | M | 5-25-92 | 18 |
| 655 | M | 5-26-92 | 18 |
| 661 | M | 7-10-92 | 11 |
| 663 | M | 7-14-92 | 11 |
| 665 | M | 7-14-92 | 11 |
| 669 | M | 8-12-92 | 4 |
| 671 | M | 8-12-92 | 4 |
| 673 | M | 8-12-92 | 4 |
| 677 | M | 8-12-92 | 4 |

B. Bacterin Preparation

The bacterin was prepared from *B. burgdorferi* S-1-10 and C-1-11 serotypes at the eight passage from the master seed as described above. The bacterin was formulated to contain $5 \times 10^8$ cells of each serotype per one ml dose and adjuvanted with aluminum hydroxide (Rehydragel HPA, Reheis Chemical Co., Berkeley Hts., N.J.) at 1.5 mg aluminum oxide per one ml dose. The vaccine was stored at 4° C. until used.

C. Vaccination

Twenty dogs were vaccinated intramuscularly in the caudal thigh with two 1.0 ml doses at three weeks apart. The first dose was given at 12 to 24 weeks of age. The second dose was given three weeks following the first dose. Dogs were observed for abnormal reactions, temperatures were recorded and injection sites were palpated daily for one week after each vaccination. A group of fifteen nonvaccinated dogs served as controls.

D. Serology

Blood was collected before and after vaccination, and at intervals after challenge. Serum was tested for antibody to *B. burgdorferi* by a borreliacidal antibody assay, whole cell ELISA and OspA ELISA, and western immunoblotting.

E. Whole Cell ELISA

Antibody response to surface antigens of *B. burgdorferi* was determined by a modification of a whole cell ELISA used by the Regional Animal Health Laboratory, Baron, Wis. Late log phase cultures of both C-1-11 and S-1-10 were inactivated with binary ethyleneimine (BEI). Following neutralization of the BEI with sodium thiosulfate, the cells were washed by centrifugation three times with sterile saline. The total protein content of the inactive organisms was determined by a bicinchoninic acid (BCA) protein assay (Pierce Co., Rockford, Ill.). Wells of IMMULON 3 plates (Dynatech Laboratories, Inc., Chantilly, Va.) were coated with whole cell antigen at 0.3 µg in 100 µl sodium carbonate coating buffer. Plates were incubated in a humid chamber at 4° C. for 15 to 17 hours. Following incubation, the contents of the plate were discarded and wells were filled with PBS containing 5% nonfat dried milk (NFDM) and incubated in a humid chamber for 60 minutes at 37° C. Wells were emptied and 50 µl of test serum diluted in PBS containing 0.05% TWEEN-20 (PBS-TW) were added to duplicate wells and incubated in a humid chamber for 60 minutes at 37° C. Positive and negative canine control serum was included on each plate. Plates were washed three times with saline containing 0.05% TWEEN-20 and 50 µl aliquots of peroxidase labeled goat anti-dog IgG (Kirkegaard & Perry Laboratories, Inc., Gaithersburg, Md.) diluted 1:1500 in PBS-TW were added per well. The plates were incubated in a humid chamber for 60 minutes at 37° C. and washed three times with PBS-TW. The substrate was prepared by dissolving 30.0 mg of O-Phenylenediamine in a 0.051M dibasic sodium phosphate, 0.024M citric acid, 0.012% hydrogen peroxide solution and 100 µl aliquots were added to each well. The reaction was stopped with 50 µl per well of 2N sulfuric acid and the optical density of each well was determined at 490 nm in an ELISA reader. The titer was defined as the reciprocal of the last dilution that gave an optical density of 30% of the peak optical density.

E. Osp A ELISA

Wells of a 96-well microtiter plate were coated with 50 ng of recombinant OspA and incubated overnight at 4° C.

Wells were post-coated with 5% NFDM in PBS for 30 minutes at 37° C. Wells were washed three times with PBS-TW and 50 µl of two-fold dilutions of dog serum were added to the wells. Plates were incubated at 37° C. for one hour. Wells were washed with PBS-TW and 50 µl of goat anti-dog IgG.HRP (Kirkegaard & Perry Laboratories, Inc., Gaithersburg, Md.) were added to the wells. After incubation for one hour at 37° C., bound antibody was detected by the addition of ABTS substrate (Kirkegaard & Perry Laboratories, Inc., Gaithersburg, Md.). Optical density of each well was determined at 405 nm in an ELISA reader. The titer was defined as the reciprocal of the last dilution that gave an optical density of 30% of the peak optical density.

F. Western Immunoblotting

Mid to late log phase cultures of *B. burgdorferi* were harvested by centrifugation of 15,000 g, 4° C., 30 minutes and washed three times by centrifugation with sterile saline. A suspension of approximately $1 \times 10^8$ cells were boiled in electrophoresis sample buffer for nine minutes and electrophoresed on a 10% SDS-polyacrylamide gel (Laemmli, E. K. (1970) Nature 227:680–685). Proteins were electroblotted onto Immobilon™ PVDF membrane (Millipore Corp., Bedford, Mass.) by a modification of the procedure described by Towbin (Towbin, H. et al. (1979) Proc. Natl. Acad. Sci. 76:4350–4354). The PVDF membrane was incubated for 90 minutes at 22° C. in 20 mM tris, 150 mM NaCl pH 7.2 (TBS) with 5% NFDM. Strips were incubated with canine serum or monoclonal antibody to OspA diluted 1:75 in the blocking buffer for 60 minutes at 22° C. Strips were then washed two times in TBS containing 0.2% TRITON X-100 and one time in TBS. Bound antibody was detected by the addition of horseradish peroxidase-labeled anti-canine or anti-murine IgG (Kirkegaard & Perry Laboratories Inc., Gaithersburg, Md.). Protein bands were visualized with a TMB membrane peroxidase substrate system (Kirkegaard & Perry Laboratories, Inc., Gaithersburg, Md.).

G. Detection of Borreliacidal Antibody by Flow Cytometry

The borreliacidal assay was performed using a modification of previously described procedures (Lim, L. C. et al. (1994) Clin. Diag. Lab. Immunol. 1:44–50; Sachsenmeirer, K. F. et al. (1992) J. Clin. Microbiol. 30:1457–1461). Briefly, a 72 hour mid-log phase culture of *B. burgdorferi* isolate C-1-11 and S-1-10 in modified Barbour Stoenner Kelly (BSK) medium was quantified in a Petroll-Hauser chamber and diluted to contain $1 \times 10^6$ cells/ml BSK medium. Aliquots of 100 µl of diluted, heat inactivated serum were mixed with 100 µl of each *B. burgdorferi* suspension and 10 µl of guinea pig serum complement (210 $CH_{50}$ units; GIBCO Laboratories, Grand Island, N.Y.) were added. The suspension was gently mixed and incubated at 32° C. for 16 to 24 hours. After incubation of the reaction tubes, 100 µl of the reaction mixture was diluted with phosphate buffered saline (PBS) containing $5.4 \times 10^{-9}$ M acridine orange. Detection of borreliacidal activity was performed using a modification of previously described procedures (Callister, S. M. et al., (1992) J. Infec. Dis. 167:158–164). Killing by borreliacidal antibodies causes blebbing of *B. burgdorferi* cell walls and higher concentrations of acridine orange are absorbed into and into these damaged cell walls. Consequently, killed *B. burgdorferi* organisms fluoresce at a much greater intensity than normal live spirochetes. An increase in fluorescence intensity of $\geq 16\%$ compared with organisms exposed to normal dog serum was considered positive for borreliacidal activity. The end point titer was expressed as the reciprocal of the last dilution at which there was a $\geq 16\%$ increase in fluorescence intensity. Dogs with a titer of <1:20 were determined to be negative.

H. Challenge of Dogs with *B. burgdorferi* Infected Ticks

A total of 631 *I. scapularis* male and 732 female ticks were collected from a Lyme disease endemic area near Ettrick, Wis. To establish the overall *B. burgdorferi* infection rate of the ticks, the midguts of 50 male *I. scapularis* ticks were examined by fluorescent antibody assay (FA) using the Osp A monoclonal antibody obtained from Dr. A. G. Barbour. At seven months post second vaccination, dogs were challenged with 10 female and 6 male ticks. Female ticks are the only adult ticks that transmit the disease. Male ticks are needed for proper feeding of the female ticks. For each dog, five female and three male ticks were randomly selected from the pool of ticks and placed in two small petri dishes that were secured to a shaved area on the left dorsal-anterior area of he thorax of each dog. The ticks were allowed to feed for one week. During this time, ticks were observed at two day intervals. One week post attachment, ticks were recovered and the midguts examined for the presence of *B. burgdorferi* by FA with the *B. burgdorferi* monoclonal antibody.

I. Observation of Dogs for Clinical Signs of Lyme Disease

Dogs were observed daily following challenge for clinical signs associated with Lyme disease. The symptom used as the primary indicator of clinical Lyme disease was lameness. Lameness was defined as reluctance to bear weight on an affected limb with or without swelling and temperature at the affected joint, stiff leggedness, and the migration of lameness from joint to joint or limb to limb. Dogs were also observed for lethargy and fever.

J. Isolation of *B. burgdorferi* from Dogs After Challenge

Attempts were made to isolate *B. burgdorferi* from the skin, blood, joints, and organs of dogs. Skin biopsies were taken from anesthetized dogs at eighteen to nineteen days following tick attachment and at the time of necropsy. Skin biopsies were taken from the tick attachment site and in some dogs, skin biopsies were taken from sites distant to the tick bite site. Distant sites were located ventral to the tick bite site, posterior to the tick bite site, and on the right side of the dorsal-anterior area of the thorax on the opposite side of the dog. Skin biopsy sites were shaved, washed with Solvahex™ Surgical Scrub, and rinsed thoroughly with sterile water to remove residual disinfectant. An elliptical incision was made through the dermal and subcutaneous skin layers. Approximately one gram of skin was placed in nine ml BSK medium containing 0.15% agarose and 40 μg rifampin/ml. The biopsy sample was homogenized and two additional 10-fold dilutions of the homogenate were made in nine ml blanks of the BSK medium. Cultures were incubated at 32° C. for six weeks and were examined microscopically at weekly intervals for the growth of spirochetes. Cultures showing spirochete growth were confirmed as *B. burgdorferi* by FA with the *B. burgdorferi* monoclonal antibody. After six weeks incubation, negative cultures were subcultured to fresh BSK medium by inoculating one ml of negative culture into nine ml of fresh BSK medium. These cultures were incubated at 32° C. for an additional six weeks and examined as described above. Cultures negative for spirochete growth were discarded.

The whole heart, spleen, kidneys, and bladder were separately homogenized in 50 ml BSK containing agarose and rifampin by the use of a STOMACHER (Seward Medical, London, England). A 50 ml sample was poured off and diluted $10^{-1}$ and $10^{-2}$ in BSK medium. The 50 ml sample and dilutions were incubated for six weeks at 32° C., observed and confirmed as *B. burgdorferi* as described.

A two to three ml sample of cerebrospinal fluid was added to nine ml BSK medium and an additional 1:10 dilution was made in the same medium, incubated and observed as described.

Joint tissue was taken from the elbow, carpus, knee, and tarsus. The tissue from each joint was added to nine ml BSK medium containing agarose and rifampin. An additional 1:10 dilution was made in the same medium, and cultures were incubated and observed as described.

K. Blood Cultures

Heparinized blood samples for the isolation of *B. burgdorferi* were collected at the time of challenge, at weekly intervals following challenge and at necropsy. Blood from each dog was diluted $10^{-1}$, $10^{-2}$, and $10^{-3}$ in BSK medium. The cultures were incubated at 32° C. for six weeks and examined weekly for the growth of *B. burgdorferi* as described.

L. Statistical Analysis

Significant differences were compared by Pearson's Chi Square analysis.

II. RESULTS

A. Vaccination

Dogs were vaccinated with two doses of vaccine at three weeks apart. After the first vaccination 14 of 20 dogs exhibited a slight fever of 1.5° F. above baseline temperatures (Table 16). Temperatures persisted in the majority of these dogs for only three days. Slightly elevated temperatures were recorded in dogs 566 and 568 for seven days post vaccination. A swollen vaccination site was observed in dog 560 that lasted for 4 days and then disappeared. After the second vaccination, 13 of 20 dogs exhibited slight fevers of 1.5° F. above baseline that persisted for three or four days (Table 17). Dog 615 had a elevated temperatures that lasted for eight days. Dogs did not exhibit any other post vaccination reactions and no severe hypersensitivity or anaphylaxis reactions were observed.

TABLE 16

Temperatures of dogs after first vaccination.

Temperatures (° F.) on days post vaccination

| Dog | 0 | 1 | 2 | 3 | 4 | 5 | 6 | 7 | 8 | 9 | 10 |
| --- | --- | --- | --- | --- | --- | --- | --- | --- | --- | --- | --- |
| 574 | 101.9 | 103.3 | 102.6 | 102.2 | 103.9 | 102.9 | 101.6 | 102.6 | 104.5 | 104.0 | 101.9 |
| 586 | 101.7 | 102.3 | 102.3 | 102.3 | 102.8 | 102.5 | 102.7 | ND | ND | ND | ND |
| 615 | 103.6 | 103.5 | 102.8 | 103.2 | 102.5 | 103.1 | 103.2 | 103.2 | 103.4 | 103.3 | 102.9 |
| 627 | 101.2 | 102.4 | 102.3 | 102.4 | 101.9 | 102.1 | 102.3 | 102.1 | 102.2 | 102.1 | 102.5 |
| 639 | 101.2 | 101.4 | 102.3 | 102.2 | 102.7 | 102.1 | 101.9 | ND | ND | ND | ND |
| 558 | 102.4 | 102.3 | 104.0 | 102.4 | 102.2 | 102.5 | 101.9 | ND | ND | ND | ND |
| 560 | 102.4 | 102.4 | 103.0 | 102.2 | 103.0 | 102.5 | 102.1 | 102.2 | 102.3 | 102.4 | 102.4 |
| 562 | 101.2 | 102.2 | 102.7 | 103.0 | 102.0 | 102.4 | 102.9 | 103.3 | 102.5 | 103.0 | 102.9 |
| 564 | 102.2 | 103.1 | 103.2 | 103.2 | 102.6 | 102.9 | 104.0 | 103.2 | 102.9 | 103.4 | 103.0 |
| 566 | 102.1 | 103.1 | 102.5 | 104.1 | 103.0 | 103.6 | 104.0 | 104.0 | 103.7 | 103.1 | 102.9 |
| 568 | 102.9 | 103.2 | 104.1 | 103.3 | 103.3 | 103.6 | 103.8 | 104.4 | 103.3 | 102.9 | 102.6 |
| 570 | 101.9 | 103.2 | 101.9 | 103.0 | 103.0 | 103.3 | 103.0 | 102.7 | 101.9 | 102.3 | 102.0 |
| 580 | 103.0 | 103.2 | 103.3 | 102.9 | 103.2 | 102.4 | 102.5 | ND | ND | ND | ND |
| 582 | 102.4 | 103.5 | 103.1 | 102.6 | 101.6 | 102.4 | 102.5 | ND | ND | ND | ND |
| 584 | 101.2 | 102.7 | 102.1 | 103.1 | 102.9 | 103.1 | 102.5 | ND | ND | ND | ND |
| 609 | 102.3 | 103.6 | 102.7 | 102.9 | 102.9 | 103.6 | 103.7 | 103.1 | 103.2 | 102.8 | 102.8 |
| 617 | 101.8 | 103.0 | 103.1 | 102.4 | 102.5 | 102.8 | 101.7 | ND | ND | ND | ND |
| 641 | 102.0 | 101.9 | 103.7 | 103.5 | 102.6 | 102.6 | 102.4 | ND | ND | ND | ND |
| 643 | 102.8 | 102.9 | 104.3 | 103.9 | 103.4 | 102.9 | 103.0 | ND | ND | ND | ND |
| 647 | 102.7 | 103.0 | 103.3 | 103.0 | 103.3 | 102.5 | 102.9 | ND | ND | ND | ND |

TABLE 17

Temperature of dogs after second vaccination.

Temperatures (° F.) on days post vaccination

| Dog | 0 | 1 | 2 | 3 | 4 | 5 | 6 | 7 | 8 | 9 | 10 |
|---|---|---|---|---|---|---|---|---|---|---|---|
| 574 | 103.6 | 102.5 | 103.8 | 104.9 | 101.6 | 101.0 | 103.0 | 104.1 | 103.7 | 102.1 | ND |
| 586 | 102.1 | 103.3 | 101.6 | 102.4 | 103.2 | 102.8 | 103.1 | 101.6 | ND | ND | ND |
| 615 | 102.6 | 104.7 | 104.3 | 103.2 | 104.1 | 104.1 | 104.6 | 104.2 | 105.1[1] | 103.4 | ND |
| 627 | 101.6 | 102.0 | 102.2 | 102.2 | 101.7 | 101.6 | 102.9 | 102.6 | 102.8 | 102.1 | ND |
| 639 | 102.3 | 102.9 | 102.0 | 101.8 | 102.5 | 102.5 | 102.4 | 102.8 | ND | ND | ND |
| 558 | 102.6 | 103.5 | 103.0 | 101.4 | 103.4 | 102.6 | 102.6 | 102.9 | ND | ND | ND |
| 560 | 102.1 | 102.9 | 102.4 | 102.4 | 101.9 | 101.7 | 102.6 | 101.9 | 102.1 | 102.3 | ND |
| 562 | 101.2 | 1042. | 103.6 | 104.1 | 102.1 | 102.8 | 103.5 | 102.8 | 102.6 | 102.8 | ND |
| 564 | 102.4 | 103.6 | 102.8 | 102.7 | 102.7 | 102.6 | 102.9 | 102.8 | 103.1 | 102.9 | ND |
| 566 | 102.1 | 103.0 | 103.2 | 103.7 | 102.9 | 102.5 | 103.4 | 102.4 | 102.1 | 102.8 | ND |
| 568 | 102.9 | 102.5 | 103.9 | 103.0 | 103.1 | 103.0 | 104.2 | 103.3 | 103.2 | 101.8 | ND |
| 570 | 103.0 | 103.4 | 103.4 | 102.9 | 102.7 | 102.9 | 103.4 | 103.3 | 102.9 | 103.0 | ND |
| 580 | 102.9 | 103.0 | 103.1 | 102.1 | 103.0 | 103.3 | 103.0 | 103.3 | ND | ND | ND |
| 582 | 102.7 | 103.6 | 103.3 | 101.4 | 103.0 | 103.0 | 102.4 | 102.6 | ND | ND | ND |
| 584 | 102.1 | 102.7 | 101.9 | 102.5 | 102.8 | 102.5 | 102.8 | 102.4 | ND | ND | ND |
| 609 | 102.3 | 103.0 | 103.1 | 103.2 | 102.8 | 103.5 | 103.9 | 103.7 | 103.1 | 102.4 | ND |
| 617 | 101.3 | 102.6 | 102.6 | 101.8 | 102.6 | 103.1 | 102.5 | 102.9 | ND | ND | ND |
| 641 | 103.3 | 103.0 | 102.7 | 102.6 | 102.9 | 103.0 | 103.1 | 102.4 | ND | ND | ND |
| 643 | 103.4 | 103.6 | 103.4 | 102.4 | 104.0 | 102.9 | 104.1 | 103.5 | ND | ND | ND |
| 647 | 102.6 | 103.2 | 102.8 | 102.2 | 103.3 | 103.7 | 103.3 | 103.3 | ND | ND | ND |

B. Antibody Response to *B. burgdorferi* Whole Cell Antigens.

An ELISA that used whole *B. burgdorferi* cells was used to demonstrate the serological response of vaccinated and challenged dogs to surface antigens of B. burgdorferi. Prior to vaccination, all dogs were seronegative. At three weeks post second vaccination, the geometric mean titer (GMT) was 1,236 against the S-1-10 strain and 816 against the C-1-11 strain (Table 18). Six months later, at the time of challenge, antibody titers in vaccinates had declined to 343 and 234 for S-1-10 and C-1-11, respectively. Antibody titers to both strains remained essentially unchanged in vaccinates after challenge with infected ticks. Nonvaccinated control dogs were seronegative throughout the pre-challenge period. Post challenge, all control dogs were seropositive to both S-1-10 and C-1-11. The GMT in control dogs was 1167 and 1404 to S-1-10 and C-1-11, respectively, and were four to five-fold higher than titers in vaccinated dogs after challenge. However, antibody titers to both strains in dog No. 669 were 8 to 16-fold lower than the GMT of the control dogs.

TABLE 18

Whole Cell ELISA antibody response.

| | Prevaccination | | Post Vaccination | | Pre-challenge | | 8 Wks. Post Challenge | |
|---|---|---|---|---|---|---|---|---|
| Dog. No. | C-1-11[1] | S-1-10[2] | C-1-11 | S-1-10 | C-1-11 | S-10-10 | C-1-11 | S-1-10 |
| Vaccinates | | | | | | | | |
| 574 | NEG[3] | NEG | 1280 | 1280 | 320 | 160 | 160 | 320 |
| 586 | NEG | NEG | 320 | 320 | 160 | 160 | 1280 | 1280 |
| 615 | NEG | NEG | 2560 | 1280 | 640 | 320 | 320 | 160 |
| 627 | NEG | NEG | 5120 | 2560 | 320 | 320 | 320 | 320 |
| 639 | NEG | NEG | 2560 | 1280 | 640 | 320 | 320 | 320 |
| 558 | NEG | NEG | 640 | 320 | 160 | 160 | 160 | 160 |
| 560 | NEG | NEG | 1280 | 1280 | 320 | 160 | 320 | 160 |
| 562 | NEG | NEG | 1280 | 640 | 640 | 160 | 320 | 320 |
| 564 | NEG | NEG | 1280 | 640 | 640 | 160 | 320 | 320 |
| 566 | NEG | NEG | 2560 | 1280 | 640 | 320 | 320 | 320 |
| 568 | NEG | NEG | 640 | 320 | 640 | 320 | 640 | 320 |
| 570 | NEG | NEG | 1280 | 1280 | 320 | 320 | 320 | 320 |
| 580 | NEG | NEG | 640 | 640 | 320 | 320 | 320 | 320 |
| 582 | NEG | NEG | 640 | 160 | 320 | 320 | 320 | 160 |
| 584 | NEG | NEG | 640 | 640 | 160 | 80 | 80 | 80 |
| 609 | NEG | NEG | 2560 | 1280 | 320 | 320 | 320 | 320 |
| 617 | NEG | NEG | 1280 | 640 | 640 | 320 | 640 | 320 |
| 641 | NEG | NEG | 1280 | 640 | 320 | 160 | 160 | 160 |
| 643 | NEG | NEG | 1280 | 640 | 640 | 640 | 320 | 320 |
| 647 | NEG | NEG | 1280 | 640 | 320 | 160 | 160 | 320 |
| GMT | NEG | NEG | 1236 | 816 | 343 | 234 | 299 | 269 |
| Nonvaccinates | | | | | | | | |
| 598 | NEG | NEG | NEG | NEG | NEG | NEG | 640 | 1289 |

TABLE 18-continued

Whole Cell ELISA antibody response.

| | Prevaccination | | Post Vaccination | | Pre-challenge | | 8 Wks. Post Challenge | |
|---|---|---|---|---|---|---|---|---|
| Dog. No. | C-1-11[1] | S-1-10[2] | C-1-11 | S-1-10 | C-1-11 | S-10-10 | C-1-11 | S-1-10 |
| 655 | NEG | NEG | NEG | NEG | NEG | NEG | 1280 | 2560 |
| 663 | NEG | NEG | NEG | NEG | NEG | NEG | 640 | 1280 |
| 669 | NEG | NEG | NEG | NEG | NEG | NEG | 160 | 80 |
| 677 | NEG | NEG | NEG | NEG | NEG | NEG | 5120 | 5120 |
| 610 | NEG | NEG | NEG | NEG | NEG | NEG | 1280 | 1280 |
| 612 | NEG | NEG | NEG | NEG | NEG | NEG | 1280 | 1280 |
| 651 | NEG | NEG | NEG | NEG | NEG | NEG | 2560 | 2560 |
| 661 | NEG | NEG | NEG | NEG | NEG | NEG | 640 | 1280 |
| 671 | NEG | NEG | NEG | NEG | NEG | NEG | 640 | 640 |
| 673 | NEG | NEG | NEG | NEG | NEG | NEG | 2560 | 2560 |
| 554 | NEG | NEG | NEG | NEG | NEG | NEG | 2560 | 2560 |
| 556 | NEG | NEG | NEG | NEG | NEG | NEG | 2560 | 2560 |
| 608 | NEG | NEG | NEG | NEG | NEG | NEG | 2560 | 2560 |
| 665 | NEG | NEG | NEG | NEG | NEG | NEG | 320 | 640 |
| GMT | NEG | NEG | NEG | NEG | NEG | NEG | 1167 | 1404 |

[1]Three weeks post second vaccination.
[2]Antibodies to either C-1-11 or S-1-10 whole cell antigen bound to plate wells.
[3]Negative-correlates to a titer <1:20.

C. Western Immunoblotting

Figure 6:
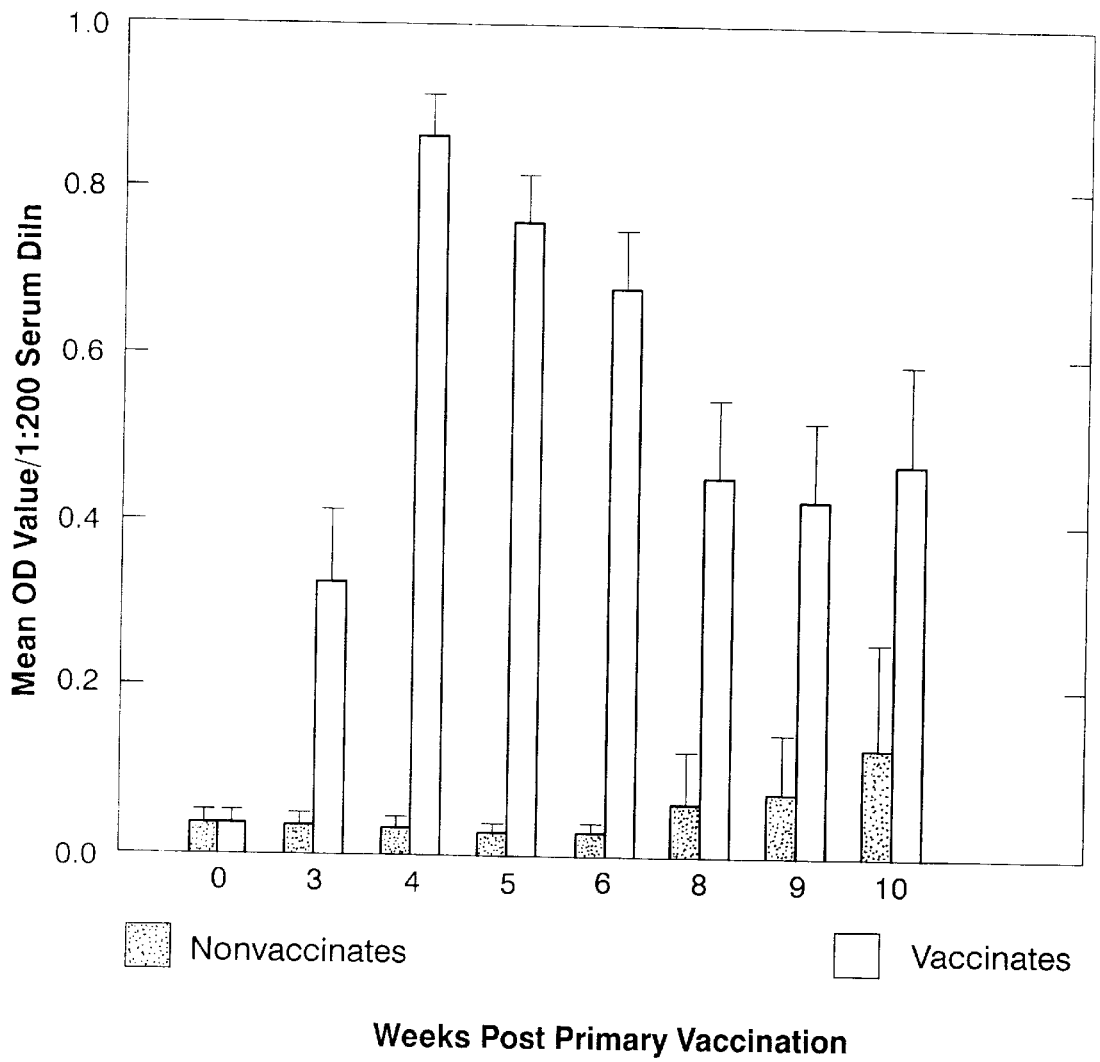
FIG. 6. Immunogenicity Test: Antibodies detected to S-1-10 antigen as measured by ELISA after vaccination with a bivalent *B. burgdorferi* bacterin and following challenge with *B. burgdorferi* infected ticks.
Figure 7:
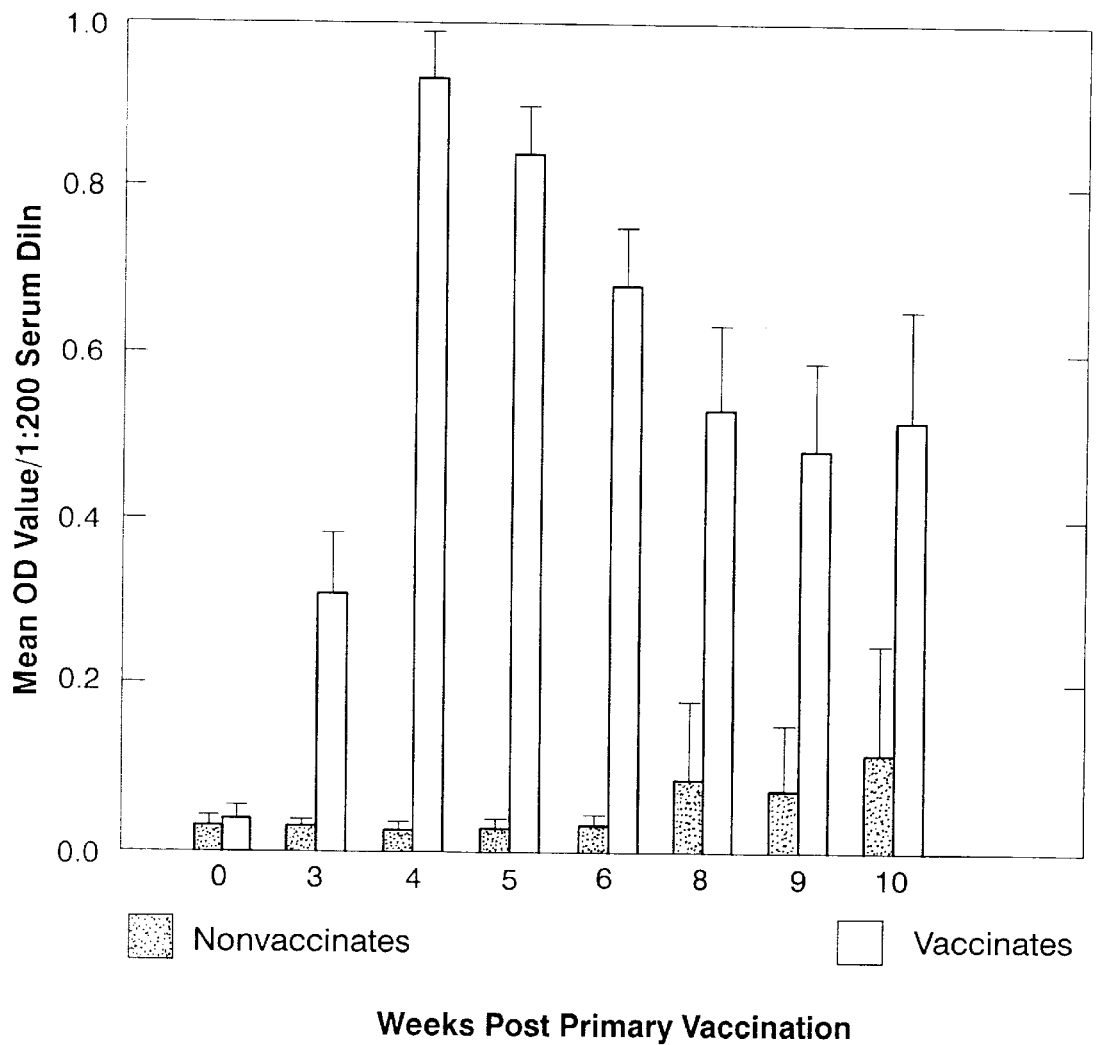
FIG. 7. Immunogenicity Test: Antibodies detected to C-1-11antigen as measured by ELISA after vaccination with a bivalent *B. burgdorferi* bacterin and following challenge with *B. burgdorferi* infected ticks.
Figure 8A:
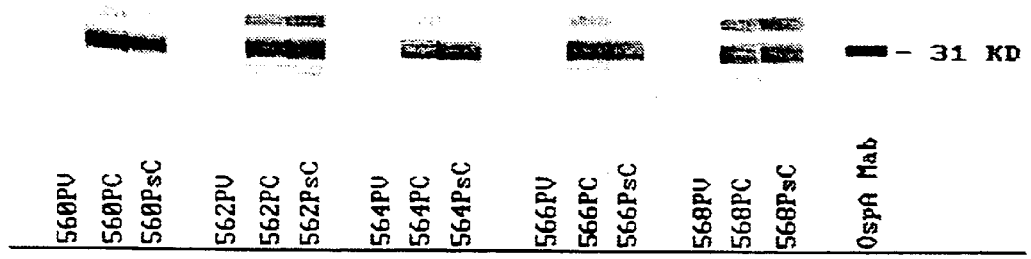
FIGS. 8A and 8B. Western Immunoblots of vaccinate serum collected at first vaccination (PV), seven months post second vaccination pre-tick challenge (PC), and eight weeks post tick challenge (PsC) against isolates S-1-10 (FIG. 8A) and C-1-11 (FIG. 8B).
Figure 8B:
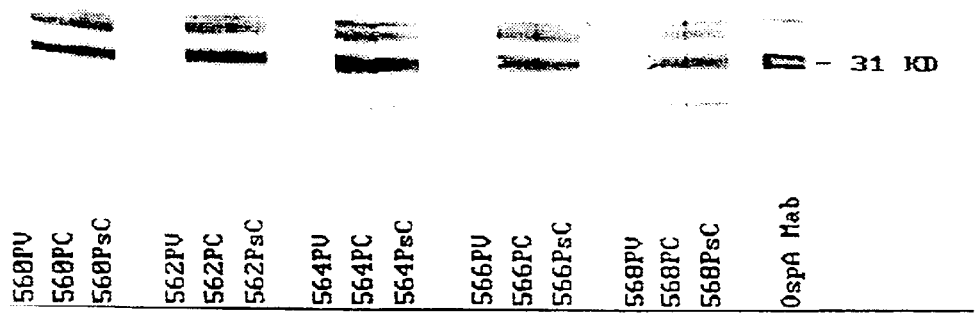
Figure 9A:
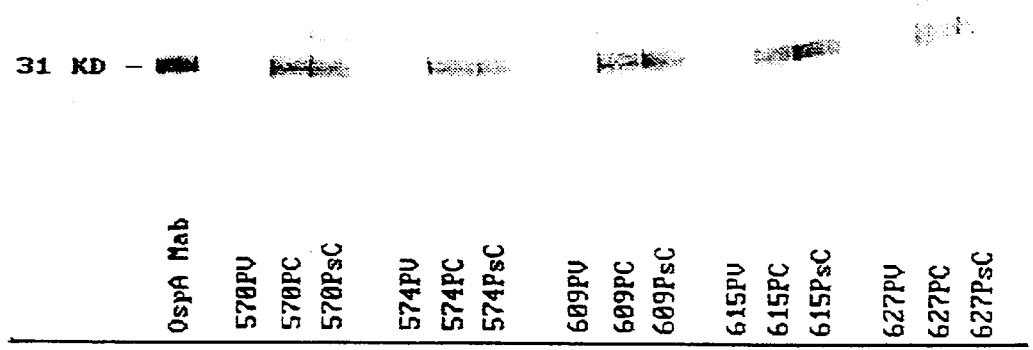
FIGS. 9A and 9B. Western Immunoblots of vaccinate serum collected at first vaccination (PV), seven months post second vaccination pre-tick challenge (PC), and eight weeks post tick challenge (PsC) against isolates S-1-10 (FIG. 9A) and C-1-11 (FIG. 9B).
Figure 9B:
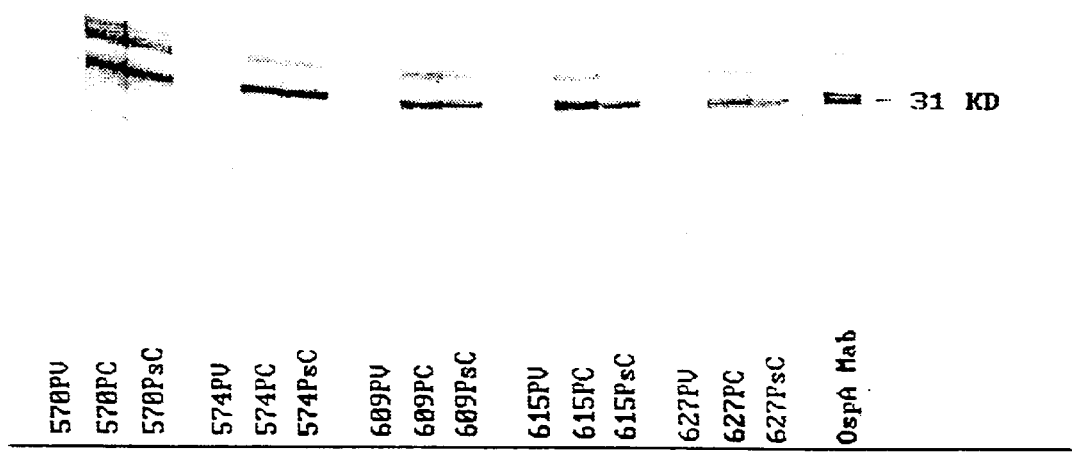
Figure 10A:
FIGS. 10A and 10B. Western Immunoblots of vaccinate serum collected at first vaccination (PV), seven months post second vaccination pre-tick challenge (PC), and eight weeks post tick challenge (PsC) against isolates S-1-10 (FIG. 10A) and C-1-11 (FIG. 10B).
Figure 10B:
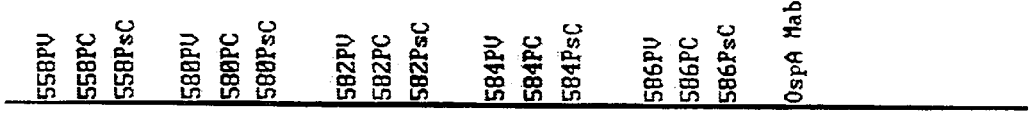
Figure 11A:
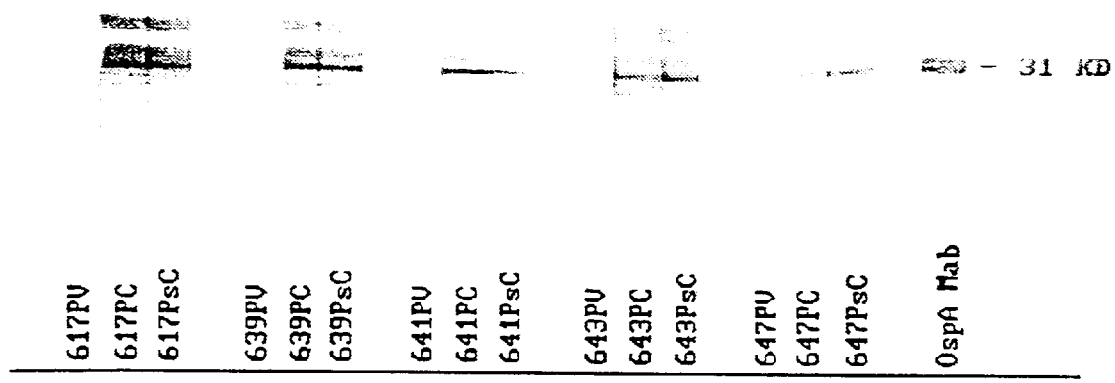
FIGS. 11A and 11B. Western Immunoblots of vaccinate serum collected at first vaccination (PV), seven months post second vaccination pre-tick challenge (PC), and eight weeks post tick challenge (PsC) against isolates S-1-10 (FIG. 11A) and C-1-11 (FIG. 11B).
Figure 11B:
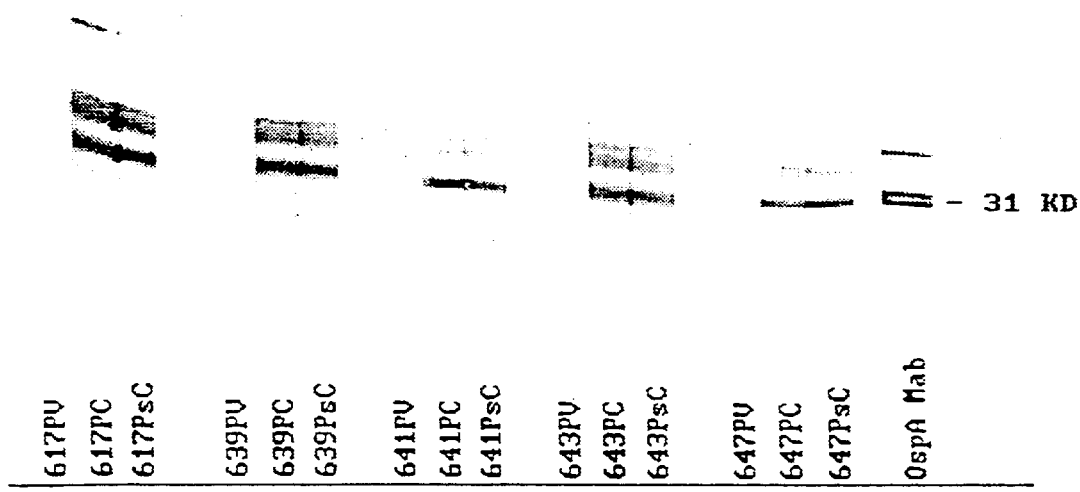
Figure 13A:
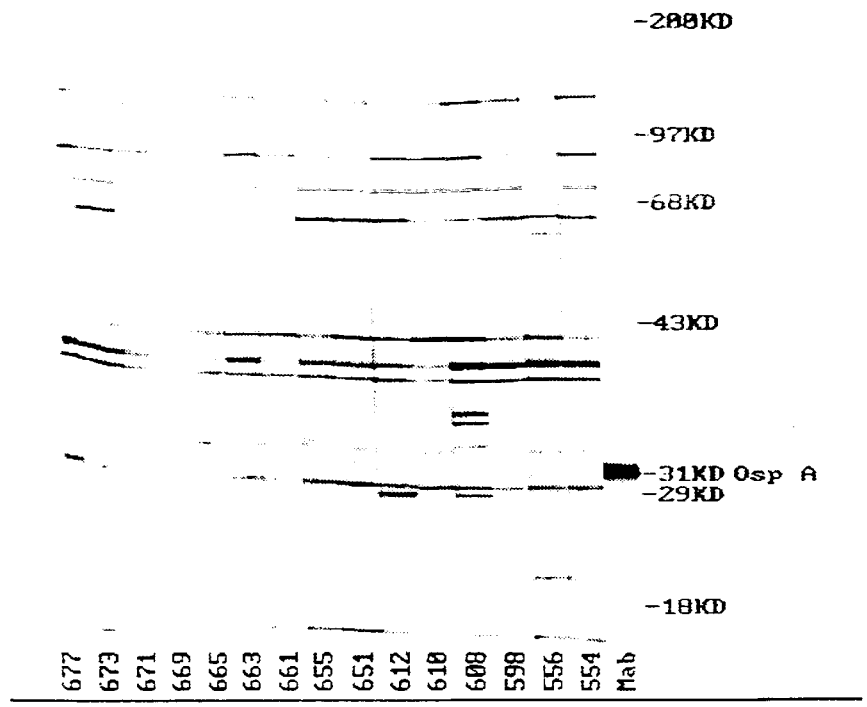
FIGS. 13A and 13B. Western Immunoblots of nonvaccinate serum collected at eight weeks post tick challenge (PsC) against isolates S-1-10 (FIG. 13A) and C-1-11 (FIG. 13B).
Figure 13B:
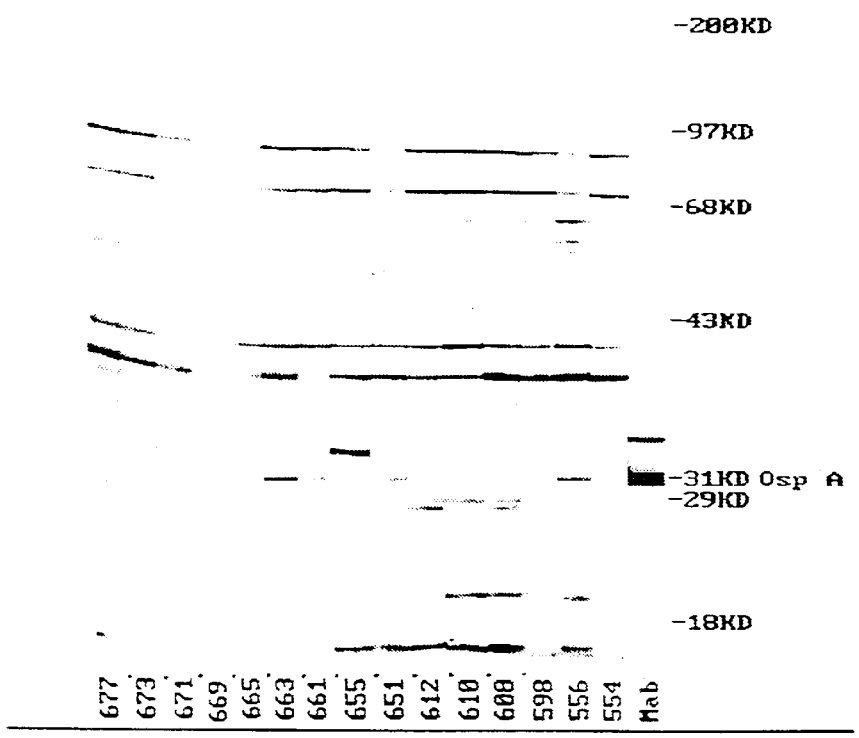

Sera from vaccinated and nonvaccinated control dogs were tested before and after challenge to determine the reactivity of the antibody with specific antigens of *B. burgdorferi*. All dogs were seronegative prior to vaccination. At seven months after the second vaccination, serum from vaccinated dogs contained antibody that reacted predominantly against the Osp A (31 kilodalton) protein and a 34 kilodalton protein corresponding to the molecular weight reported for Osp B (FIGS. 1 through 4). Antibody reacted to nearly the same extent to these proteins from S-1-10 and C-1-11. However, differences in the staining pattern and relative mobility of proteins indicated distinct differences in the proteins between the two strains. Antibodies to other proteins of *B. burgdorferi* such a flagellin (41 kilodalton) and higher molecular weight proteins were detected in the serum of some vaccinates. After tick challenge, there was little change in the immunoblot profile of vaccinated dogs. Antibody from vaccinated dogs reacted primarily to the Osp A and Osp B proteins. The antibody immunoblot profile from nonvaccinated control dogs after tick challenge was different than the immunoblot profile from vaccinated dogs. Nonvaccinated controls were seronegative prior to challenge (FIG. 5). After challenge, nonvaccinates produced antibody to the 41 kilodalton flagellin protein and to a 39 kilodalton protein as well to higher molecular weight proteins of *B. burgdorferi* (FIG. 6). Little or no antibody to Osp A and Osp B was detected in the serum of control dogs after tick challenge. Studies have shown that nonvaccinated animals produce very little antibody to OspA and OspB after exposure to *B. burgdorferi*-infected ticks (Appel, et al. (1993); Burgdorfer, et al. (1982); Roelerig, et al. (1992); Schaible U. E. et al., (1993) Immunol. Let. 36:219–226).

D. OspA ELISA

Recombinant OspA was used in an ELISA to determine the antibody response to a major protective antigen in dogs after vaccination with the bacterin. Vaccinated dogs developed OspA antibody titers that range from 320 to 2560 after the second vaccination (Table 19). The OspA GMT was 640 after vaccination and 279 prior to challenge. Antibody to OspA was not detected in nonvaccinated control dogs at eight weeks after tick challenge.

TABLE 19

ELISA antibody response to Osp A.

| | ELISA antibody titer to recombinant Osp A[a] | | |
|---|---|---|---|
| Dog No. | Prevacc. | Post Vacc.[b] | Prechall. |
| Vaccinates | | | |
| 574 | NEG[c] | 640 | 160 |
| 586 | NEG | 320 | 160 |
| 615 | NEG | 640 | 320 |
| 627 | NEG | 2560 | 320 |
| 639 | NEG | 640 | 320 |
| 558 | NEG | 320 | 160 |
| 560 | NEG | 1280 | 320 |
| 562 | NEG | 640 | 320 |
| 564 | NEG | 640 | 320 |
| 566 | NEG | 1280 | 640 |
| 568 | NEG | 320 | 320 |
| 570 | NEG | 1280 | 320 |
| 580 | NEG | 320 | 320 |
| 582 | NEG | 320 | 160 |
| 584 | NEG | 640 | 80 |
| 609 | NEG | 640 | 320 |
| 617 | NEG | 320 | 320 |
| 641 | NEG | 640 | 320 |
| 643 | NEG | 1280 | 640 |
| 647 | NEG | 640 | 320 |
| GMT[d] | NEG | 640 | 279 |
| Nonvaccinates | | | |
| 598 | NEG | NEG | NEG |
| 655 | NEG | NEG | NEG |
| 663 | NEG | NEG | NEG |
| 669 | NEG | NEG | NEG |
| 677 | NEG | NEG | NEG |
| 610 | NEG | NEG | NEG |
| 612 | NEG | NEG | NEG |
| 651 | NEG | NEG | NEG |
| 661 | NEG | NEG | NEG |
| 671 | NEG | NEG | NEG |
| 673 | NEG | NEG | NEG |
| 554 | NEG | NEG | NEG |
| 556 | NEG | NEG | NEG |
| 608 | NEG | NEG | NEG |

TABLE 19-continued

ELISA antibody response to Osp A.

| | ELISA antibody titer to recombinant Osp A[a] | | |
|---|---|---|---|
| Dog No. | Prevacc. | Post Vacc.[b] | Prechall. |
| 665 | NEG | NEG | NEG |
| GMT | NEG | NEG | NEG |

[a]Antibodies to recombinant Osp A protein bound to plate wells.
[b]Three weeks post second vaccination.
[c]Negative-correlates to a titer <1:20.
[d]Geometric mean titer.

E. Borreliacidal Antibody Response.

The functional activity of antibody generated to *B. burgdorferi* as a result of vaccination with the bacterin was measured in the borreliacidal antibody assay. Borreliacidal antibody was demonstrated by the inhibition of growth of *B. burgdorferi* as a result of antibody-mediated lysis of the organism. Vaccinated dogs developed high titers of borreliacidal antibody to both. S-1-10 and C-1-11 (Table 20). The borreliacidal GMT was 520 against the S-1-10 strain and 1,076 against the C-1-11 strain. Similar to the whole cell and OspA antibody response, borreliacidal antibody titers decreased from the second vaccination to the time of challenge. At the time of challenge, seven months after the second vaccination, borreliacidal titers of 113 and 279 for S-1-10 and C-1-11, respectively, were detected in the vaccinates. Vaccinated dogs also generated borreliacidal antibody to a different strain of *B. burgdorferi* in the same seropositive group as S-1-10 (Table 21). Borreliacidal antibody was not detected in any nonvaccinated control dogs before or after challenge. The absence of borreliacidal antibody in control dogs after challenge is similar to the results that showed OspA antibody was not detected by the OspA ELISA and immunoblotting in control dogs after challenge.

TABLE 20

Borreliacidal antibody response.

| | Prevaccination | | Post Vaccination[a] | | Pre-challenge | | 10 Wks. Post Challenge | |
|---|---|---|---|---|---|---|---|---|
| Dog. No. | C-1-11[b] | S-1-10[b] | C-1-11 | S-1-10 | C-1-11 | S-10-10 | C-1-11 | S-1-10 |
| Vaccinates | | | | | | | | |
| 574 | NEG[c] | NEG | 1280 | 640 | 320 | 20 | ND[d] | ND |
| 586 | NEG | NEG | 640 | 640 | 80 | 160 | ND | ND |
| 615 | NEG | NEG | 1280 | 640 | 320 | 80 | ND | ND |
| 627 | NEG | NEG | 2560 | 1280 | 320 | 160 | ND | ND |
| 639 | NEG | NEG | 1280 | 320 | 320 | 320 | ND | ND |
| 558 | NEG | NEG | >2560 | 640 | 320 | 80 | ND | ND |
| 560 | NEG | NEG | 1280 | 1280 | 160 | 160 | ND | ND |
| 562 | NEG | NEG | >2560 | 640 | 320 | 160 | ND | ND |
| 564 | NEG | NEG | 1280 | 320 | 320 | 320 | ND | ND |
| 566 | NEG | NEG | 1280 | 80 | 320 | 80 | ND | ND |
| 568 | NEG | NEG | 1280 | 640 | 640 | 160 | ND | ND |
| 570 | NEG | NEG | >2560 | 320 | 320 | 160 | ND | ND |
| 580 | NEG | NEG | 640 | 320 | 320 | 160 | ND | ND |
| 582 | NEG | NEG | 640 | 320 | 320 | 80 | ND | ND |
| 584 | NEG | NEG | 320 | 640 | 80 | 80 | ND | ND |
| 609 | NEG | NEG | 1280 | 640 | 160 | 320 | ND | ND |
| 617 | NEG | NEG | 320 | 640 | 320 | 160 | ND | ND |
| 641 | NEG | NEG | 640 | 640 | 320 | 40 | ND | ND |
| 643 | NEG | NEG | 1280 | 1280 | 640 | 320 | ND | ND |
| 647 | NEG | NEG | 640 | 640 | 320 | 320 | ND | ND |
| GMT[e] | NEG | NEG | 1076 | 520 | 279 | 113 | ND | ND |
| Nonvaccinates | | | | | | | | |
| 598 | ND | ND | NEG | NEG | NEG | NEG | ND | NEG |
| 655 | NEG | NEG | NEG | NEG | NEG | NEG | ND | NEG |
| 663 | NEG | NEG | NEG | NEG | NEG | NEG | ND | NEG |
| 669 | ND | ND | NEG | ND | NEG | NEG | ND | NEG |
| 677 | ND | ND | NEG | NEG | NEG | ND | ND | NEG |
| 610 | ND | ND | NEG | NEG | NEG | NEG | ND | NEG |
| 612 | ND | ND | NEG | NEG | NEG | NEG | ND | NEG |
| 651 | NEG | NEG | NEG | NEG | NEG | NEG | ND | NEG |
| 661 | NEG | NEG | NEG | NEG | NEG | NEG | ND | NEG |
| 671 | ND | ND | NEG | NG | NEG | ND | ND | NEG |
| 673 | ND | ND | NEG | NEG | NEG | NEG | ND | NEG |
| 554 | NEG | NEG | NEG | NEG | NEG | NEG | ND | NEG |
| 608 | ND | ND | NEG | NEG | NEG | NEG | ND | NEG |
| 665 | NEG | NEG | NEG | NEG | NEG | NEG | ND | NEG |

[a]Three weeks post second vaccination
[b]Borreliacidal antibody titers against C-1-11 or S-1-10.
[c]Negative-correlates to a titer <1:20
[d]Not done.
[e]Geometric mean titer.

TABLE 21

Borreliacidal antibody response to homologous and heterologous isolates of *B. burgdorferi*.

| | Pre-challenge | | |
|---|---|---|---|
| Dog No. | C-1-11 | S-1-10 | 297[a] |
| Vaccinates | | | |
| 574 | 320 | 20 | 16 |
| 586 | 80 | 160 | 32 |
| 615 | 320 | 80 | 16 |
| 627 | 320 | 160 | 64 |
| 639 | 320 | 320 | 64 |
| 558 | 320 | 80 | 32 |
| 560 | 160 | 160 | 32 |
| 562 | 320 | 160 | 64 |
| 564 | 320 | 160 | 64 |
| 566 | 320 | 80 | 64 |
| 568 | 640 | 160 | 128 |
| 570 | 320 | 160 | 32 |
| 580 | 320 | 160 | 128 |
| 582 | 320 | 80 | 16 |
| 584 | 80 | 80 | 16 |
| 609 | 166 | 320 | 128 |
| 617 | 320 | 160 | 128 |
| 641 | 320 | 40 | 32 |
| 643 | 640 | 320 | 256 |
| 647 | 320 | 20 | 16 |
| GMT[b] | 279 | 113 | 66 |
| Nonvaccinates | | | |
| 598 | NEG[c] | NEG | NEG |
| 655 | NEG | NEG | NEG |
| 663 | NEG | NEG | NEG |
| 669 | NEG | NEG | NEG |
| 677 | NEG | ND[d] | NEG |
| 610 | NEG | NEG | NEG |
| 612 | NEG | NEG | NEG |
| 651 | NEG | NEG | NEG |
| 661 | NEG | NEG | NEG |
| 671 | NEG | NEG | NEG |
| 673 | NEG | ND | NEG |
| 554 | NEG | NEG | NEG |
| 556 | NEG | NEG | NEG |
| 608 | NEG | NEG | NEG |
| 665 | NEG | NEG | NEG |

[a]Connecticut human cerebral spinal fluid isolate.
[b]Geometric mean titer.
[c]Negative-correlates to a titer <1:20 for isolates C-1-11 and S-1-10 and <1:16 for isolate 297.
[d]Not done.

F. Challenge of dogs with *B. burgdorferi*-infected ticks

A total of 1,363 *I. scapularis* ticks (732 female and 631 male) were collected from around the Ettrick, Wis. area. The infection rate in ticks with *B. burgdorferi* was found to be 44% as determined by FA analysis of midguts from male ticks. This infection rate is similar to the 47% infection rate reported by Lacombe and associates (Lacowbe, E, et al., (1993) J. Infect. Dis. 167:1236–1238). Calculations were performed to determine the probability that at least one infected tick was placed on each dog at the time of challenge. Results showed there was 99.4% probability that the last of the 35 challenged dogs received at least one infected tick (Table 22). At the time of challenge, 10 female and 6 male ticks were placed on each dog and allowed to feed for one week. In general, ticks attached within 24 hours and most ticks fed to complete or near complete engorgement during the one week challenge period. Ticks that had dropped off the dog were held in the dish. At the end of the one week tick attachment period, recovered ticks were analyzed by FA for the presence of *B. burgdorferi*. Ticks were recovered from 18 to 20 vaccinates and at least one *B. burgdorferi*-infected tick was recovered from 8 of the 18 (44%). Ticks were recovered from 14 to 15 nonvaccinated dogs and 12 of 14 (86%) were *B. burgdorferi* positive. Fikrig has (15) also reported that fewer infected ticks are recovered from vaccinated animals than nonvaccinated animals (Fikrig, E. et al. (1992) P.N.A.S. 89:5418–5421).

G. Recovery of *B. burgdorferi* from Skin Biopsy Samples

Isolation of *B. burgdorferi* from the skin of animals has been used as an indicator of *B. burgdorferi* infection. Therefore, skin biopsies were taken from anesthetized dogs at 18 days after tick challenge to demonstrate infection with *B. burgdorferi*-infected ticks. *B. burgdorferi* was isolated from the skin of 1 out of 20 (5%) of the vaccinated dogs compared to 14 to 15 (93%) of the nonvaccinated controls (Table 23).

TABLE 22

| Order of Dogs Infected | POPULATION | | New Rate | Theoretical # of infected tick placed on the dog | Probability of at least 1 infected tick |
|---|---|---|---|---|---|
| | Infected Ticks | Total Ticks | | | |
| 1 | 322 | 732 | 44.0% | 5 | 0.9971 |
| 2 | 317 | 722 | 43.9% | 5 | 0.9974 |
| 3 | 312 | 712 | 43.8% | 5 | 0.9970 |
| 4 | 307 | 702 | 43.7% | 5 | 0.9970 |
| 5 | 302 | 692 | 43.6% | 5 | 0.9969 |
| 6 | 297 | 682 | 43.5% | 5 | 0.9969 |
| 7 | 292 | 672 | 43.5% | 5 | 0.9968 |
| 8 | 287 | 662 | 43.4% | 5 | 0.9968 |
| 9 | 282 | 652 | 43.3% | 5 | 0.9967 |
| 10 | 277 | 642 | 43.1% | 5 | 0.9967 |
| 11 | 272 | 632 | 43.0% | 5 | 0.9965 |
| 12 | 267 | 622 | 42.9% | 5 | 0.9965 |
| 13 | 262 | 612 | 42.8% | 5 | 0.9965 |
| 14 | 257 | 602 | 42.7% | 5 | 0.9964 |
| 15 | 252 | 592 | 42.6% | 5 | 0.9963 |
| 16 | 247 | 582 | 42.4% | 5 | 0.9962 |
| 17 | 242 | 572 | 42.3% | 5 | 0.9962 |
| 18 | 237 | 562 | 42.2% | 5 | 0.9961 |
| 19 | 232 | 552 | 42.0% | 5 | 0.9960 |
| 20 | 227 | 542 | 41.9% | 5 | 0.9959 |
| 21 | 222 | 532 | 41.7% | 5 | 0.9958 |
| 22 | 217 | 522 | 41.6% | 5 | 0.9956 |
| 23 | 212 | 512 | 41.4% | 5 | 0.9955 |
| 24 | 207 | 502 | 41.2% | 5 | 0.9954 |
| 25 | 202 | 492 | 41.1% | 5 | 0.9953 |
| 26 | 197 | 482 | 40.9% | 5 | 0.9951 |
| 27 | 192 | 472 | 40.7% | 5 | 0.9950 |
| 28 | 187 | 462 | 40.5% | 5 | 0.9948 |
| 29 | 182 | 452 | 40.3% | 5 | 0.9946 |
| 30 | 177 | 442 | 40.0% | 5 | 0.9944 |
| 31 | 172 | 432 | 39.8% | 4 | 0.9942 |
| 32 | 168 | 422 | 39.8% | 4 | 0.9942 |
| 33 | 164 | 412 | 39.8% | 4 | 0.9942 |
| 34 | 160 | 402 | 39.8% | 4 | 0.9942 |
| 35 | 156 | 392 | 39.8% | 4 | 0.9942 |
| Remaining | 152 | 382 | | | 0.9958 |

In Table 22, the theoretical number of infected ticks placed on the dogs was based on the current infection rate. For example, 322/732 or 44% of the ticks were theoretically infected. Thus, 40% of 10 ticks sampled rounds upto 5 infected ticks, to create a worse case scenario, with the likelihood of not having enough infected ticks for the last few dogs on the study. This number was used to assess new population infection rates for the next dog.

In the calculation of the probability of at least 1 infected tick, 10 probabilities were totalled (1 tick, 2 ticks, 3 ticks, 4 ticks, ... & 10 ticks) based on currect population of infected ticks an total ticks and total ticks left. Mathematically, a hypergeometric distribution was used to determine the probability of having 1 infected tick from a sample of 10 taken from a population of 732 ticks with 322 infected ticks. To obtain at least 1 infected tick, the probabilities of 1, 2, 3, 4, 5, 6, 7, 8, 9, & 10 ticks were calculated and totalled.

TABLE 23

Characterization of infection in vaccinates and nonvaccinates following exposure to *B. burgdorferi* infected ticks.

| Dog No. | Skin Biop[a] | Date Lameness Observed | Legs Affected | Lethargy and Fever |
|---|---|---|---|---|
| Vaccinates | | | | |
| 574 | − | − | − | − |
| 586 | + | − | − | − |
| 615 | − | Jul | 2 | − |
| 627 | − | Sep | 1 | − |
| 639 | − | − | − | − |
| 558 | − | − | − | − |
| 560 | − | − | − | − |
| 562 | − | − | − | − |
| 564 | − | − | − | − |
| 566 | − | − | − | − |
| 568 | − | − | − | − |
| 570 | − | − | − | − |
| 580 | − | − | − | − |
| 582 | − | − | − | − |
| 584 | − | − | − | − |
| 609 | − | − | − | − |
| 617 | − | − | − | − |
| 641 | − | − | − | − |
| 643 | − | − | − | − |
| 647 | − | − | − | − |
| Nonvaccinates | | | | |
| 598 | + | Jul | 4 | L |
| 655 | + | Sep | 1 | − |
| 663 | + | − | − | − |
| 669 | + | − | − | − |
| 677 | + | − | − | − |
| 610 | + | Jun | 3 | L, F |
| 612 | + | Oct | 1 | F |
| 651 | + | Jun | 1 | F |
| 661 | + | Sep | 1 | L, F |
| 671 | + | Oct | 1 | F |
| 673 | + | Sep | 1 | F |
| 554 | + | − | − | − |
| 556 | + | − | − | − |
| 608 | + | Nov | 1 | L, F |
| 665 | + | Nov | 1 | F |

[a]Skin biopsies collected at tick bite sites two weeks following tick attachment.

H. Development of Lameness in Dogs Post Challenge

The primary clinical sign of Lyme disease in dogs is lameness. Protection of dogs against Lyme disease was assessed by a significant reduction in the number of lame dogs between vaccinates and controls. Dogs have now been observed for lameness on a daily basis for seven months after tick challenge. The number of dogs that have exhibited lameness and associated clinical signs are presented in Table 23. Lameness was observed in two vaccinated dogs. One limb was affected in the one vaccinate and two limbs were affected in the other vaccinate. Ten nonvaccinated controls exhibited lameness with associated lethargy and/or fever in 9 of the 10 dogs. Three limbs were affected in the one control dog. Lameness appeared more severe in nonvaccinated dogs in that the dogs were reluctant to bear any weight on the affected limb. In the majority of the nonvaccinated dogs, the affected joints were swollen and warm to the touch.

Figure 14:
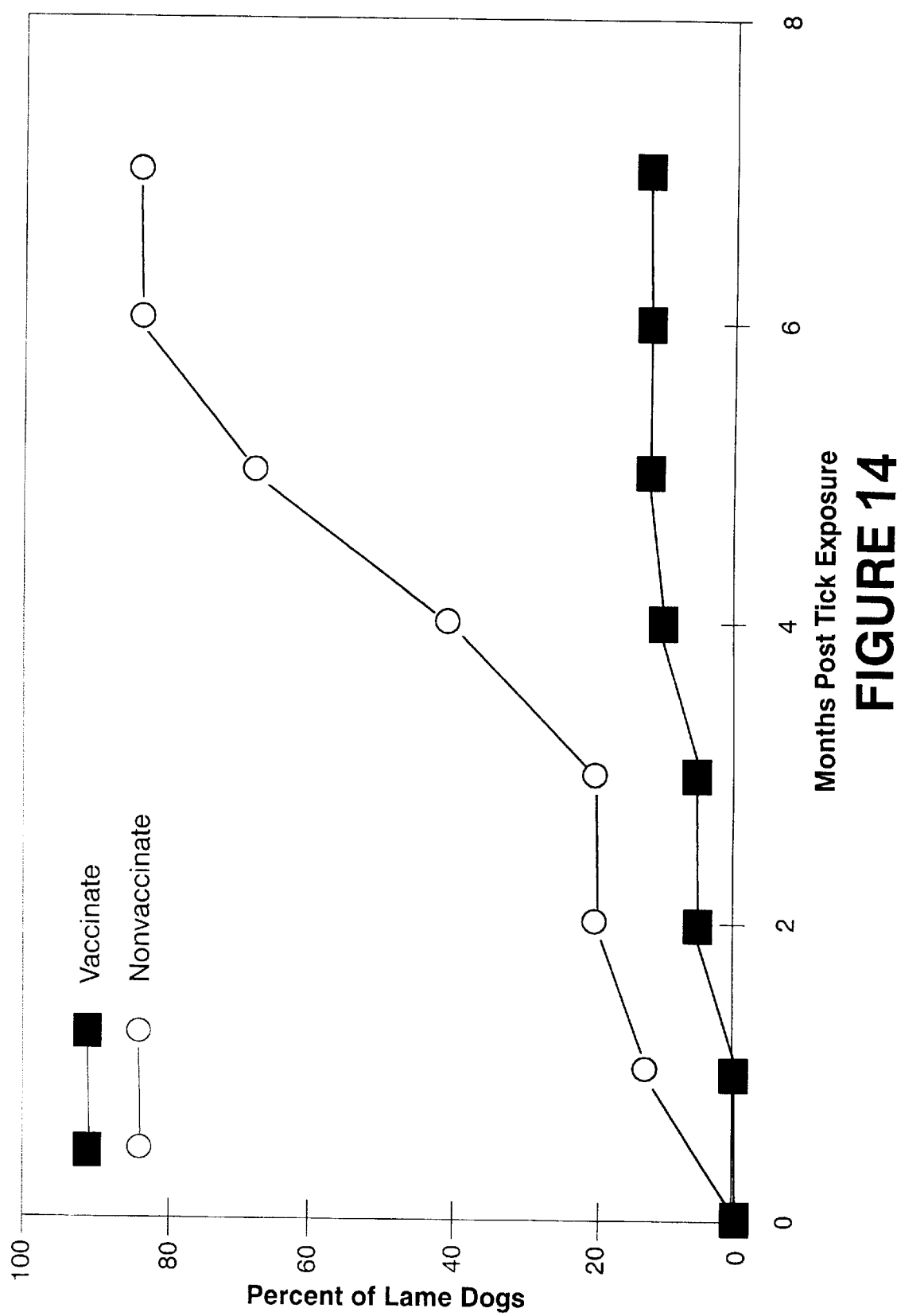
FIG. 14. Summary of percentage of dogs that exhibited lameness after tick exposure monitored for seven months.
Figure 19A:
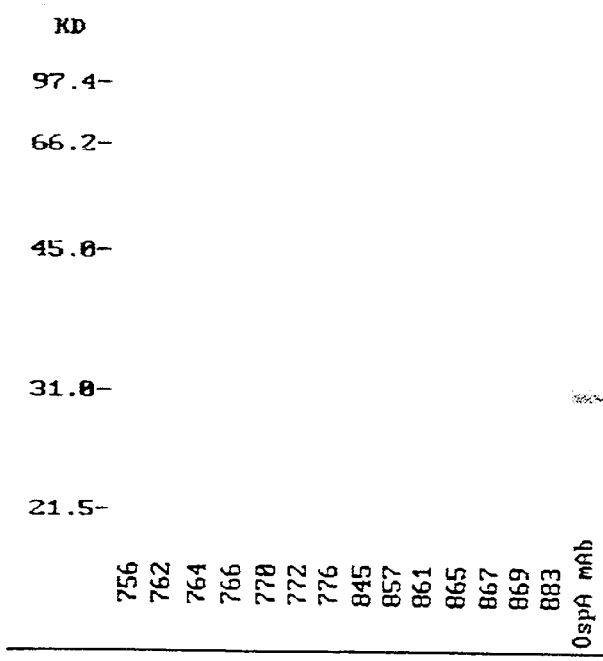
FIGS. 19A and 19B. Western immunoblots (isolate S-1-10) of serum collected from nonvaccinated controls at the time of tick challenge (FIG. 19A) and twelve weeks post tick challenge (FIG. 19B).
Figure 19B:
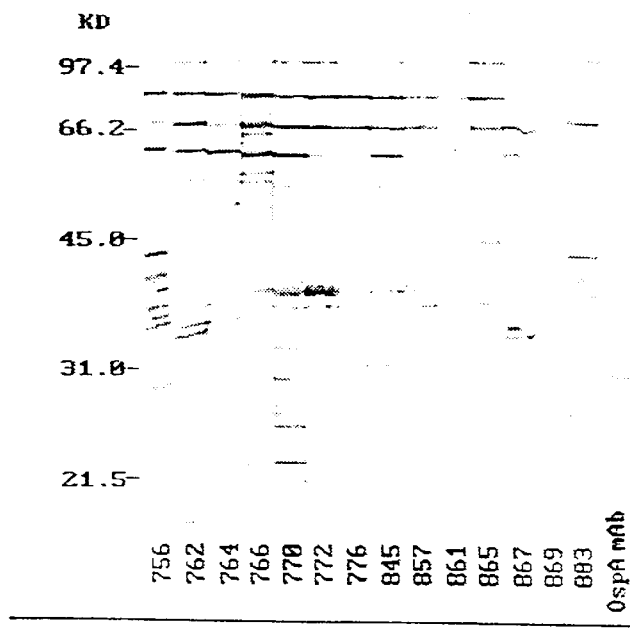
Figure 20:
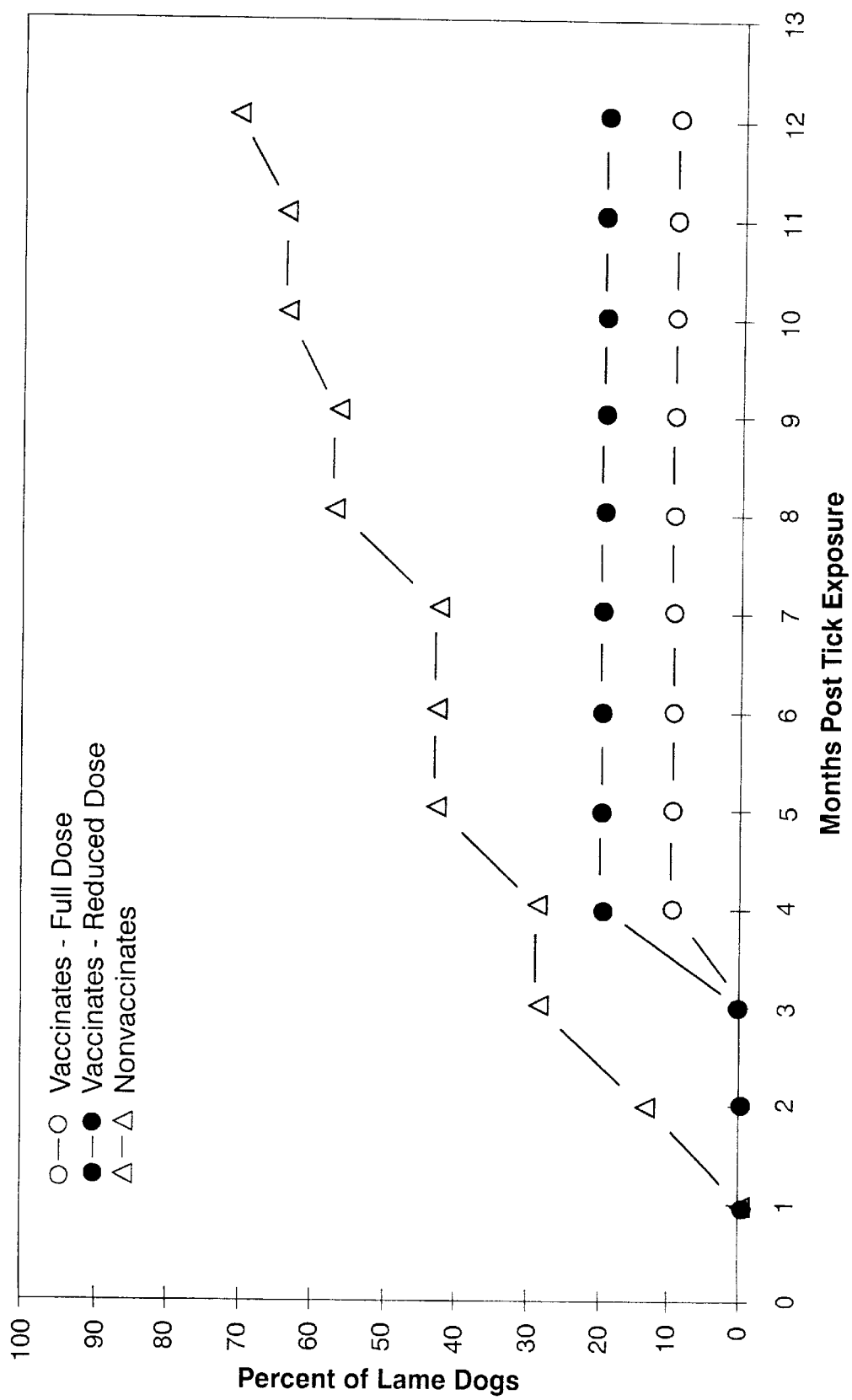
FIG. 20. Summary of percentage of dogs that exhibited lameness after tick exposure monitored for twelve months.

The temporal observation of lameness in dogs post challenge is presented in Table 24. Lameness was first observed in dogs at approximately two months after tick challenge. At this time, one vaccinate and two control dogs exhibited lameness. By the beginning of September, four months after challenge, lameness had been observed in one additional vaccinated dog and four additional control dogs. Since it was not known whether lameness would develop in any additional dogs, the decision was made to necropsy five vaccinates and five nonvaccinates to determine whether *B. burgdorferi* could be isolated from the dogs. Recovery of the spirochete from the nonlame dogs would indicate the survival of the organism in the dogs but without clinical signs presented. Two of the five dogs in each group had exhibited lameness and three dogs in each group had remained normal. Because three dogs had been removed from each test group population, the number of dogs in the vaccinate and nonvaccinated control group was reduced to 17 and 12, respectively. By seven months after tick challenge, lameness was observed in a total of 2 of 17 (12%) vaccinates and 10 of 12 (83%) nonvaccinated controls. This is calculated as a protective index score of 85.6% and represents a significant reduction ($p \leq 0.01$) in clinical disease between vaccinates and controls. A summary of the percentage of dogs that exhibited lameness after challenge is presented in FIG. 14.

Attempts were made to necropsy lame dogs within three to four days of the episode of lameness for isolation of *B. burgdorferi* from the skin, joints and organs of the dogs (Table 25). *B. burgdorferi* was not isolated from the skin, joints or organs from either of the two lame vaccinated dogs but was isolated from the skin and joint of the nonlame vaccinate that was initially skin biopsy positive. In contrast, *B. burgdorferi* was isolated from skin biopsy samples taken at necropsy from either the tick bite site or sites distant to the tick bite site from all nonvaccinated control dogs that were lame. The spirochete was also isolated from either joints or organs of all lame nonvaccinated control dogs. The nonvaccinated control dog that was initially skin biopsy negative remained skin biopsy negative at the time of necropsy and *B. burgdorferi* was not recovered from joints or organs of the dog.

TABLE 24

Numbers of dogs exhibiting lameness following tick challenge.

| Group | May | June | July | Aug | Sept | Oct | Nov | Dec | Jan | Feb |
|---|---|---|---|---|---|---|---|---|---|---|
| Vaccinates | 0/20 | 0/20 | 1/20 | 1/20 | 2/20 | 2/17 | 2/17 | 2/17 | 2/17 | 2/17 |
| Nonvaccinates | 0/15 | 2/15 | 3/15 | 3/15 | 6/15 | 8/12 | 10/12 | 10/12 | 10/12 | 10/12 |

TABLE 25

Recovery of B. burgdorferi from lame dogs.

| Dog No. | Skin Biop[a] | Date Lamenes Observe | Reisolation of B. burgdorferi at Lameness/Necropsy | | |
|---|---|---|---|---|---|
| | | | Skin | Joints | Organs[b] |
| Vaccinates | | | | | |
| 574 | − | − | − | − | − |
| 586 | + | − | + | + | − |
| 615 | − | Jul | − | − | − |
| 627 | − | Sep | − | − | − |
| 639 | − | − | − | − | − |
| 558 | − | − | | | |
| 560 | − | − | | | |
| 562 | − | − | | | |
| 564 | − | − | | | |
| 566 | − | − | | | |
| 568 | − | − | | | |
| 570 | − | − | | | |
| 580 | − | − | | | |
| 582 | − | − | | | |
| 584 | − | − | | | |
| 609 | − | − | | | |
| 617 | − | − | | | |
| 641 | − | − | | | |
| 643 | − | − | | | |
| 647 | − | − | | | |
| Nonvaccinates | | | | | |
| 598 | + | Jul | + | + | − |
| 655 | + | Sep | + | + | − |
| 663 | + | − | + | + | − |
| 669 | − | − | − | − | − |
| 677 | + | − | + | + | +[B] |
| 610[c] | + | Jun | + | + | +[B,H,K] |
| 612 | + | Oct | −/+[d] | + | − |
| 651 | + | Jun | + | + | +[S] |
| 661 | + | Sep | + | + | − |
| 671 | + | Oct | +/+ | + | − |
| 673 | + | Sep | +/+ | + | − |
| 554 | + | − | | | |
| 556 | + | − | | | |
| 608 | + | Nov | −/+ | + | +[H] |
| 665 | + | Nov | +/+ | + | − |

[a]Skin Biopsies collected at tick bite sites two weeks following tick attachment.
[b]Bladder/Heart/Kidney/Spleen
[c]B. burgdorferi was also isolated from the cerebral spinal fluid.
[d]Biopsy taken at tick bite site/Biopsy taken at a distant site to the tick bite site.

III. DISCUSSION

The humoral immune response has been shown to play a critical role in protection of animals against Lyme disease (Barthold, S. W. et al. (1993) Infect. Immunol. 61:4696–4702; Callister, et al. (1991); Callister, et al. (1992); Johnson, et al. (1986); Johnson, et al. (1986); Johnson, et al. (1988); Kochi, et al. (1988); Schaible, U. E. et al. (1990) P.N.A.S. 87:3768–3722; Schmitz, et al. (1991)). In this study, several serological assays were used to characterize the antibody response in dogs vaccinated with the bacterin. The whole cell ELISA was used to demonstrate the antibody response to surface antigens of B. burgdorferi. The development of antibody titers that persisted for seven months post vaccination provide evidence as to the antigenicity of the bacterin. Specificity of the antibody response was shown by western immunoblotting. At the time of challenge, seven months post vaccination, antibody in the serum of vaccinated dogs was primarily reactive to OspA and OspB surface proteins. Other investigators have also shown that the predominant antibody response to in vitro cultured B. burgdorferi is to the outer surface proteins (Appel, et al. (1993); Gern, L. et al. (1993) J. Infect. Dis. 167:971–975; Roerhign et al. (1992)). The OspA ELISA further demonstrated the presence of high titer antibody in the serum of vaccinated dogs and confirmed the ability of the bacterin to generate an antibody response to a protective antigen of the spirochete.

The borreliacidal antibody assay was used to demonstrate the functional activity of antibody to B. burgdorferi in the serum from vaccinated dogs. Antibody-mediated lysis of borrelia results from the combination of specific immune antibody with complement components and the formation of the membrane attack complex. The growth-inhibitory effect of antibody-mediated lysis of B. burgdorferi can be thought of as analogous to virus-neutralizing antibody. Studies have shown that the protection of laboratory animals from Lyme disease, correlates with the borreliacidal antibody titers (Jobe, D. A. et al., (1994) J. Clin. Microbiol. 32:618–22; Lourich, S. D. et al. (1991) Infect. Immunol. 59:2522–2528)). Therefore, the presence of borreliacidal antibody in vaccinated dogs can be used to demonstrate the immunogenicity of the bacterin. High levels of borreliacidal antibody were present in all vaccinated dogs and were still detectable at the time of challenge, seven months post vaccination. Antibody in the vaccinates were also borreliacidal for the heterologous B. burgdorferi 297 strain. Results showing that the antibody from nonvaccinated control dogs after challenge did not react with OspA and was not borreliacidal suggest that much of the borreliacidal activity is due to antibody reactive with OspA and other protective surface proteins. Callister and associates have shown that borreliacidal activity of antibody to B. burgdorferi in human serum can be adsorbed with recombinant OspA protein (Callister, S. M. et al. (1992)). Thus, dogs vaccinated with the bacterin developed a protective antibody response to different strains other than one of the vaccine strains.

In this study, a natural tick-challenge model similar to that reported by Appel and colleagues (Appel et al. (1993)). was used to induce Lyme disease in dogs. The model used represented the natural route of exposure, dosage and virulence of the B. burgdorferi encountered under natural field conditions.

Ticks used in this study were collected from a Lyme disease endemic area and were found to have an infection rate with B. burgdorferi of 44%. This infection rate is similar to that reported by Lacombe (Lacombe et al. (1993)) but lower than that reported by Appel (Appel et al. (1993). Shih and Spielman have shown that infected ticks transmit B. burgdorferi to mice after feeding for as little as 2 days (Shih C. et al., (1993) J. Clin. Microbiol. 31:2878–2881). Therefore, the one week time period of tick feeding used in this study would appear more than adequate. In fact, the effectiveness of the challenge was demonstrated in two ways. The whole cell ELISA detected a serological response to B. burgdorferi in 14 of 15 nonvaccinated control dogs after challenge. The results correlated with the skin biopsy results in that the one dog with little or no serological response was the same dog that was skin biopsy negative after challenge and skin biopsy negative at necropsy. It is interesting to note that fewer B. burgdorferi-infected ticks were recovered from vaccinated dogs than from nonvaccinated control dogs. These findings are similar to Fikrig and colleagues (Frikig et al., P.N.A.S. (1992)). These authors postulated that the reduced number of B. burgdorferi in ticks from vaccinated dogs was due to antibody-enhanced clearance of the spirochete.

Lameness is the primary manifestation of Lyme borreliosis in the dog, and in this study was used as the main criterion for clinical disease. After challenge, the temporal development of lameness in dogs varied during the seven months post challenge period. Lameness was observed in two nonvaccinated control dogs one month after challenge. However, the majority of the episodes of lameness did not occur until four to five months post challenge. Appel also reported that lameness in dogs did not appear until two to five months post challenge (Appel, et al. (1993)). Ten out of twelve nonvaccinated control dogs that were skin biopsy positive after challenge became lame and B. burgdorferi was reisolated from the skin and joints or other organs from all of these dogs. The finding that B. burgdorferi remained in the skin of these dogs as long as seven months post challenge and at sites completely distant to the tick bite site highlights the evolutionary development of the parasite to assure the transmission from host to host. B. burgdorferi was not reisolated from the two vaccinated dogs that became lame. Lameness in the two dogs cannot be explained on the basis of the humoral response. Other possible explanation include the genetic predisposition of the dogs, the dosage of spirochetes and efficiency of transmission from the ticks. Although B. burgdorferi has been extensively studied in the past few years, the pathogenic mechanisms of the organisms are not well characterized. The ability of other Borrelia species to become sequestered in immunological privileged sites of the host and evade defense mechanisms is well known (Geogitis, K. et al. (1992) J. Infect. Dis. 166:440–444; Levy et al. (1992); Ramachandra, R. N. et al. (1992) J. Med. Entomol, 29:818–826), and this has been postulated for B. burgdorferi.

Efficacy of the bacterin was assessed by a significant reduction in lameness between vaccinated and nonvaccinated dogs challenged with B. burgdorferi-infected ticks. The overall occurrence of lameness of 2 out of 17 (12%) vaccinates compared to 10 out of 12 (83%) nonvaccinated controls calculated to a protective index score of 86%. This represented a significant ($p \leq 0.01$) reduction in the development of clinical Lyme disease between vaccinates and controls.

Safety of the bacterin was demonstrated in this study. Efficacy and duration of immunity was shown by the ability of the vaccine to reduce the development of clinical disease in vaccinated dogs versus controls at seven months after challenge with B. burgdorferi-infected ticks.

In the comparison of the results of Example 13 and Example 14, it is believed that Example 14 provides the better results due to the use of more ticks and healthier ticks and better skin biopsies in Example 14. As a result, control dogs were shown to have clinical signs of lyme disease and, therefore, a reduction in clinical signs is shown in vaccinates versus controls using the bacterin of this invention.

Example 15

Reduced Dosage Study

I. Materials and Methods

A. Dogs

Beagles from the colony located at Solvay Animal Health, Inc., Charles City, Iowa were used in the study. The mean age of the dogs at the time of vaccination was 13 weeks (Table 26). All dogs were seronegative (titer <20) to B. burgdorferi as tested by a whole cell ELISA.

TABLE 26

Sex and age of dogs used in the study

| Dog No. | Sex | Date of Birth | Age (weeks) at first vac. |
|---|---|---|---|
| Vaccinates Full Dose | | | |
| 760 | F | 5-23-93 | 15 |
| 774 | F | 6-02-93 | 13 |
| 786 | M | 6-16-93 | 11 |
| 831 | M | 5-16-93 | 16 |
| 843 | M | 5-13-93 | 16 |
| 849 | M | 5-23-93 | 15 |
| 853 | M | 5-25-93 | 15 |
| 859 | M | 6-12-93 | 12 |
| 871 | M | 6-16-93 | 11 |
| 881 | M | 6-28-93 | 10 |
| Vaccinates Reduced Dose | | | |
| 746 | F | 5-16-93 | 16 |
| 758 | F | 5-23-93 | 15 |
| 768 | F | 6-02-93 | 13 |
| 782 | F | 6-12-93 | 12 |
| 835 | M | 5-16-93 | 16 |
| 847 | M | 5-23-93 | 15 |
| 851 | M | 5-25-93 | 15 |
| 855 | M | 6-02-93 | 13 |
| 863 | M | 6-12-93 | 12 |
| 879 | M | 6-28-93 | 10 |
| Non-vaccinated Controls | | | |
| 756 | F | 5-23-93 | 15 |
| 762 | F | 5-23-93 | 15 |
| 764 | F | 5-25-93 | 15 |
| 766 | F | 5-25-93 | 15 |
| 770 | F | 6-02-93 | 13 |
| 772 | F | 6-02-93 | 13 |
| 776 | F | 6-02-93 | 13 |
| 845 | M | 5-23-93 | 15 |
| 857 | M | 6-02-93 | 13 |
| 861 | M | 6-12-93 | 12 |
| 865 | M | 6-12-93 | 12 |
| 867 | M | 6-12-93 | 12 |
| 869 | M | 6-16-93 | 11 |
| 883 | M | 6-28-93 | 10 |

B. Bacterin Preparation

Two bacterins were used in the study. The full dose bacterin was prepared from B. burgdorferi S-1-10 and C-1-11 serotypes at the eighth passage from the master seed as described in Examples 1 and 2 above. This bacterin was formulated to contain $5 \times 10^8$ cells of each serotype per one ml dose and adjuvanted with 7.5% (wt/v) aluminum hydroxide (Rehydragel, HPA, Reheis Chemical Co., Berkeley Hts., N.J.). The reduced dose bacterin was prepared by diluting the full dose bacterin 1:10 in adjuvanted diluent composed of saline containing 7.5% (wt/v) aluminum hydroxide (Rehydragel HPA) and gentamicin and Nystatin as preservatives. Both bacterins were stored at 4° C. until used.

C. Vaccination

Ten dogs were vaccinated intramuscularly in the caudal thigh with two 1.0 ml doses at three weeks apart of each bacterin. After each vaccination, dogs were observed for abnormal reactions, temperatures were recorded and injection sites were palpated daily for five days. A group of fourteen nonvaccinated dogs served as controls.

D. Serology

Blood was collected before and after vaccination, and at intervals after challenge. Serum was tested for antibody to B.

*burgdorferi* by a whole cell ELISA, OspA ELISA, borreliacidal assay, and western immunoblotting.

1. Whole Cell ELISA

The antibody response in dogs to surface antigens of *B. burgdorferi* was determined by a modification of a whole cell ELISA used by the Regional Animal Health Laboratory, Baron, Wis. Late log phase cultures of *B. burgdorferi* C-1-11 and S-1-10 were inactivated with binary ethyleneimine (BEI). Wells of IMMULON 3 plates (Dynatech Laboratories, Inc., Chantilly, Va.) were coated with 0.3 µg of S-1-10 or C-1-11 whole cell antigen in sodium carbonate coating buffer. Plates were incubated in a humid chamber at 4° C. for 15 to 17 hours. The contents of the wells were discarded and unbound reactive sites were blocked by the addition of phosphate buffered saline (PBS) containing 5% nonfat dried milk (PBS-NFDM) and incubated in a humid chamber for 60 minutes at 37° C. Wells were emptied and 50 µl of test serum diluted in PBS containing 0.05% TWEEN-20 (PBS-TW) were added to duplicate wells and incubated in a humid chamber for 60 minutes at 37° C. Positive and negative canine control serum were included on each plate. Plates were washed three times with saline containing 0.05% TWEEN-20, and 50 µl aliquots of peroxidase labeled goat anti-dog IgG (Kirkegarrd & Perry Laboratories, Inc., Gaithersburg, Md.) diluted 1:1500 in PBS-TW were added per well. The plates were incubated in a humid chamber for 60 minutes at 37° C. and washed three times with PBS-TW. The substrate was prepared by dissolving 30.0 mg of O-Phenylenediarinie in a 0.051M dibasic sodium phosphate, 0.024M citric acid, 0.012% hydrogen peroxide solution and 100 µl aliquots were added to each well. The reaction was stopped with 50 µl per well of 2N sulfuric acid and the optical density of each well was determined at 490 nm in an ELISA reader. The titer was defined as the reciprocal of the last dilution that gave an optical density of 30% of the peak optical density.

2. OspA ELISA

Wells of a 96-well microtiter plate were coated with 75 ng of recombinant S-1-10 or C-1-11 OspA and incubated overnight at 4° C. Wells were post-coated with 5% NFDM in PBS for 60 minutes at 37° C. Wells were washed three times with PBS-TW and 50 µl of two-fold dilutions of dog serum were added to the wells. After incubation at 37° C. for one hour, wells were washed with PBS-TW and 50 µl of goat anti-dog IgG.HRP (Kirkegaard & Perry Laboratories, Inc., Gaithersburg, Md.) were added to the wells. Bound antibody was detected by the addition of ABTS substrate (Kirkegaard & Perry Laboratories, Inc., Gaithersburg, Md.). Optical density of each well was determined at 405 nm in an ELISA reader. The titer was defined as the reciprocal of the last dilution that gave an optical density of 30% of the peak optical density.

3. Western Immunoblotting

Mid to late log phase cultures of *B. burgdorferi* S-1-10 and C-1-11 were harvested by centrifugation at 15,000×g at 4° C. for 30 minutes. Bacteria were washed three times by centrifugation with sterile saline. Suspensions of approximately $1 \times 10^8$ cells were boiled in electrophoresis sample buffer for-nine minutes and electrophoresed on a 10% SDS-polyacrylamide gel. (Laemmli 1970). Separated proteins were electroblotted onto IMMOBILON PVDF membrane (Millipore Corp., Bedford, Mass.) by a modification of the procedure described by Towbin (Towbin et al. 1979). The PVDF membrane was incubated for 90 minutes at 22° C. in 20 mM tris, 150 mM NaCl pH 7.2 (TBS) with 5% NFDM. Strips were incubated with canine serum or monoclonal antibody to OspA diluted 1:75 in the blocking buffer for 60 minutes at 22° C. Strips were then washed two times in TBS containing 0.2% TRITON X-100 and one time in TBS. Bound antibody was detected by the addition of goat anti-canine IgG.HRP or goat anti-murine IgG.HRP (Kirkegaard & Perry Laboratories Inc., Gaithersburg, Md.). Protein bands were visualized with a TMB membrane peroxidase substrate system (Kirkegaard & Perry Laboratories Inc., Gaithersburg, Md.).

F. Detection of Borreliacidal Antibody by Flow Cytometry

The borreliacidal assay was performed using a modification of previously described procedures (6,7). Briefly, a 72 hour mid-log phase culture of *B. burgdorferi* isolate C-1-11 and S1-10 in modified Barbour Stoenner Kelly (BSK) medium was quantified in a Petroff-Hauser chamber and diluted to contain $1 \times 10^6$ cells/ml BSK medium. Aliquots of 100 µl of diluted, heat inactivated serum were mixed with 100 µl of each *B. burgdorferi* suspension and 10 µl of guinea pig serum complement (210 $CH_{50}$ units; GIBCO Laboratories, Grand Island, N.Y.) were added. The suspension was gently mixed and incubated at 32° C. for 16 to 24 hours. After incubation of the reaction tubes, 100 µl of the reaction mixture was diluted with PBS containing $5.4 \times 10^{-9}$ M acridine orange. Detection of borreliacidal activity was performed using a modification of previously described procedures. Callister et al. (1994). Killing by borreliacidal antibodies causes blebbing of *B. burgdorferi* cell walls and higher concentrations of acridine orange are adsorbed onto and into these damaged cell walls. Consequently, killed *B. burgdorferi* organisms fluoresce at a much greater intensity than normal live spirochetes. An increase in fluorescence intensity of $\geq 16\%$ compared with organisms exposed to normal dog serum was considered positive for borreliacidal activity. The end point titer was expressed as the reciprocal of the last dilution at which there was a $\geq 16\%$ increase in fluorescence intensity. Dogs with a titer of <20 were defined as seronegative.

G. Challenge

A total of 300 *I. scapularis* male and 360 female ticks were collected from a Lyme disease endemic area near Ettrick, Wis. To establish the overall *B. burgdorferi* infection rate of the ticks, the midguts of 49 male *I. scapularis* ticks were examined by fluorescent antibody assay (FA) using the OspA monoclonal antibody obtained from Dr. A. G. Barbour. At four weeks post second vaccination, each dog was challenged with 10 female and 6 male ticks. Female ticks are the only adult ticks that transmit the disease. Male ticks are needed for proper feeding of the female ticks. Five female and three male ticks were randomly selected from the pool of ticks and placed in two small petri dishes that were secured to a shaved are on the left dorsal-anterior area of the thorax of each dog. The ticks were allowed to feed for one week and observed at two day intervals. One week post attachment, ticks were recovered and the midguts examined for the presence of *B. burgdorferi* by FA with the *B. burgdorferi* monoclonal antibody.

H. Observation for Clinical Signs

Dogs were observed daily following challenge for clinical signs associated with Lyme disease. The clinical signs used as indicators of clinical Lyme disease were lameness, lethargy and fever. Lameness was defined as reluctance to bear wight on an affected limb with or without swelling and temperature at the affected joint, stiff leggedness, and the migration of lameness from joint to joint or limb to limb.

I. Isolation of *B. burgdorferi*

Samples of the skin, joints, and organs of dogs were collected for isolation of *B. burgdorferi*. Skin biopsies were taken at the tick attachment site and from sites distant to the tick bite site from anesthetized dogs at 21 days following tick attachment and at the time of necropsy. Distant sites were located ventral to the tick bite site, posterior to the tick bite site, and on the right side of the dorsal-anterior area of the thorax on the opposite side of the dog. The skin was shaved, washed with SOLVAHEX Surgical Scrub, and rinsed thoroughly with sterile water to remove residual disinfectant. An elliptical incision was made through the dermal and subcutaneous skin layers. Approximately one gram of skin was placed in nine ml BSK medium containing 0.15% agarose and 40 μg rifampin/ml. The biopsy sample was homogenized and two additional 10-fold dilutions of homogenate were made in nine ml blanks of the BSK medium. Cultures were incubated at 32° C. for six weeks and were examined microscopically at three and six weeks after inoculation for the growth of spirochetes. Cultures showing spirochete growth were confirmed as *B. burgdorferi* by FA with the *B. burgdorferi* monoclonal antibody. Cultures negative for spirochete growth after six weeks incubation were discarded. At the time of necropsy, heart, spleen, kidneys, and bladder were collected and homogenized in 50 ml BSK medium containing agarose and rifampin by the use of a STOMACHER (Seward Medical, London, England). A 50 ml sample was poured off and 10-fold dilutions were prepared in BSK medium. Cultures Were incubated for six weeks at 32° C., observed and confirmed as *B. burgdorferi* by FA. A two to three ml sample of cerebrospinal fluid was added to nine ml BSK medium and an additional 1:10 dilution was made in the same medium, incubated and observed as described. Joint tissue was taken from the elbow, carpus, knee, and tarsus. The tissue from each joint was added to nine ml BSK medium containing agarose and rifampin. An additional 1:10 dilution was made in the same medium, and cultures were incubated and observed as described.

II. RESULTS

A. Vaccination

Dogs were vaccinated with two doses of bacterin at three weeks apart. No local or systemic reactions were observed in any of the dogs. Temperatures of the dogs in both vaccination groups remained normal after the first and second dose of bacterin, Tables 27 and 28, respectively.

TABLE 27

Temperatures of dogs after first vaccination

| Dog | Temperatures (°F.) on days post vaccination | | | | | |
|---|---|---|---|---|---|---|
| | 0 | 1 | 2 | 3 | 4 | 5 |
| Vaccinates-Full dose | | | | | | |
| 746 | 100.4 | 100.6 | 100.2 | 100.2 | 100.3 | 100.3 |
| 758 | 101.4 | 101.6 | 100.6 | 101.1 | 101.7 | 100.2 |
| 768 | 100.4 | 101.1 | 100.9 | 100.8 | 101.2 | 100.4 |
| 782 | 100.8 | 100.5 | 100.7 | 101.1 | 100.2 | 100.6 |
| 835 | 101.2 | 101.1 | 100.6 | 100.9 | 100.9 | 100.6 |
| 847 | 101.8 | 100.5 | 101.6 | 101.1 | 100.1 | 100.5 |
| 851 | 100.8 | 100.9 | 100.8 | 100.6 | 101.2 | 100.2 |
| 855 | 100.8 | 101.4 | 101.7 | 100.6 | 101.3 | 100.9 |
| 863 | 100.8 | 100.1 | 101.2 | 100.8 | 101.1 | 100.5 |
| 879 | 101.1 | 101.6 | 101.9 | 101.2 | 101.2 | 102.2 |
| Vaccinates-Reduced dose | | | | | | |
| 760 | 101.3 | 101.4 | 101.1 | 100.1 | 101.1 | 101.1 |
| 774 | 101.2 | 100.9 | 100.7 | 100.1 | 100.6 | 100.4 |

TABLE 27-continued

Temperatures of dogs after first vaccination

| Dog | Temperatures (°F.) on days post vaccination | | | | | |
|---|---|---|---|---|---|---|
| | 0 | 1 | 2 | 3 | 4 | 5 |
| 786 | 100.9 | 100.2 | 100.9 | 102.1 | 101.1 | 101.0 |
| 831 | 100.7 | 100.7 | 100.1 | 101.1 | 100.5 | 101.9 |
| 843 | 101.6 | 100.6 | 101.2 | 100.4 | 100.7 | 100.0 |
| 849 | 100.7 | 100.7 | 100.4 | 100.3 | 100.2 | 100.4 |
| 853 | 101.5 | 100.3 | 100.4 | 101.6 | 100.6 | 101.2 |
| 859 | 101.9 | 100.5 | 191.4 | 101.3 | 101.1 | 102.0 |
| 871 | 100.5 | 100.1 | 101.1 | 101.6 | 100.7 | 101.1 |
| 881 | 101.1 | 101.7 | 100.8 | 101.1 | 101.4 | 101.7 |

TABLE 28

Temperatures of dogs after second vaccination.

| Dog | Temperatures (°F.) on days post vaccination | | | | | |
|---|---|---|---|---|---|---|
| | 0 | 1 | 2 | 3 | 4 | 5 |
| Vaccinates-Full dose | | | | | | |
| 746 | 102.6 | 102.1 | 103.0 | 102.2 | 102.7 | 103.0 |
| 758 | 102.2 | 102.0 | 102.8 | 101.6 | 102.7 | 102.1 |
| 768 | 101.5 | 101.9 | 102.4 | 101.8 | 102.6 | 101.8 |
| 782 | 101.9 | 101.6 | 102.0 | 102.0 | 102.3 | 102.0 |
| 835 | 102.6 | 101.7 | 103.0 | 102.2 | 102.5 | 102.2 |
| 847 | 102.0 | 102.4 | 101.7 | 101.4 | 101.9 | 101.3 |
| 851 | 102.5 | 102.1 | 102.3 | 101.7 | 102.8 | 102.1 |
| 855 | 102.1 | 102.8 | 102.4 | 101.8 | 102.3 | 102.1 |
| 863 | 101.7 | 102.0 | 101.8 | 101.7 | 102.4 | 101.9 |
| 879 | 102.0 | 102.3 | 101.9 | 101.6 | 101.7 | 101.6 |
| Vaccinates-Reduced dose | | | | | | |
| 760 | 101.3 | 101.4 | 101.1 | 100.1 | 101.1 | 101.1 |
| 774 | 101.2 | 100.9 | 100.7 | 100.1 | 100.6 | 100.4 |
| 786 | 100.9 | 100.2 | 100.9 | 102.1 | 101.1 | 101.0 |
| 831 | 100.7 | 100.7 | 100.1 | 101.1 | 100.5 | 101.9 |
| 843 | 101.6 | 100.6 | 101.2 | 100.4 | 100.7 | 100.0 |
| 849 | 100.7 | 100.7 | 100.4 | 100.3 | 100.2 | 100.4 |
| 853 | 101.5 | 100.3 | 100.4 | 101.6 | 100.6 | 101.2 |
| 859 | 101.9 | 100.5 | 101.4 | 101.3 | 101.1 | 102.0 |
| 871 | 100.5 | 100.1 | 101.1 | 101.6 | 100.7 | 101.1 |
| 881 | 101.1 | 101.7 | 100.8 | 101.1 | 101.4 | 101.7 |

B. Antibody Response to *B. burgdorferi* Whole Cell Antigens

An ELISA that used whole *B. burgdorferi* cells was used to demonstrate the serological response of vaccinated and challenged dogs to surface antigens of *B. burgdorferi*. Prior to vaccination, all dogs were seronegative. At four weeks post second vaccination, dogs vaccinated with the full dose bacterin had an antibody GMT of 788 against C-1-11 and a GMT of 520 against S-1-10 (Table 29). Dogs vaccinated with the reduced dose bacterin had a slightly lower GMT of 485 against C-1-11 and an identical GMT of 520 against S-1-10. After challenge, antibody titers to C-1-11 and S-1-10 in both bacterin groups had decreased to nearly the same level. At 12 weeks post challenge, the whole cell antibody GMT of nonvaccinated control dogs was higher than the whole cell GMT of vaccinated dogs. The GMT in nonvaccinated controls were 1502 and 2301 against C-1-11 and S-1-10, respectively. One nonvaccinated control dog remained seronegative at 12 weeks post challenge.

TABLE 29

Whole cell ELISA antibody response in dogs vaccinated with the full and reduced dose bacterins.

| | Antibody Titer to *B. burgdorferi* isolate at: | | | | | |
|---|---|---|---|---|---|---|
| | Pre-vaccination | | Pre-challenge[a] | | 12 Wks. Post-challenge | |
| Dog No. | C-1-11 | S-1-10 | C-1-11 | S-1-10 | C-1-11 | S-1-10 |
| Vaccinates Full dose | | | | | | |
| 746 | NEG[b] | NEG | 2560 | 1280 | 640 | 640 |
| 758 | NEG | NEG | 640 | 640 | 160 | 160 |
| 768 | NEG | NEG | 320 | 160 | 320 | 320 |
| 782 | NEG | NEG | 320 | 320 | 160 | 320 |
| 835 | NEG | NEG | 1280 | 1280 | 640 | 640 |
| 847 | NEG | NEG | 1280 | 640 | 640 | 640 |
| 851 | NEG | NEG | 1280 | 640 | 320 | 320 |
| 855 | NEG | NEG | 640 | 640 | 320 | 320 |
| 863 | NEG | NEG | 640 | 320 | 320 | 160 |
| 879 | NEG | NEG | 640 | 320 | 160 | 160 |
| GMT | NEG | NEG | 788 | 520 | 320 | 320 |
| Vaccinates Reduced dose | | | | | | |
| 760 | NEG | NEG | 640 | 640 | 160 | 80 |
| 774 | NEG | NEG | 320 | 320 | 80 | 80 |
| 786 | NEG | NEG | 320 | 640 | 160 | 160 |
| 831 | NEG | NEG | 640 | 1280 | 160 | 160 |
| 843 | NEG | NEG | 1280 | 640 | 640 | 320 |
| 849 | NEG | NEG | 320 | 320 | 160 | 160 |
| 853 | NEG | NEG | 640 | 640 | 320 | 320 |
| 859 | NEG | NEG | 640 | 320 | 160 | 160 |
| 871 | NEG | NEG | 320 | 640 | 160 | 160 |
| 881 | NEG | NEG | 320 | 320 | 160 | 160 |
| GMT | NEG | NEG | 485 | 520 | 184 | 160 |
| Nonvaccinated Controls | | | | | | |
| 756 | NEG | NEG | NEG | NEG | 2560 | >5120 |
| 762 | NEG | NEG | NEG | NEG | 1280 | >5120 |
| 764 | NEG | NEG | NEG | NEG | 2560 | >5120 |
| 766 | NEG | NEG | NEG | NEG | 1280 | 2560 |
| 770 | NEG | NEG | NEG | NEG | 2560 | 2560 |
| 772 | NEG | NEG | NEG | NEG | 1280 | 2560 |
| 776 | NEG | NEG | NEG | NEG | 640 | 640 |
| 845 | NEG | NEG | NEG | NEG | 2560 | 2560 |
| 857 | NEG | NEG | NEG | NEG | 640 | 1280 |
| 861 | NEG | NEG | NEG | NEG | 1280 | 2560 |
| 865 | NEG | NEG | NEG | NEG | 1280 | 1280 |
| 867 | NEG | NEG | NEG | NEG | 1280 | 1280 |
| 869 | NEG | NEG | NEG | NEG | NEG | NEG |
| 883 | NEG | NEG | NEG | NEG | 2560 | 2560 |
| GMT | NEG | NEG | NEG | NEG | 1502 | >2301 |

[a]Four weeks post second vaccination.
[b]Negative, titer <20.

C. Western Immunoblotting

Sera from vaccinated and nonvaccinated control dogs were tested before and after vaccination and challenge to determine the reactivity of the antibody with specific antigens of *B. burgdorferi*. All dogs were seronegative prior to vaccination. The antibody responses against *B. burgdorferi* C-1-11 and S-1-10 in dogs vaccinated with the full dose bacterin are presented in FIGS. 1 and 2. The antibody response was predominantly against the OspA and CspB proteins of C-1-11 and S-1-10. Dogs vaccinated with the full dose bacterin reacted to the 31 and 34 kilodalton molecular weight proteins of OspA and OspB, espectively of C-1-11 and S-1-10 to nearly the same extent. Differences in the staining patterns of C-1-11 and S-1-10 OspA proteins indicate the distinct antigenic difference between the two isolates. Minor reactivity to other proteins of the spirochete was observed in some dogs. Dogs vaccinated with the reduced dose bacterin also developed antibodies to OspA and OspB proteins of C-1-11 and S-1-10 (FIGS. 3 and 4). The staining intensity of the antibody profile in dogs vaccinated with the reduced dose bacterin indicated that the level of the OspA response was the same as in dogs that received the full dose bacterin. At 12 weeks post challenge, the antibody profile was essentially unchanged in dogs from the full dose and reduced dose bacterin groups. Reactivity to OspA and OspB remained as the major antibody response detected. However, there was little if any of an antibody response to other proteins of Borrelia after challenge. Post challenge, a decrease in the staining intensity against OspA and OspB was observed in some vaccinates but occurred in dogs from both bacterin groups. Although nonspecific staining was observed in some dogs, all nonvaccinated control dogs were seronegative to *B. burgdorferi* prior to vaccinated control dogs were seronegative to *B. burgdorferi* prior to vaccination. No reactivity to OspA and OspB was detected in any nonvaccinated control dogs (FIGS. 5 and 6). The antibody profile in control dogs after challenge differed dramatically from the antibody profile observed in vaccinated dogs after challenge. Nonvaccinated control dogs developed little if any response to OspA and OspB proteins after challenge but developed antibodies to a variety of other antigens of *B. burgdorferi*.

D. OspA ELISA

An ELISA that utilized recombinant OspA was used to determine the antibody response to a major protective antigen in dogs vaccinated with the full and reduced dose bacterins. There was no significant difference in the OspA antibody GMT to the C-1-11 or S-1-10 isolate of *B. burgdorferi* between dogs that received the full dose and reduced dose bacterins. Dogs vaccinated with the full dose bacterin developed an OspA antibody GMT of 452 for C-1-11 compared to a GMT of 368 against C-1-11 in dogs that received the reduced dose bacterin (Table 30). The OspA antibody GMT in the full dose and reduced dose bacterin groups against S-1-10 were 299 and 394, respectively. The finding that antibodies to OspA of C-1-11 and S-1-10 were not detected by ELISA in any nonvaccinated control dogs after tick challenge correlate with the lack of detection of OspA antibody by immunoblotting.

TABLE 30

ELISA antibody response in OspA in dogs vaccinated with the full dose bacterins.

| | Antibody Titer to *B. burgdorferi* isolate at: | | | | | |
|---|---|---|---|---|---|---|
| | Pre-vaccination | | Pre-challenge[a] | | 12 Wks. Post-challenge | |
| Dog No. | C-1-11 | S-1-10 | C-1-11 | S-1-10 | C-1-11 | S-1-10 |
| Vaccinates Full dose | | | | | | |
| 746 | NEG[b] | NEG | 1280 | 640 | 640 | 640 |
| 758 | NEG | NEG | 640 | 320 | 160 | 160 |
| 768 | NEG | NEG | 160 | 160 | 160 | 160 |
| 782 | NEG | NEG | 320 | 160 | 320 | 160 |
| 835 | NEG | NEG | 640 | 640 | 640 | 640 |
| 847 | NEG | NEG | 640 | 640 | 640 | 640 |
| 851 | NEG | NEG | 640 | 320 | 160 | 320 |
| 855 | NEG | NEG | 320 | 320 | 320 | 320 |
| 863 | NEG | NEG | 320 | 160 | 320 | 160 |
| 879 | NEG | NEG | 320 | 160 | 160 | 80 |
| GMT | NEG | NEG | 452 | 299 | 299 | 260 |

TABLE 30-continued

ELISA antibody response in OspA in dogs vaccinated with the full dose bacterins.

| | Antibody Titer to *B. burgdorferi* isolate at: | | | | | |
|---|---|---|---|---|---|---|
| | Pre-vaccination | | Pre-challenge[a] | | 12 Wks. Post-challenge | |
| Dog No. | C-1-11 | S-1-10 | C-1-11 | S-1-10 | C-1-11 | S-1-10 |
| Vaccinates Reduced dose | | | | | | |
| 760 | NEG | NEG | 320 | 640 | 160 | 160 |
| 774 | NEG | NEG | 320 | 320 | 160 | 80 |
| 786 | NEG | NEG | 320 | 320 | 320 | 320 |
| 831 | NEG | NEG | 640 | 640 | 320 | 160 |
| 843 | NEG | NEG | 640 | 320 | 320 | 320 |
| 849 | NEG | NEG | 326 | 320 | 160 | 160 |
| 853 | NEG | NEG | 640 | 640 | 320 | 320 |
| 859 | NEG | NEG | 320 | 320 | 160 | 160 |
| 871 | NEG | NEG | 160 | 320 | 160 | 160 |
| 881 | NEG | NEG | 320 | 320 | 160 | 160 |
| GMT | NEG | NEG | 368 | 394 | 211 | 184 |
| Nonvaccinated Controls | | | | | | |
| 756 | NEG | NEG | NEG | NEG | NEG | NEG |
| 762 | NEG | NEG | NEG | NEG | NEG | NEG |
| 764 | NEG | NEG | NEG | NEG | NEG | NEG |
| 766 | NEG | NEG | NEG | NEG | NEG | NEG |
| 770 | NEG | NEG | NEG | NEG | NEG | NEG |
| 772 | NEG | NEG | NEG | NEG | NEG | NEG |
| 776 | NEG | NEG | NEG | NEG | NEG | NEG |
| 857 | NEG | NEG | NEG | NEG | NEG | NEG |
| 861 | NEG | NEG | NEG | NEG | NEG | NEG |
| 865 | NEG | NEG | NEG | NEG | NEG | NEG |
| 867 | NEG | NEG | NEG | NEG | NEG | NEG |
| 869 | NEG | NEG | NEG | NEG | NEG | NEG |
| 883 | NEG | NEG | NEG | NEG | NEG | NEG |
| GMT | NEG | NEG | NEG | NEG | NEG | NEG |

[a]Four weeks post second vaccination.
[b]Negative, titer <20.

E. Borreliacidal Antibody Response

The functional activity of antibody generated to *B. burgdorferi* as a result of vaccination with the bacterin was measured in the borreliacidal antibody assay. Borreliacidal antibody was demonstrated by the inhibition of growth of *B. burgdorferi* as a result of antibody-mediated lysis of the organism. Dogs vaccinated with either full or reduced dose bacterin developed high titers of borreliacidal antibody to both S-1-10 and C-1-11 (Table 31). The borreliacidal antibody GMT in dogs that received the full dose bacterin was in 970 against C-1-11 compared to a 640 GMT against C-1-11 in dogs that received the reduced dose bacterin. The borreliacidal antibody GMT against S-1-10 was 597 in both bacterin groups.

TABLE 31

Borreliacidal antibody response in dogs vaccinated with the full dose and reduced dose bacterins.

| | Antibody Titer to *B. burgdorferi* isolate at: | | | |
|---|---|---|---|---|
| | Pre-vaccination | | Pre-challenge[a] | |
| Dog No. | C-1-11 | S-1-10 | C-1-11 | S-1-10 |
| Vaccinates Full dose | | | | |
| 746 | NEG[b] | NEG | 2560 | 1280 |
| 758 | NEG | NEG | 640 | 640 |

TABLE 31-continued

Borreliacidal antibody response in dogs vaccinated with the full dose and reduced dose bacterins.

| | Antibody Titer to *B. burgdorferi* isolate at: | | | |
|---|---|---|---|---|
| | Pre-vaccination | | Pre-challenge[a] | |
| Dog No. | C-1-11 | S-1-10 | C-1-11 | S-1-10 |
| 768 | NEG | NEG | 640 | 160 |
| 782 | NEG | NEG | 640 | 640 |
| 835 | NEG | NEG | 1280 | 1280 |
| 847 | NEG | NEG | 1280 | 1280 |
| 851 | NEG | NEG | 640 | 640 |
| 855 | NEG | NEG | 1280 | 640 |
| 863 | NEG | NEG | 640 | 160 |
| 879 | NEG | NEG | 1280 | 640 |
| GMT | NEG | NEG | 907 | 597 |
| Vaccinates Reduced dose | | | | |
| 760 | NEG | NEG | 1280 | 640 |
| 774 | NEG | NEG | 160 | 320 |
| 786 | NEG | NEG | 320 | 320 |
| 831 | NEG | NEG | 1280 | 1280 |
| 843 | NEG | NEG | 1280 | 640 |
| 849 | NEG | NEG | 640 | 320 |
| 853 | NEG | NEG | 1280 | 1280 |
| 859 | NEG | NEG | 640 | 640 |
| 871 | NEG | NEG | 640 | 1280 |
| 881 | NEG | NEG | 320 | 320 |
| GMT | NEG | NEG | 640 | 597 |
| Nonvaccinated Controls | | | | |
| 756 | NEG | NEG | NEG | NEG |
| 762 | NEG | NEG | NEG | NEG |
| 764 | NEG | NEG | NEG | NEG |
| 766 | NEG | NEG | NEG | NEG |
| 770 | NEG | NEG | NEG | NEG |
| 772 | NEG | NEG | NEG | NEG |
| 776 | NEG | NEG | NEG | NEG |
| 845 | NEG | NEG | NEG | NEG |
| 857 | NEG | NEG | NEG | NEG |
| 861 | NEG | NEG | NEG | NEG |
| 865 | NEG | NEG | NEG | NEG |
| 867 | NEG | NEG | NEG | NEG |
| 869 | NEG | NEG | NEG | NEG |
| 883 | NEG | NEG | NEG | NEG |
| GMT | NEG | NEG | NEG | NEG |

[a]Four weeks post second vaccination.
[b]Negative, titer <20.

F. Challenge of Dogs with *B. burgdorferi*-infected Ticks

A total 660 *I. scapularis* ticks (360 female and 300 male) were used to challenge the dogs. The infection rate in ticks with *B. burgdorferi* was found to be 45% as determined by FA analysis of midguts from male ticks. This infection rate is similar to the 44% infection rate reported in Example 14 above and, again, similar to the 47% infection rate reported by Lacombe and associates. Lacombe et al. (1993). In general, ticks attached within 24 hours and most ticks fed to complete or near complete engorgement during the one week challenge period. Ticks that had dropped off the dog were held in the dish. At the end of the one week tick attachment period, recovered ticks were analyzed by FA for the presence of *B. burgdorferi*. Ticks were recovered from 10 of 10 full dose vaccinates and at least one *B. burgdorferi*-infected tick was recovered from 3 of the 10 (30%). In the reduced dose group, ticks were recovered from 10 of 10 vaccinates and 40% had at least one *B. burgdorferi* infected tick. Ticks were recovered from 14 of 14 nonvaccinated dogs and 12 of 14 (86%) had at least one *B. burgdorferi* infected tick. The finding that fewer infected ticks were recovered from vaccinated animals than nonvaccinated animals was previously reported in the Immunogenicity Test and Duration of Immunity Study Research Report, Dec. 28, 1993 and has been published in Fikrig et al. (1992).

G. Isolation of *B. burgdorferi* from Skin Biopsy Samples

The skin of dogs has been shown to be a good source for recovery of *B. burgdorferi* after exposure to infected ticks demonstrate *B. burgdorferi* infection and as an indicator of clearance of the spirochete from the dog. At 21 days post tick challenge, dogs were anesthetized and skin biopsies were taken from all vaccinated and nonvaccinated dogs. *B. burgdorferi* was not isolated from skin biopsies from any of the 10 dogs in the full dose bacterin group. In the reduced dose group, *B. burgdorferi* was recovered from 1 of 10 dogs (Table 32). In contrast, skin biopsies taken from 12 of 14 (86%) nonvaccinated control dogs at 21 days post challenge were positive for *B. burgdorferi*. Interestingly, the one nonvaccinated control dog that was seronegative after challenge by whole cell ELISA was one of the two control dogs that was skin biopsy negative.

TABLE 32

Isolation of *B. burgdorferi* from dogs after challenge with infected ticks and at the time of necropsy of lame dogs.

| Dog. No. | Age at First Vac. | Skin Biop.[a] | Date Lameness Observed | Reisolation of *B. burgdorferi* at Lameness/Necropsy | | | | Reisolation 12 Mos. Post Tick Attachment | | |
|---|---|---|---|---|---|---|---|---|---|---|
| | | | | Fever | Skin | Joints | Organs[b] | Skin | Joints | Organs |
| Vaccinates Full dose | | | | | | | | | | |
| 746 | 17 | − | − | | | | | | | |
| 758 | 15 | − | − | | | | | | | |
| 768 | 13 | − | − | | | | | | | |
| 782 | 12 | − | − | | | | | − | − | − |
| 835 | 17 | − | − | | | | | − | − | − |
| 847 | 15 | − | Feb | − | − | − | − | | | |
| 851 | 15 | − | − | | | | | − | − | − |
| 855 | 43 | − | − | | | | | − | − | − |
| 863 | 12 | − | − | | | | | − | − | − |
| 879 | 10 | − | − | | | | | | | |
| Vaccinates Reduced dose | | | | | | | | | | |
| 760 | 15 | − | | | | | | − | − | − |
| 774 | 13 | − | | | | | | | | |
| 786 | 11 | − | | | | | | − | − | − |
| 831 | 17 | − | Feb | − | − | − | − | | | |
| 843 | 16 | − | | | | | | | | |
| 849 | 15 | − | | | | | | | | |
| 853 | 15 | − | | | | | | − | − | − |
| 859 | 12 | − | | | | | | | | |
| 871 | 11 | − | | | | | | − | − | − |
| 881 | 10 | + | Feb | + | − | − | − | | | |
| Nonvaccinated Controls | | | | | | | | | | |
| 756 | 15 | + | − | | | | | +/+ | + | − |
| 762 | 15 | + | Jun | + | −/+ | + | − | | | |
| 764 | 15 | + | Mar | + | +/+ | + | − | | | |
| 766 | 15 | + | − | | | | | − | + | − |
| 770 | 13 | + | Jan | + | +/+ | + | − | | | |
| 772 | 13 | + | − | | | | | − | + | − |
| 776 | 13 | + | − | | | | | − | + | − |
| 845 | 15 | + | Mar | + | +/+ | + | − | | | |
| 857 | 43 | + | Jan | + | +/+ | + | − | | | |
| 861 | 12 | + | Jun | + | +/− | + | − | | | |
| 865 | 12 | + | Aug | + | − | + | − | | | |
| 867 | 12 | + | Dec | + | +/+ | + | +[s] | | | |
| 869 | 11 | + | Nov[d] | + | − | − | − | | | |
| 883 | 10 | + | Dec | + | +/+ | + | − | | | |

[a]Skin biopsies collected at tick bite sites three weeks following tick attachment.
[b]Bladder (B)/Hear (H)/Kidney (K)/Spleen (S).
[c]Biopsy taken at tick bit site/biopsy taken at a site distant to the tick bite site.
[d]November of 1994, one year following tick challenge.

(Immunogenicity Test and Duration of Immunity Study Research Report, Dec. 28, 1993). Thus, isolation of *B. burgdorferi* from the skin biopsies of dogs can be used to H. Development of Clinical Signs in Dogs Post Challenge Lameness, lethargy and fever were the clinical signs of Lyme disease in dogs used to asses the level of protection afforded by the bacterins. After eight months post tick challenge, one dog (10%) in the full dose bacterin group had exhibited lameness and two dogs (20%) in the reduced dose bacterin group have exhibited lameness (Table 32). Similar to the immunogenicity/duration study, dogs that received either the full dose or reduced dose bacterins did not exhibit lameness after four months post challenge. Lameness has been reported for 8 of 14 dogs (57%) in the nonvaccinated control group. This gives a protective index of 83% for the full dose bacterin group and a 65% protective index for the reduced dose bacterin. Lameness was observed in one leg in the vaccinates and nonvaccinated controls. As presented in the immunogenicity/duration study, the development of lameness in dogs with the natural tick challenge model occurred over an extended period of time. The temporal observation of lameness for dogs in the reduced dose study is presented in FIG. 7. In comparison to the immunogenicity/duration study, the development of lameness in nonvaccinated control dogs in the reduced dose study occurred over a slightly longer period of time. Dogs were monitored for other clinical signs of Lyme disease including fever and lethargy. The one lame dog in the full dose bacterin group did not exhibit fever of $\geq 103.5$ nor did the dog exhibit any lethargy. One of the two lame dogs in the reduced dose group had a fever of 103.7° F. for one day. All nonvaccinated control dogs had temperatures of $\geq 103.5$ at the time lameness was observed. Lethargy was not observed in any of the lame dogs.

I. Isolation of *B. burgdorferi* from Lame Dogs

Dogs were necropsied within three to four days of the episode of lameness and samples the skin, joints and organs were cultured for isolation of *B. burgdorferi*. *B. burgdorferi* was not isolated from the lame vaccinates in the full dose and reduced dose bacterin groups (Table 32). In contrast, *B. burgdorferi* was isolated from the skin and joints of all of the lame nonvaccinated controls and from the spleen of one lame control dog. In all control dogs, the spirochete was recovered from skin biopsy samples taken at sites distant from the tick bite. Results showing recovery of *B. burgdorferi* from lame nonvaccinated control dogs and not from lame vaccinates were reported in the immunogenicity/duration study.

III. DISCUSSION

The full dose bacterin used in the study contained $5\times10^8$ cells each of *B. burgdorferi* isolates from two distinct seroprotective groups. Results demonstrated that vaccinated dogs developed borreliacidal antibody that was directed against major protective antigens of *B. burgdorferi*. A tick challenge model was developed and used to evaluate the ability of the bacterin to protect dogs against clinical Lyme disease. At seven months post second vaccination, dogs were challenged with *B. burgdorferi* infected ticks and observed for an additional seven months. The bacterin protected dogs against clinical signs of Lyme disease that included lameness, fever and lethargy. The finding that *B. burgdorferi* was not recovered from lame vaccinated but was recovered from all lame control dogs suggested enhanced clearance of the spirochete in vaccinated dogs. Data from the study were accepted by APHIS as demonstration of immunogenicity and duration of immunity of the bacterin.

The tick challenge model was incorporated into bacterin efficacy testing at a relatively late stage in development of the bacterin described above. Therefore, minimal immunizing dose studies had not been conducted. This Example demonstrates the vaccination of dogs with a bacterin that contained a 10-fold reduction in the numbers of each isolate of *B. burgdorferi*. As a comparison to the reduced dose bacterin group, additional dogs were vaccinated with the bacterin containing the original full dose of *B. burgdorferi*. Since duration of immunity was previously demonstrated, dogs in the reduced antigen dose study were challenged at 4 weeks after the second vaccination. The tick challenge model was again used in the reduced antigen dose study because the challenge model is the most relevant test of vaccine efficacy.

As a first step in determining whether the reduction in *B. burgdorferi* cell numbers affected bacterin efficacy, the humoral immune response of dogs was evaluated. The whole cell borreliacidal and OspA antibody titers of dogs in the reduced dose group. In general, antibody titers in dogs vaccinated with the full dose bacterin were slightly higher than titer in dogs vaccinated with the reduced dose bacterin. However, the antibody titers between bacterin groups did not differ by more than two-fold and were not significantly different. Antibody titers in the reduced dose study were comparable to titers reported in the immunogenicity and duration study (Table 33). The fact that bacterins used in the reduced dose study had undergone an additional year storage at 4° C. provides evidence for the stability of the bacterin. More importantly, results demonstrated the reproducibility of the experimental conditions and the consistency of the reduced dose and full dose bacterin in generating similar humoral immune responses to *B. burgdorferi*.

TABLE 33

Comparison of antibody titers from dogs in the immunogenicity/duration and reduced dose studies vaccinated with full dose and reduced dose bacterins.

| | | GMT antibody titer[a] to *B. burgdorferi*: | | | | | |
|---|---|---|---|---|---|---|---|
| | Animal | Borreliacidal | | OspA ELISA | | Whole cell ELISA | |
| Bacterin | Study | C-1-11 | S-1-10 | C-1-11 | S-1-10 | C-1-11 | S-1-10 |
| Full Dose | Immun./ duration | 1076 | 520 | 381 | 640 | 1236 | 816 |
| Full dose | Reduced dose Study | 970 | 597 | 452 | 299 | 788 | 520 |
| Reduced dose | Reduce dose study | 640 | 597 | 368 | 394 | 485 | 520 |

[a]Titers were at three to four weeks post second vaccination.

Isolation of *B. burgdorferi* from tissue samples of dogs has been used as an indicator of infection with the spirochete. Example 14 using the full dose bacterin shows that after exposure to *B. burgdorferi* infected ticks, the spirochete is recovered from the skin of fewer vaccinated dogs than nonvaccinated controls dogs. This Example also shows that *B. burgdorferi* was recovered from skin biopsies from fewer vaccinates than control dogs after tick challenge. There was no significant difference between the reduced dose and full dose bacterin groups in recovery of *B. burgdorferi* from skin biopsies post challenge. The difference between vaccinates and control dogs in the isolation of *B. burgdorferi* from tissue samples was also observed at the time of necropsy of lame dogs. *B. burgdorferi* was not recovered from any tissue of the one lame dog in the full dose bacterin group or from either of the two dogs in the reduced dose group. These results are identical to the results from the immunogenicity and duration study. In contrast, *B. burgdorferi* was isolated from all lame nonvaccinated control dogs in both the immunogenicity/duration and reduced dose studies. Although the mechanisms have not been defined, these findings indicated that the full dose and reduced dose bacterins were similar in their ability to reduce the spirochete burden in the dogs at the time of infection and/or generate an immune response that resulted in enhanced clearance of the spirochete.

The primary clinical signs of Lyme disease in the dog are lameness and to lesser extent fever and lethargy. The immunogenicity/duration study conducted with the full dose bacterin in Example 14 demonstrated that lameness and other clinical signs were observed in 12% of the vaccinates compared to 83% of the nonvaccinated controls. In this reduced dose study, similar results were observed with 10% lameness reported in the full dose group and 20% in the reduced dose group. In both studies, lameness in nonvaccinated control dogs occurred beginning at two months post challenge and then at periodic times. At the termination of the immunogenicity/duration study at eight months post challenge, lameness was reported in approximately 80% of the nonvaccinated control dogs. In the reduced dose study, at eight months post tick challenge, lameness has been reported in approximated 60% of the nonvaccinated controls. The chronic nature of the disease and delayed onset of clinical signs is not unexpected using a challenge model that so closely mimics natural field exposure. In Appel et al. (1993) it is reported that manifestation of clinical Lyme disease including lameness was observed as late as five months after challenge of dogs with infected ticks. The reason for the extended time in development of clinical disease in the reduced dose study is not known. In this reduced dose study, parameters of the tick challenge such as the number of infected ticks/dog an infection rates of ticks were kept similar to the parameters used in the immunogenicity/duration study, Example 14. Although the tick challenge model represents the natural route of exposure, dosage and virulence of *B. burgdorferi* encountered by the dog, it is these same parameters that most directly affect the outcome of the challenge.

The data presented in this Example demonstrate that a bacterin formulated at reduced antigen dose level is equally effective as the full dose bacterin in generation of a protective antibody response to *B. burgdorferi* and in reduction of infection with the spirochete post tick challenge. Both the full dose and reduced dose bacterins protected dogs against the clinical signs of Lyme disease.

References

Anderson, J. F., et al. (1988) J. Clin. Microbiol. 26: 2209–2212.
Appel, Max J. G., et al. (1993) J. Inf. Dis. 167: 651–664.
Asbrink, E. et al. (1988) Ann. N.Y. Acad. Sci. 539: 4–15.
Barthold, S. W. et al. (1988) Ann. N.Y. Acad. Sci. 539: 264–273.
Barthold, S. W. et al. (1993) Infect. Immun. 61:4696–4702.
15 Bergstrom, S. et al., (1991) Scand. J. Infect. Dis.—Suppl. 77: 102–107.
Burchhardt, (1911) Frankf. Z. Pathol. 6: 352.
Burgdorfer, W. A. et al., (1982) Science 216: 1317–1319.
Callister, S. M., et al. (1991) J. Clin. Microbiol. 29: 1773–1776.
Callister, S. M. et al., (1992) J. Infec. Dis. 167:158–164.
Callister, S. M. et al. (1 994) Archive of Intern. Med. 154:1625–32.
Dlesk, A., Proceedings of the First National Conference on Lyme Disease Testing, Deaborn, Michigan, 1990, pp. 7–22.
Fikrig, E., et al. (1992) Proc. Natl. Acad. Sci. 89: 5418–5421.
Fikrig, E. et al., (1992) Infect. Immun. 60: 657.
Fikrig, E. et al., (1990) Science 250: 553.
Georgilis, K. et al. (1992) J. Intect. Dis. 166:440–444.
Gern, L. et al., (1993) J. Infect. Dis. 167: 971–975.
Halperin, J. J., (1991) Scand. J. Infect. Dis.—Suppl. 77: 74–80.
Halperin, J. J. et al., (1988) Ann. N.Y. Acad. Sci. 539: 24–34.
Hsien-Jue, C. et al. (1992) JAVMA 201: 403–411.
Jobe, D. A. et al. (1994) J. Clin. Microbiol.; 32:61 8–22.
Johnson, R. C., U.S. Pat. No. 4,721,617, issued Jan. 20, 1988.
Johnson, R. C. et al., (1988) Ann. N.Y. Acad. Sci, 539: 258–263.
Johnson, R. C. et al. (1986a) Zbl. Bakt. Hyg. A. 263: 45–48.
Johnson, R. C. et al., (1986b) Infect. Immun. 54: 897–898.
Kochi, S. K. et al. (1988) Infect. and Immun. 56: 314–321.
Lacombe, E, et al., (1993) J. Infect. Dis. 167:1236–1238.
Laemmli, E. K. (1970) Nature 227:680–685.
Lane, R. S. et al. (1989) J. Clin. Microbiol. 27: 2344–2349.
LeFebvre, R. B. et al. (1990) J. Clin. Microbiol. 28: 700–707.
Levy, S. A. et al. (1992) Canine Practice 17: 5–14.
Lim, L. C. et al., (1993) Clin. Diag. Lab. Immunol. 1:44–50. press).
Lovrich, S. D. et al. (1993) Infect. and Immun. 61:4367–4374.
Luft., B. J. et al., (1988) Ann. N.Y. Acad. Sci, 539: 352–361.
Nelson, J. A. et al. (1991) J. Clin. Microbiol. 29: 1732–1734.
Neu, H., (1988) Ann. N.Y. Acad. Sci., 539: 314–316.
Piesman, J., J. R. Oliver, and R. J. Sinsky. (1990) Am. J. Trop. Med. Hyg. 42: 352–357.
Ramachandra, R. N. et al. (1992) J. Med. Entomol. 29:818–826.
Reik, L., (1988) Ann. N.Y. Acad. Sci. 539: 1–3.
Roehrig, J. T. et al. (1992) Journ. Immunol. 149: 3648–3653.
Sachsenmeirer, K. F. et al. (1992) J. Clin. Microbiol. 30:1457–1461
Schaible, U. E. et al. (1993) Immunol. Let. 3–6:219–226.
Schaible, U. E. et al. (1990) Proc. Natl. Acad. Sci. USA 87:3768–3772.
Schmitz, J. L. et al. (1991) Infect. and Immun. 59: 3815–3818.
Schwan, T. G. et al. (1991) Scand. J. Infect. Dis.—Suppl. 77: 94–101.
Shih, G. et al. (1991) Scand J. Infect. Dis.—Suppl. 77:85–87.

Skoldenberg, B. et al. (1988) Ann. N.Y. Acad. Sci. 539: 317–323.
Stanek. G. et al. (1991) Scand J. Infect. Dis.—Suppl. 77: 85–87.
Stanek, G. et al. (1986) Zentralbl. Bakteriol. Mikrobiol. Hyg. A. 263: 491.
Steere, A. C., (1991) Scand. J. Infect. Dis.—Suppl. 77: 51–54.
Steere, A. C. et al. (1983) N. Engl. J. Med. 308: 733–740.
Steere, A. C. et al. (1977) Ann. Intern Med. 86: 685–698.
Steere, A. C. et al., (1977) Arthritis Rheum. 20: 7.
Towbin, H. et al. (1979) Proc. Natl. Acad. Sci. 76:4350–4354.
Weber, K. et al., (1988) Ann. N.Y. Acad. Sci. 539: 325–345 (1988).

What is claimed is:

1. A bacterin which comprises per dose an effective immunizing amount of two non-crossprotective inactivated *Borrelia burgdorferi* isolates, an adjuvant in an amount effective to enhance the immunogenicity of the inactivated *Borrelia burgdorferi* isolates and a suitable carrier, wherein one isolate is seroprotective group B strain C-1-11 of *Borrelia burgdorferi* having ATCC deposit designation PTA-1679 and the other isolate is selected from the group consisting of seroprotective group A *Borrelia burgdorferi* and seroprotective group C *Borrelia burgdorferi*.

2. The bacterin of claim 1, wherein the effective immunizing amount of the non-crossprotective isolates of inactivated *Borrelia burgdorferi* is an amount from about $10^4$ organisms to about $10^{10}$ organisms of each isolate.

3. The bacterin of claim 2, wherein the effective immunizing amount of the non-crossprotective isolates of inactivated *Borrelia burgdorferi* is an amount from about $10^4$ organisms to about $10^9$ organisms of each isolate.

4. The bacterin of claim 3, wherein the effective immunizing amount of the non-crossprotective isolates of inactivated *Borrelia burgdorferi* is an amount from about $10^4$ organisms to about $10^8$ organisms of each isolate.

5. The bacterin of claim 3 wherein the effective immunizing amount of the non-crossprotective isolates of inactivated *Borrelia burgdorferi* is about $10^7$ organisms of each isolate.

6. The bacterin of claim 3 wherein the effective immunizing amount of the non-crossprotective isolates of inactivated *Borrelia burgdorferi* is about $5 \times 10^7$ organisms of each isolate.

7. The bacterin of claim 3 wherein the effective immunizing amount of the non-crossprotective isolates of inactivated *Borrelia burgdorferi* is about $5 \times 10^8$ organisms of each isolate.

8. The bacterin of claim 1, wherein the non-crossprotective isolates of *Borrelia burgdorferi* are inactivated by an agent selected from the group consisting of binary ethyleneimine, formalin and β-propriolactone.

9. The bacterin of claim 8, wherein the non-crossprotective isolates of *Borrelia burgdorferi* are inactivated by binary ethyleneimine.

10. The bacterin of claim 1, wherein the other isolate is of seroprotective group A *Borrelia burgdorferi*.

11. The bacterin of claim 10, wherein the seroprotective group A isolate of *Borrelia burgdorferi* is a strain selected from the group consisting of S-1-10 having ATCC deposit designati on PTA-1680, 297 and B31.

12. The bacterin of claim 11, wherein the seroprotective group A isolate of *Borrelia burgdorferi* is strain S-1-10 having ATCC deposit designation PTA-1680.

13. The bacterin of claim 1, wherein the adjuvant is selected from the group consisting of aluminum hydroxide, saponin, aluminum phosphate, carbopol and lipopolysaccharide.

14. The bacterin of claim 13, wherein the adjuvant is aluminum hydroxide.

15. The bacterin of claim 14, wherein the effective amount of the adjuvant is an amount from about 1.0% by volume to about 15% by volume.

16. The bacterin of claim 1, wherein the effective amount of the aluminum hydroxide adjuvant is an amount from about 5% by volume to about 10% by volume.

17. The bacterin of claim 16, wherein the effective amount of the adjuvant is about 7.5% by volume.

18. The bacterin of claim 1, wherein the suitable carrier comprises an aqueous buffer and preservatives.

19. The bacterin of claim 18, wherein the aqueous buffer is physiological saline.

20. The bacterin of claim 18, wherein the preservatives comprise gentamicin and nystatin.

21. The bacterin of claim 1, further comprising an effective immunizing amount of a third non-crossprotective isolate of inactivated *Borrelia burgdorferi*.

22. A method of immunizing an animal against infection by *Borrelia burgdorferi* which comprises administering to the animal a dose of the bacterin of claim 1.

23. The method of claim 22, wherein the animal is a mammal.

24. The method of claim 23, wherein the mammal is a human.

25. The method of claim 23, wherein the mammal is a dog.

26. The method of claim 25, wherein the dog is at least about six weeks old.

27. The method of claim 22, further comprising administering to the animal an additional dose of the bacterin at an interval of time after administration of the preceding dose.

28. The method of claim 27, wherein the interval of time is from about two weeks to about five weeks.

29. The method of claim 22, wherein the administration is by intramuscular injection.

30. The method of claim 22, wherein the administration is by subcutaneous injection.

31. A method of immunizing an animal against infection by *Borrelia burgdorferi* which comprises administering to the animal a dose of a bacterin which comprises an effective immunizing amount of at least two non-crossprotective isolates of inactivated *Borrelia burgdorferi*, an adjuvant in an amount effective to enhance the immunogenicity of the inactivated *Borrelia burgdorferi* and a suitable carrier for the immunization of animals against infection by *Borrelia burgdorferi*, wherein one isolate is seroprotective group B strain C-1-11 of *Borrelia burgdorferi* having ATCC deposit designation PTA-1679 and the other isolate is selected from the group consisting of seroprotective group A *Borrelia burgdorferi* and seroprotective group C *Borrelia burgdorferi*.

32. The method of claim 31, wherein the effective immunizing amount of the non-crossprotective isolates of inactivated *Borrelia burgdorferi* is an amount from about $10^4$ organisms to about $10^{10}$ organisms of each isolate.

33. The method of claim 31, wherein the effective immunizing amount of the non-crossprotective isolates of inactivated *Borrelia burgdorferi* is an amount from about $10^4$ organisms to about $10^9$ organisms of each isolate.

34. The method of claim 31, wherein the effective immunizing amount of the non-crossprotective isolates of inactivated *Borrelia burgdorferi* is an amount from about $10^4$ organisms to about $10^8$ organisms of each isolate.

35. The method of claim 31, wherein the effective immunizing amount of the non-crossprotective isolates of inactivated *Borrelia burgdorferi* is about $10^7$ organisms of each isolate.

36. The method of claim 31, wherein the other isolate is of seroprotective group A *Borrelia burgdorferi*.

37. The method of claim 36, wherein the seroprotective group A isolate of *Borrelia burgdorferi* is a strain selected from the group consisting of S-1-10 having ATCC deposit designation PTA-1680, 297 and B31.

38. The method of claim 37, wherein the seroprotective group A isolate of *Borrelia burgdorferi* is strain S1-10 having ATCC deposit designation PTA-1680.

* * * * *